(12) United States Patent
Boehm et al.

(10) Patent No.: US 7,423,042 B2
(45) Date of Patent: Sep. 9, 2008

(54) COMPOUNDS

(75) Inventors: Jeffrey C. Boehm, King of Prussia, PA (US); John J. Taggart, King of Prussia, PA (US)

(73) Assignee: Glaxo Group Limited, Greenford, Middlesex (GB)

( * ) Notice: Subject to any disclaimer, the term of this patent is extended or adjusted under 35 U.S.C. 154(b) by 34 days.

(21) Appl. No.: 11/388,840

(22) Filed: Mar. 24, 2006

(65) Prior Publication Data

US 2006/0217401 A1 Sep. 28, 2006

Related U.S. Application Data

(60) Provisional application No. 60/665,323, filed on Mar. 25, 2005.

(51) Int. Cl.
- A61K 31/519 (2006.01)
- C07D 471/02 (2006.01)
- C07D 487/04 (2006.01)
- A61P 29/00 (2006.01)

(52) U.S. Cl. .................. 514/264.11; 544/279
(58) Field of Classification Search ............ 514/264.11; 544/279
See application file for complete search history.

(56) References Cited

U.S. PATENT DOCUMENTS

| | | | |
|---|---|---|---|
| 3,843,663 A | 10/1974 | Williams et al. |
| 4,560,691 A | 12/1985 | Lesher et al. |
| 4,886,807 A | 12/1989 | Kitamura et al. |
| 4,897,395 A | 1/1990 | Duch et al. |
| 5,304,560 A | 4/1994 | Shimazaki et al. |
| 5,409,930 A | 4/1995 | Spada et al. |
| 5,426,110 A | 6/1995 | Gossett et al. |
| 5,466,692 A | 11/1995 | Ellingboe |
| 5,547,954 A | 8/1996 | Henrie, II et al. |
| 5,597,776 A | 1/1997 | Bratz et al. |
| 5,620,981 A | 4/1997 | Blankley et al. |
| 5,733,913 A | 3/1998 | Blankley et al. |
| 5,733,914 A | 3/1998 | Blankley et al. |
| 5,760,220 A | 6/1998 | Giguere et al. |
| 5,767,097 A | 6/1998 | Tam |
| 5,817,670 A | 10/1998 | Takayama et al. |
| 5,945,422 A | 8/1999 | Doherty et al. |
| 6,083,948 A | 7/2000 | Wilde |
| 6,200,977 B1 | 3/2001 | Cusing et al. |
| 6,277,989 B1 | 8/2001 | Chakravarty et al. |
| 6,476,031 B1 | 11/2002 | Chakravarty et al. |
| 6,479,463 B1 | 11/2002 | Wang et al. |
| 6,492,520 B1 | 12/2002 | Chen |
| 6,498,163 B1 | 12/2002 | Boschelli et al. |
| 6,528,508 B2 | 3/2003 | Salituro et al. |
| 6,528,513 B2 | 3/2003 | Cusing et al. |
| 6,593,333 B1 | 7/2003 | Cumming |
| 6,800,626 B2 | 10/2004 | Salituro et al. |
| 6,809,199 B2 | 10/2004 | Doherty et al. |
| 6,838,559 B2 | 1/2005 | Vaccaro et al. |
| 6,875,769 B2 | 4/2005 | Chen |
| 7,235,551 B2 | 6/2007 | Adams et al. |
| 2003/0114671 A1 | 6/2003 | Chen |
| 2004/0009993 A1 | 1/2004 | Angiolini |
| 2004/0063658 A1 | 4/2004 | Roberts et al. |
| 2004/0116697 A1 | 6/2004 | Adams et al. |
| 2004/0142945 A1 | 7/2004 | Barbosa et al. |
| 2004/0209901 A1 | 10/2004 | Adams et al. |
| 2004/0224958 A1 | 11/2004 | Booth et al. |
| 2004/0235847 A1 | 11/2004 | Quan et al. |
| 2004/0236084 A1 | 11/2004 | Biwersi et al. |
| 2004/0242604 A1 | 12/2004 | Bhattacharya et al. |
| 2005/0187217 A1 | 8/2005 | Wilson et al. |
| 2005/0203109 A1 | 9/2005 | Adams et al. |
| 2005/0272728 A1 | 12/2005 | Altenbach et al. |
| 2006/0235029 A1 * | 10/2006 | Callahan et al. .......... 514/262.1 |
| 2006/0235030 A1 | 10/2006 | Callahan et al. |
| 2006/0258687 A1 | 11/2006 | Boehm et al. |

FOREIGN PATENT DOCUMENTS

| | | |
|---|---|---|
| EP | 0 278 686 | 2/1988 |
| EP | 0 530 994 | 3/1993 |
| GB | 2 123 830 | 2/1984 |
| JP | 1-261306 | 10/1989 |
| JP | 20000038350 | 8/2000 |
| JP | 2003/127542 | 5/2003 |

(Continued)

OTHER PUBLICATIONS

Disorders Index of the National Institute of Neurological Disorders and Stroke, http://www.ninds.nih.gov/disorders/disorder_index.htm?css=print (NINDS Index).*
Hashimoto, et al., J. of Pharmacol. and Experi. Therap., vol. 293, No. 2, pp. 370-375, 2000.*
Hensley, et al., J. of Neurochem., vol. No. 5, 1999, pp. 2053-2058.*
Johnson, et al., Science, vol. 298, Dec. 6, 2002, 1911-1912.*
Kanda, et al., Brit. J. PHarmacol, vol. 132 (8), 2001, 1657-1664.*
, Et al., Chin. Med. J. 2006, 119 (13): 1088-1093.*
U.S. Appl. No. 11/613,517, filed Dec. 20, 2006, Adams, et al.
U.S. Appl. No. 11/613,598, filed Dec. 20, 2006, Adams, et al.
U.S. Appl. No. 11/871,039, filed Oct. 11, 2007, Adams, et al.
U.S. Appl. No. 11/839,830, filed Aug. 16, 2007, Adams, et al.
U.S. Appl. No. 11/839,833, filed Aug. 16, 2007, Adams, et al.

(Continued)

Primary Examiner—Mark L. Berch
Assistant Examiner—Cecilia M Jaisle
(74) Attorney, Agent, or Firm—Dara L. Dinner; Stephen Venetianer; Charles M. Kinzig

(57) ABSTRACT

This invention relates to a novel group of 8-Alkyl/Aryl-4-aryl-2-N-(alkylamino)-N'''-substituted-N'-cyanoguanidino-8H-pyrido[2,3-d]pyrimidin-7-one compounds, processes for the preparation thereof, the use thereof in treating CSBP/p38 kinase mediated diseases and pharmaceutical compositions for use in such therapy.

20 Claims, No Drawings

FOREIGN PATENT DOCUMENTS

| | | |
|---|---|---|
| JP | 2004-203751 | 7/2004 |
| WO | WO 92/12154 | 7/1992 |
| WO | WO 94/19350 | 9/1994 |
| WO | WO 95/15952 | 6/1995 |
| WO | WO 95/19774 | 7/1995 |
| WO | WO 95/33750 | 12/1995 |
| WO | WO 97/38992 | 10/1997 |
| WO | WO 98/05661 | 2/1998 |
| WO | WO 98/08846 | 3/1998 |
| WO | WO 98/27098 | 6/1998 |
| WO | WO 98/33798 | 8/1998 |
| WO | WO 99/41253 | 8/1999 |
| WO | WO 99/61444 | 12/1999 |
| WO | WO 99/64400 | 12/1999 |
| WO | WO 00/23444 | 4/2000 |
| WO | WO 00/43374 | 7/2000 |
| WO | WO 01/19828 | 3/2001 |
| WO | WO 01/42243 | 6/2001 |
| WO | WO 01/55147 | 8/2001 |
| WO | WO 01/70741 | 9/2001 |
| WO | WO 02/058695 | 8/2002 |
| WO | WO 02/059083 | 8/2002 |
| WO | WO02/060869 | 8/2002 |
| WO | WO 02/102315 | 12/2002 |
| WO | WO 2005/014558 | 2/2005 |

OTHER PUBLICATIONS

U.S. Appl. No. 11/839,834, filed Aug. 16, 2007, Adams, et al.
U.S. Appl. No. 11/908,435, filed Sep. 12, 2007, Callahan, et al.
U.S. Appl. No. 11/908,440, filed Sep. 12, 2007, Callahan, et al.
U.S. Appl. No. 11/908,839, filed Sep. 17, 2007, Callahan, et al.
U.S. Appl. No. 11/908,340, filed Sep. 11, 2007, Boehm, et al.
Adams et al., Progress in Medicinal Chemistry, vol. 38, pp. 2-61 (2001).
Armarego, W., Chem. Soc., Quinazolines, Part IV (JCSOA9) p. 561 (1962).
Boehm et al., J. Med. Chem. vol. 39, pp. 3929-3937 (1996).
Votta et al., Bone, vol. 15 (5) pp. 533-538 (1994).
Bradlerova et al., Chem. Zvesti, vol. 29 (6), pp. 795-802 (1975).
de Silva et al., J. Chem. Soc., vol. 4, pp. 685-690 (1995).
Engel & Steglich, Liebigs Ann. Chem., p. 1916 (1978).
Ferles et al., Collect. Czech. Chem. Commun., vol. 5 (46), pp. 1167-1172 (1981).
Fischer et al., Rec. Trav. Chim. Pays. Bas., vol. 84, p. 439 (1965).
Fulmer et al., J. Heterocycl. Chem., vol. 17 (4), pp. 799-800 (1980).
Gilbert, E., Synthesis, pp. 30-32 (1972).
Han et al., Science, vol. 265, pp. 808-811 (1994).
Hunter et al., Academic Press, San Diego, vol. 200, p. 3 (1991).
Irwin et al., Archives of Internal Medicine, vol. 157 (17), pp. 1981-1987 (1997).
Ishibashi et al., Chem. Pharm. Bull., vol. 37(8), pp. 2214-2216 (1989).
Johnson et al., PG.A., J.Chem.Soc., Perkin Trans., vol. 1, pp. 895-905 (1996).
Jurkowska-Kowalczyk, R., Chem., vol. 51 (6), pp. 1191-1199 (1977).
Katritzky et al., Synthesis, pp. 45-47 (Jan. 1993).
Kawasaki et al., J. Bio. Chem., vol. 272(30), pp. 18518-18521 (1997).
Mikailu et al., Zh. Obshch. Khim., vol. 56 (7), pp. 1513-1517 (1986).
Morton et al., Tetrahedron Letters, p. 4123 (1982).
Protecting Groups in Organic Synthesis, 2$^{nd}$ Edition, Greene TW and Wuts PSM, Wiley-Interscience, New York, pp. 10-174 (Hydroxyl and Phenolic) and pp. 309-403 (NH protection) (1991).
Santilli et al., J. Heterocycl Chem., vol. 8, pp. 445-453 (1971).
Snieckus, V., Tetrahedron Letters, vol. 29, p. 2135 (1988).
Stille et al., J. Amer. Chem. Soc., vol. 109, p. 5478 (1978).
Strzybny et al., J. Org. Chem., vol. 28, p. 3381 (1963).
Terashimia et al., M., Chem. Pharm. Bull., vol. 11, p. 4755 (1985).
Thompson et al., J. Org. Chem., vol. 49, p. 5237 (1984).
Uno et al., Bull. Chem. Soc. Japan., vol. 69, pp. 1763-1767 (1996).
Vartanyan et al., vol. 40, (9), pp. 552-560 (1987).
Borrel, et al., Coll. Czech. Chem. Commun., 1996, 61(6) pp. 901-909.
Baker et al., J. Heterocyclic Chem., 1964, vol. 1, pp. 263-270.
Anderson et al., J. Org. Chem., 1977, vol. 42, p. 993.
Victory et al., Heterocycles, 1985, 23(5), pp. 1135-1141.
Gallagher et al., Bioorganic and Med Chem, vol. 5(1), pp. 49-64 (1997).
Garigipati, R., Tetrahedron Letters, vol. 31, p. 190 (1989).
Kumada et al., Tetrahedron Letters, vol. 22, p. 5319 (1981).
Lamartina et al., Boll. Chim. Farm., vol. 129 (12), pp. 314-316 (1990).
Victory et al., Heterocycles, 1985, 23(8), pp. 1947-1950.
Victory et al., AFINIDAD, Mar. 1989, vol. 46, pp. 107-113 (Spanish).
Victory et al., J. Heterocycl. Chem, 1988, vol. 25, pp. 245-247.
Klotzer et al., Monatsh Chem., 1965, vol. 96, p. 1567.
Nishikawa et al., Chemical Pharm. Bull., 1976, vol. 24(9), pp. 2057-2077.
Carboni et al., *Gazzetta Chimica Italiana*, vol. 97(8) pp. 1262-1273 (1967).
Carboni et al., *Gazzetta Chimica Italiana*, vol. 98(10) pp. 1174-1188 (1968).
Ferrarini et al., *Journal of Heterocyclic Chemistry*, vol. 21(2) pp. 417-419 (1984).
Ferrarini et al., *Journal of Heterocyclic Chemistry*, vol. 34(5) pp. 1501-1510 (1997).
Rewcastle et al., Journal of Medicinal Chemistry, 1996 39(6), pp. 1823-1835.
Zavyalov, et al., Khim Farm Zh, vol. 26(3), p. 88 (1992) (With Translation).
Foster, et al., Drug News Perspect., vol. 13(8) pp. 488-497 (2000).
Hanson, G., Expert Opinion on Therapeutic Patents, vol. 7(7) pp. 729-733 (1997).
Henry, et al., Bioorganic & Medicinal Chemistry Letters, vol. 8 pp. 3335-3340 (1998).
Herlaar, et al., *Molecular Medicine Today*, vol. 5 pp. 439-447 (1999).
Hurlbert, et al., J. Med. Chem., 1968, vol. 11, pp. 703-707.
Khabar, Khalid, *Journal of Interferon & Cytokine Research*, vol. 25 pp. 1-10 (2005).
Lee, et al., Immunopharmacology, vol. 47(2-3) pp. 185-201 (2000).
Marin, et al., Blood, vol. 98(3) pp. 667-673 (2001).
Schoffstall, J Org Chem, vol. 36(16) pp. 2385-2387 (1971).
Underwood, et al., Journal of Pharmacology and Experimental Therapeutics, vol. 293 (1) pp. 281-288 (2000).
Wadsworth, et al., Journal of Pharmacology and Experimental Therapeutics, vol. 291(2) pp. 680-687 (1999).
Harc, et al., J. Med Chem., vol. 47 pp. 4731-4740 (2004).
Hunt, et al., Bioorganic & Medicinal Chemistry Letters, vol. 13 pp. 467-470 (2003).

\* cited by examiner

```
SEQUENCE LISTING

<160> NUMBER OF SEQ ID NOS: 1

<210> SEQ ID NO 1
<211> LENGTH: 21
<212> TYPE: PRT
<213> ORGANISM: Artificial Sequence
<220> FEATURE:
<223> OTHER INFORMATION: Epidermal Growth Factor Receptor-Derived
      Peptide

<400> SEQUENCE: 1

Lys Arg Glu Leu Val Glu Pro Leu Thr Pro Ser Gly Glu Ala Pro Asn
 1               5                  10                  15

Gln Ala Leu Leu Arg
             20
```

COMPOUNDS

RELATED APPLICATIONS

This application claims the benefit of priority from U.S. Ser. No. 60/665,323, filed 25 Mar. 2005.

FIELD OF THE INVENTION

This invention relates to a novel group of 8-Alkyl/Aryl-4-aryl-2-N-(alkylamino)-N"-substituted-N'-cyanoguanidino-8H-pyrido[2,3-d]pyrimidin-7-one compounds, processes for the preparation thereof, the use thereof in treating CSBP/p38 kinase mediated diseases and pharmaceutical compositions for use in such therapy.

BACKGROUND OF THE INVENTION

Intracellular signal transduction is the means by which cells respond to extracellular stimuli. Regardless of the nature of the cell surface receptor (e.g. protein tyrosine kinase or seven-transmembrane G-protein coupled), protein kinases and phosphatases along with phospholipases are the essential machinery by which the signal is further transmitted within the cell [Marshall, J. C. Cell, 80, 179-278 (1995)]. Protein kinases can be categorized into five classes with the two major classes being tyrosine kinases and serine/threonine kinases, depending upon whether the enzyme phosphorylates its substrate(s) on specific tyrosine(s) or serine/threonine(s) residues [Hunter, T., Methods in Enzymology (Protein Kinase Classification) p. 3, Hunter, T.; Sefton, B. M.; eds. vol. 200, Academic Press; San Diego, 1991].

Three major related intracellular pathways, the mitogen-activated kinases, or MAPKs, are now understood to transduce signals from many extracellular stimuli such as environmental stress, infectious agents, cytokines and growth factors. The MAPKs modulate the activity of numerous cell functions such as translocation and activation of transcription factors that control transcription of effector molecules such as cytokines, COX-2, iNOS; the activity of downstream kinases that effect translation of mRNAs; and cell cycle pathways through transcription or modification of enzymes. One of these three major pathways is the p38 MAPK pathway, which refers in most cell types to the isoform p38α which is ubiquitously expressed. The role of p38 in a multitude of functions, particularly related to inflammatory response has been elucidated using selective p38 inhibitors in numerous in vitro and in vivo studies. These functions have been extensively reviewed and a summary can be found in Nature Reviews [Kumar, S. Nature Rev. Drug Discovery, 2:717 (2003)]

Extracellular stimuli such as those described above are generated in a number of chronic diseases which are now understood to have a common underlying pathophysiology termed inflammation. An environmental insult or local cell damage activates cellular response pathways, including but not limited to p38; local cells then generate cytokines and chemokines, in turn recruiting lymphocytes such as neutrophils and other granulocytes. n a secondary response, the consequences include recruitment of additional lymphocytes such as additional phagocytic cells or cytotoxic T cells, and ultimately the adaptive immune response is initiated through activation of T cells. It is not currently fully understood how this acute inflammatory response becomes a chronic response leading to diseases such as rheumatoid arthritis (RA), atherosclerosis, chronic obstructive pulmonary disease (COPD), inflammatory bowel disease (IBD), etc. Nevertheless, the features of inflammation are recognized to contribute to a large number of chronic diseases and pathways such as the p38 pathway are accepted to contribute to the initiation of inflammatory diseases.

For example, atherosclerosis is regarded as a chronic inflammatory disease, which develops in response to injury of the vessel wall and is characterized by the complex development of an occlusive and prothrombotic atheroma. The pathogenesis of this lesion generally involves endothelial dysfunction (reduced bioavailable NO), adhesion molecule expression, adhesion and infiltration of leukocytes, cytokine and growth factor generation, accumulation of foam cells, expansion of extracellular lipid and matrix, activation of matrix metalloproteases (MMPs) and proliferation of vascular smooth muscle cells.

The discovery of p38 (initially termed CSBP, now p38; the isoforms p38α and p38β are the targets of the compounds described) provided a mechanism of action of a class of anti-inflammatory compounds for which SK&F 86002 was the prototypic example. These compounds inhibited IL-1 and TNF synthesis in human monocytes at concentrations in the low uM range [Lee, et al., Int. J. Immunopharmac. 10(7), 835(1988)] and exhibited activity in animal models which are refractory to cyclooxygenase inhibitors [Lee; et al., Annals N.Y. Acad. Sci., 696, 149(1993)].

The mechanism by which stress signals (including bacterial and viral infection, pro-inflammatory cytokines, oxidants, UV light and osmotic stress) activate p38 is through activation of kinases upstream from p38 which in turn phosphorylate p38 at threonine 180 and tyrosine 182 resulting in p38 activation. MAPKAP kinase-2 and MAPKAP kinase-3 have been identified as downstream substrates of CSBP/p38 which in turn phosphorylate heat shock protein Hsp27 and other substrates. Additional downstream substrates known to be phosphorylated by p38 include kinases (Mnk1/2, MSK1/2 and PRAK) and transcription factors (CHOP, MEF2, ATF2 and CREB). While many of the signaling pathways required for transduction of stress stimuli remain unknown it appears clear that many of the substrates for p38 listed above are involved. [Cohen, P. Trends Cell Biol., 353-361(1997) and Lee, J. C. et al, Pharmacol. Ther. vol. 82, nos. 2-3, pp. 389-397, 1999]. There is also emerging evidence that p38 is involved in modulation of the activity of the NF-kB signalling pathway through a role in histone phosphorylation or acetylation, or through reduction of transcription competence of the NF-kB complex [Saccini, S. Nature Immunol., 3: 69-75, (2002); Carter, A B et al J Biol Chem 274: 30858-63 (1999)]. Finally, a role for p38 in generation of response to IFNs through activation by the Type I IFN receptor has been described [Platanias, Pharmacol. Therap. 98:129-142 (2003)]. Activation of p38 is involved in the transcriptional regulation of IFN sensitive genes through modification of specific transcription factors binding to promotor elements in these genes. Direct phosphorylation of STATs by p38 has not been conclusively demonstrated.

In addition to inhibiting IL-1 and TNF upregulation in response to inflammatory stimuli, p38 kinase inhibitors (e.g., SK&F 86002 and SB-203580) are effective in a number of different cell types in decreasing the synthesis of a wide variety of pro-inflammatory proteins including, IL-6, IL-8, GM-CSF, RANTES and COX-2. Inhibitors of p38 kinase have also been shown to suppress the TNF-induced expression of VCAM-1 on endothelial cells, the TNF-induced phosphorylation and activation of cytosolic PLA2 and the IL-1-stimulated synthesis of collagenase and stromelysin. These and additional data demonstrate that p38 is involved not only cytokine synthesis in response to stress, but also in propagating the consequent cytokine signaling [CSBP/P38 kinase reviewed in Cohen, P. *Trends Cell Biol.,* 353-361(1997)].

Interleukin-1 (IL-1) and Tumor Necrosis Factor (TNF) are important inflammatory cytokines produced by a variety of cells, such as monocytes, macrophages, and smooth muscle cells. IL-1 has been demonstrated to mediate a variety of biological activities thought to be important in immunoregulation and other physiological conditions such as inflammation [See, e.g., Dinarello et al., Rev. Infect. Disease, 6, 51 (1984)]. The myriad of known biological activities of IL-1 include the activation of T helper cells, induction of fever, stimulation of prostaglandin or collagenase production, neutrophil chemotaxis, induction of acute phase proteins and the suppression of plasma iron levels.

There are many disease states in which excessive or unregulated IL-1 production is implicated in exacerbating and/or causing the disease. These include rheumatoid arthritis, osteoarthritis, endotoxemia and/or toxic shock syndrome, other acute or chronic inflammatory disease states such as the inflammatory reaction induced by endotoxin or inflammatory bowel disease; tuberculosis, atherosclerosis, muscle degeneration, cachexia, psoriatic arthritis, Reiter's syndrome, rheumatoid arthritis, gout, traumatic arthritis, rubella arthritis, and acute synovitis. Evidence also links IL-1 activity to diabetes and pancreatic β cells [review of the biological activities which have been attributed to IL-1 Dinarello, *J. Clinical Immunology,* 5 (5), 287-297 (1985)].

Excessive or unregulated TNF production has been implicated in mediating or exacerbating a number of diseases including rheumatoid arthritis, rheumatoid spondylitis, osteoarthritis, gouty arthritis and other arthritic conditions; sepsis, septic shock, endotoxic shock, gram negative sepsis, toxic shock syndrome, adult respiratory distress syndrome, cerebral malaria, chronic obstructive pulmonary disease, silicosis, pulmonary sarcoisosis, bone resorption diseases, reperfusion injury, graft vs. host reaction, allograft rejections, fever and myalgias due to infection, such as influenza, cachexia secondary to infection or malignancy, cachexia, secondary to acquired immune deficiency syndrome (AIDS), AIDS, ARC (AIDS related complex), keloid formation, scar tissue formation, Crohn's disease, ulcerative colitis, or pyresis.

Inflammatory diseases are also marked by increases in IL-6 and C-reactive protein (CRP), both of which are sensitive to inhibition by p38 inhibitors. IL-6 stimulation of CRP production is directly inhibited by p38 inhibitors in human vascular endothelial cells, and CRP is produced by hepatocytes in response to IL-6. CRP is considered a major risk factor for cardiovascular disease [Circulation 2003.107: 363-369] and may be a significant independent risk factor for chronic obstructive pulmonary disease [Circulation 2003. 107:1514-1519]. IL-6 is also upregulated in endometriosis [Bedaiwy et al., 2002, Human Reproduction 17:426-431; Witz, 2000, Fertility and Sterility 73: 212-214].

Interleukin-8 (IL-8) and RANTES are chemotactic factors produced by several cell types including mononuclear cells, fibroblasts, endothelial cells, epithelial cells, neutrophils and T cells. Chemokine production is induced by pro-inflammatory stimuli such as IL-1, TNF, or lipopolysachharide (LPS), or viral infection. IL-8 stimulates a number of functions in vitro. It has been shown to have chemoattractant properties for neutrophils, T-lymphocytes, and basophils. In addition it induces histamine release from basophils from both normal and atopic individuals as well as lysozomal enzyme release and respiratory burst from neutrophils. IL-8 has also been shown to increase the surface expression of Mac-1 (CD11b/CD18) on neutrophils without de novo protein synthesis, which may contribute to increased adhesion of the neutrophils to vascular endothelial cells. Many diseases are characterized by massive neutrophil infiltration. Conditions such as chronic obstructive pulmonary disease associated with an increase in IL-8 production would benefit by compounds which are suppressive of IL-8 production. RANTES is produced by cells such as epithelial cells and airway smooth muscle in response to infection or cytokine stimulation. Its main chemoattraction is for T cell subtypes and blood-borne monocytes.

IL-1, TNF and other cytokines affect a wide variety of cells and tissues and these cytokines as well as other leukocyte derived cytokines are important as critical inflammatory mediators of a wide variety of disease states and conditions. The inhibition of these cytokines is of benefit in controlling, reducing and alleviating many of these disease states.

In addition to the involvement of p38 signaling in the production of IL-1, TNF, IL-8, IL-6, GM-CSF, COX-2, collagenase and stromelysin, signal transduction via CSBP/p38 is required for the effector functions of several of these same pro-inflammatory proteins plus many others. For example, growth factors such as VEGF, PDGF, NGF signal through surface receptors which in turn activate cellular signaling pathways including p38 MAPK [Ono, K. and Han, J., *Cellular Signalling,* 12 1-13 (2000); Kyriakis, J M and Avruch, J. *Physiol Rev* 81: 807-869 (2001)]. TGF□, a key molecule in the control of inflammatory response, also activates p38 as a consequence of engagement of the TGF□ receptor. The involvement of CSBP/p38 in multiple stress-induced signal transduction pathways provides additional rationale for the potential utility of CSBP/p38 in the treatment of diseases resulting from the excessive and destructive activation of the immune system, or chronic inflammation. This expectation is supported by the potent and diverse activities described for CSBP/p38 kinase inhibitors [Badger, et al., *J. Pharm. Exp. Thera.* 279 (3): 1453-1461.(1996); Griswold, et al, *Pharmacol. Comm.* 7, 323-229 (1996); Jackson, et al., J. Pharmacol. Exp. Ther. 284, 687-692 (1998); Underwood, et al., J. Pharmacol. Exp. Ther. 293, 281-288 (2000); Badger, et al., Arthritis Rheum. 43, 175-183 (2000)].

Chronic inflammation is also characterized by ongoing remodeling and repair of affected tissue, leading in some cases to excess fibrotic tissue. A role for p38 MAPK in fibrosis is supported by findings that this enzyme mediates signaling of transforming growth factor beta (TGF-β) on markers and proteins of fibrosis. For example, it has been shown that TGF-β increases the kinase activity of p38 MAPK through the TGF-β activated kinase TAK-1 (Hanafusa et al., 1999, J. Biol. Chem. 274:27161-27167). Furthermore, the p38 inhibitor SB-242235 inhibited the TGF-β-induced increases in fibronectin and thrombospondin (Laping et al., 2002, Molec. Pharmacol. 62:58-64). These results show that p38 MAPK is a key signaling intermediate for the effect of the pro-fibrotic cytokine TGF-β on components of the extracellular matrix and markers of fibrosis.

P38 also plays a role in directing survival and apoptosis of cells in response to various stimuli. Both survival and apoptosis can be p38 regulated depending on the stimulus and the cell type [Morin and Huot, *Cancer Research.* 64:1893-1898 (2004)]. For example, TGF-beta can stimulate apoptosis in murine hepatocytes through activation of gadd45b, a protein involved in cell-cycle control, in a p38 mediated process [Yoo et al, J. Biol. Chem. 278:43001-43007, (2003)]. In a different response pathway, UV-stress can activate p38 and trigger apoptosis of a damaged cell. P38 has also been shown to promote survival of lymphocytes in response to stress, including neutrophils and CD8+ T cells.

There remains a need for treatment, in this field, for compounds which are cytokine suppressive anti-inflammatory drugs, i.e. compounds which are capable of inhibiting the CSBP/p38/RK kinase. The present invention is directed to such novel compounds which are inhibitors of p38 kinase.

SUMMARY OF THE INVENTION

This invention relates to the novel compounds, and their pharmaceutically acceptable salts thereof of Formulas (I), (Ia), (II) or (IIa), and pharmaceutical compositions comprising a compound of Formulas (I), (Ia), (II) or (IIa), and pharmaceutically acceptable salts thereof, and a pharmaceutically acceptable diluent or carrier.

This invention relates to a method of treating the inflammatory component of a CSBP/RK/p38 kinase mediated disease in a mammal in need thereof, which comprises administering to said mammal an effective amount of a compound of Formula (I) or (II).

This invention also relates to a method of inhibiting cytokines and the treatment of inflammation associated with a cytokine mediated disease, in a mammal in need thereof, which comprises administering to said mammal an effective amount of a compound of Formulas (I), (Ia), (II) or (IIa).

This invention more specifically relates to a method of inhibiting the production of IL-1 in a mammal in need thereof which comprises administering to said mammal an effective amount of a compound of Formulas (I), (Ia), (II) or (IIa).

This invention more specifically relates to a method of inhibiting the production of IL-6 in a mammal in need thereof which comprises administering to said mammal an effective amount of a compound of Formulas (I), (Ia), (II) or (IIa).

This invention more specifically relates to a method of inhibiting the production of IL-8 in a mammal in need thereof which comprises administering to said mammal an effective amount of a compound of Formulas (I), (Ia), (II) or (IIa).

This invention more specifically relates to a method of inhibiting the production of TNF in a mammal in need thereof which comprises administering to said mammal an effective amount of a compound of Formulas (I), (Ia), (II) or (IIa).

Compounds of Formula (I) and (Ia) are represented by the formula:

wherein $R_1$ is an optionally substituted aryl or an optionally substituted heteroaryl ring;

$R_2$ and $R_{2'}$ are independently selected from hydrogen, $C_{1-10}$ alkyl, $C_{3-7}$ cycloalkyl, $C_{3-7}$ cycloalkyl$C_{1-10}$ alkyl, $C_{5-7}$ cycloalkenyl, $C_{5-7}$ cycloalkenyl-$C_{1-10}$ alkyl, aryl, aryl$C_{1-10}$ alkyl, heteroaryl, heteroaryl$C_{1-10}$ alkyl, heterocyclic, or a heterocyclyl$C_{1-10}$ alkyl moiety, wherein all of the moieties are optionally substituted, or $R_2$ and $R_{2'}$ together with the nitrogen to which they are attached form a 5 to 7 membered optionally substituted ring, which ring may contain an additional heteroatom selected from oxygen, nitrogen or sulfur;

$R_a$ is hydrogen, or an optionally substituted $C_{1-4}$ alkyl;

$R_g$ is selected from an optionally substituted $C_{1-10}$ alkyl, —CH$_2$—CH$_2$—O—CH$_2$—CH$_2$—, —CH$_2$—C(O)—CH$_2$, CH$_2$—C(O)N(R$_{12}$)CH$_2$—CH$_2$—, CH$_2$—N(R$_{12}$)C(O)CH$_2$—, CH$_2$—CH(OR$_{12}$)—CH$_2$, CH$_2$—C(O)O—CH$_2$—CH$_2$, or CH$_2$—CH$_2$—O—C(O)CH$_2$—;

$R_{12}$ is hydrogen, or an optionally substituted $C_{1-4}$ alkyl;

$R_3$ is an $C_{1-10}$ alkyl, $C_{3-7}$ cycloalkyl, $C_{3-7}$ cycloalkyl$C_{1-4}$ alkyl, aryl, aryl$C_{1-10}$ alkyl, heteroaryl, heteroaryl$C_{1-10}$ alkyl, heterocyclic, or a heterocyclyl$C_{1-10}$ alkyl moiety, which moieties are all optionally substituted;

the dotted line is an optional double bond; and a pharmaceutically acceptable salt, solvate or physiologically functional derivative thereof.

DETAILED DESCRIPTION OF THE INVENTION

The novel compound of Formulas (I), (Ia), (II) or (IIa), are discussed in greater detail described below.

The present invention is directed to novel compounds of Formulas (I), (Ia), (II) or (IIa), or a pharmaceutically acceptable salt, solvate or physiologically functional derivative thereof.

Compounds of Formula (I) are further represented by the formula:

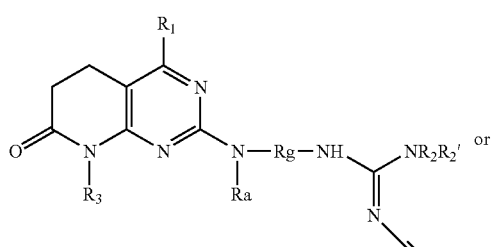
(I)

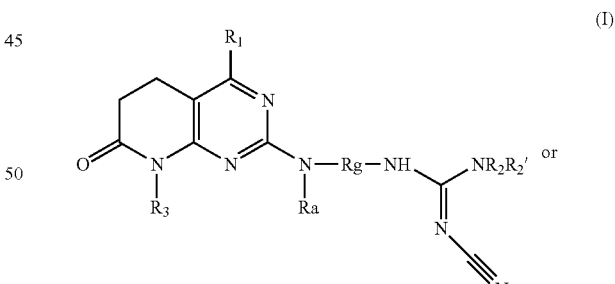
(I)

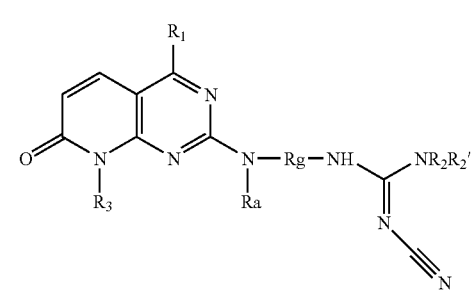
(Ia)

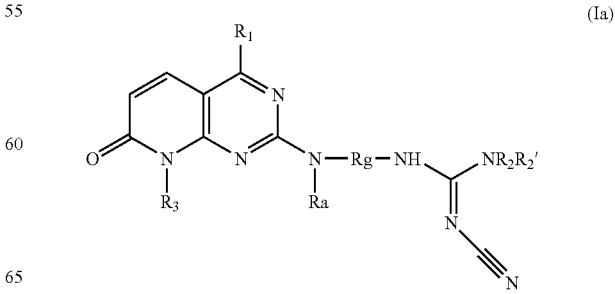
(Ia)

wherein $R_1$ is an optionally substituted aryl ring or an optionally substituted heteroaryl ring, which ring is substituted independently at each occurrence one or more times by halogen, $C_{1-4}$ alkyl, halo-substituted-$C_{1-4}$ alkyl, hydroxy, cyano, nitro, $(CR_{10}R_{20})_v NR_4R_{14}$, $(CR_{10}R_{20})_v C(Z)NR_4R_{14}$, $(CR_{10}R_{20})_v C(Z)OR_8$, $(CR_{10}R_{20})_v COR_c$, $(CR_{10}R_{20})_v C(O)H$, $SR_5$, $S(O)R_5$, $S(O)_2R_5$, $(CR_{10}R_{20})_v OR_8$, $ZC(Z)R_{11}$, $N(R_{10'})C(Z)R_{11}$, $N(R_{10'})S(O)_2R_7$; $C(Z)N(R_{10'})(CR_{10}R_{20})_v R_b$, $C(Z)O(CR_{10}R_{20})_v R_b$, $N(R_{10'})C(Z)(CR_{10}R_{20})_v R_b$; $N(R_{10'})C(Z)N(R_{10'})(CR_{10}R_{20})_v R_b$; or $N(R_{10'})OC(Z)(CR_{10}R_{20})_v R_b$;

$R_2$ and $R_{2'}$ are independently selected from hydrogen, $C_{1-10}$ alkyl, $C_{3-7}$cycloalkyl, $C_{3-7}$cycloalkyl$C_{1-10}$alkyl, $C_{5-7}$ cycloalkenyl, $C_{5-7}$ cycloalkenyl-$C_{1-10}$alkyl, aryl, aryl$C_{1-10}$ alkyl, heteroaryl, heteroaryl$C_{1-10}$ alkyl, heterocyclic, or a heterocyclyl$C_{1-10}$ alkyl moiety, wherein all of the moieties are optionally substituted, or $R_2$ and $R_{2'}$ together with the nitrogen to which they are attached form a 5 to 7 membered optionally substituted ring, which ring may contain an additional heteroatom selected from oxygen, nitrogen or sulfur; these moieties, excluding hydrogen, may be optionally substituted independently one or more times, by hydrogen, $C_{1-4}$ alkyl, halo-substituted $C_{1-4}$ alkyl, $C_{2-4}$ alkenyl, $C_{2-4}$ alkynyl, $C_{3-7}$ cycloalkyl, $C_{3-7}$ cycloalkyl $C_{1-4}$ alkyl, $C_{5-7}$ cycloalkenyl, $C_{5-7}$cycloalkenyl $C_{1-4}$ alkyl, aryl, aryl$C_{1-4}$ alkyl, heteroaryl, heteroaryl$C_{1-4}$ alkyl, heterocyclyl, or a heterocyclyl$C_{1-4}$ alkyl moiety, and wherein these moieties, excluding hydrogen, may be optionally substituted 1 to 4 times by halogen; halosubstituted $C_{1-4}$ alkyl; $C_{1-4}$ alkyl; $C_{3-5}$cycloalkyl; $C_{3-5}$cycloalkyl $C_{1-4}$alkyl; halosubstituted $C_{1-4}$ alkyl; hydroxy; hydroxy substituted $C_{1-4}$alkyl; $C_{1-4}$alkoxy; halosubstituted $C_{1-4}$ alkoxy; $S(O)_m C_{1-4}$ alkyl; —C(O), $C(O)C_{1-4}$alkyl; $NR_4R_{14'}$; or an aryl or arylalkyl, and wherein these aryl containing moieties may also be substituted one to two times by halogen, hydroxy, hydroxy substituted alkyl, $C_{1-4}$ alkoxy, $S(O)_m C_{1-4}$alkyl, amino, mono & di-substituted $C_{1-4}$ alkylamino, $C_{1-4}$ alkyl, or $CF_3$;

$R_3$ is a $C_{1-10}$ alkyl, $C_{3-7}$ cycloalkyl, $C_{3-7}$ cycloalkyl $C_{1-10}$ alkyl, aryl, aryl$C_{1-10}$ alkyl, heteroaryl, heteroaryl$C_{1-10}$ alkyl, heterocyclic, or heterocyclyl$C_{1-10}$ alkyl moiety, and wherein these moieties are all optionally substituted one or more times, independently at each occurrence from hydrogen, halogen, nitro, $C_{1-10}$ alkyl, halo-substituted $C_{1-10}$ alkyl, $C_{2-10}$ alkenyl, $C_{2-10}$alkynyl, $C_{3-7}$cycloalkyl, $C_{3-7}$cycloalkyl$C_{1-10}$ alkyl, $C_{5-7}$cycloalkenyl, $C_{5-7}$cycloalkenyl$C_{1-10}$ alkyl, $(CR_{10}R_{20})_n OR_6$, $(CR_{10}R_{20})_n SH$, $(CR_{10}R_{20})_n S(O)_m R_7$, $(CR_{10}R_{20})_n N(R_{10'})S(O)_2 R_7$, $(CR_{10}R_{20})_n NR_{16}R_{26}$, $(CR_{10}R_{20})_n CN$, $(CR_{10}R_{20})_n S(O)_2 NR_{16}R_{26}$, $(CR_{10}R_{20})_n C(Z)R_6$, $(CR_{10}R_{20})_n OC(Z)R_6$, $(CR_{10}R_{20})_n C(Z)OR_6$, $(CR_{10}R_{20})_n C(Z)NR_{16}R_{26}$, $(CR_{10}R_{20})_n N(R_{10'})C(Z)R_6$, $(CR_{10}R_{20})_n N(R_{10'})C(=N(R_{10'}))NR_{16}R_{26}$, $(CR_{10}R_{20})_n OC(Z)NR_{16}R_{26}$, $(CR_{10}R_{20})_n N(R_{10'})C(Z)NR_{16}R_{26}$, or $(CR_{10}R_{20})_n N(R10')C(Z)OR_7$;

$R_4$ and $R_{14}$ are each independently selected from hydrogen, optionally substituted $C_{1-4}$ alkyl, optionally substituted $C_{3-7}$ cycloalkyl, $C_{3-7}$ cycloalkyl$C_{1-4}$alkyl, optionally substituted aryl, or optionally substituted aryl-$C_{1-4}$ alkyl, heteroaryl, heteroaryl $C_{1-4}$ alkyl, heterocyclic, or heterocyclic $C_{1-4}$ alkyl; or $R_4$ and $R_{14}$ together with the nitrogen which they are attached form an optionally substituted heterocyclic ring of 4 to 7 members, which ring optionally contains an additional heteroatom selected from oxygen, sulfur or nitrogen; and wherein the $C_{1-10}$ alkyl, $C_{3-7}$cycloalkyl, $C_{3-7}$cycloalkyl$C_{1-4}$ alkyl, aryl, aryl-$C_{1-4}$ alkyl, heteroaryl and heteroaryl $C_{1-4}$ alkyl moieties, and the $R_4$ and $R_{14}$ cyclized ring are optionally substituted, 1 to 4 times, independently at each occurrence, by halogen; hydroxy; hydroxy substituted $C_{1-10}$alkyl; $C_{1-10}$ alkoxy; halosubstituted $C_{1-10}$ alkoxy; $C_{1-10}$ alkyl; halosubstituted $C_{1-10}$ alkyl; $SR_5$; $S(O)R_5$; $S(O)_2R_5$; $C(O)R_j$; $C(O)OR_j$; $C(O)NR_4R_{14'}$; $(CR_{10}R_{20})_n N(R_{10'})C(Z)OR_7$; $(CR_{10}R_{20})_n N(R_{10'})C(Z)NR_4R_{d'}$; $NR_4C(O)C_{1-10}$alkyl; $NR_4C(O)$aryl; $NR_4R_{14'}$; cyano; nitro; $C_{3-7}$cycloalkyl; $C_{3-7}$cycloalkyl $C_{1-10}$ alkyl; $C_{1-10}$ alkyl substituted one or more times by an optionally substituted aryl; an unsubstituted or substituted aryl, or aryl$C_{1-4}$ alkyl; an unsubstituted or substituted heteroaryl, or heteroaryl $C_{1-4}$ alkyl; an unsubstituted or substituted heterocyclic, or heterocyclic $C_{1-4}$ alkyl, and wherein these aryl, heterocyclic and heteroaryl containing moieties are substituted one to two times independently at each occurrence by halogen; $C_{1-4}$ alkyl, hydroxy; hydroxy substituted $C_{1-4}$ alkyl; $C_{1-4}$ alkoxy; $S(O)_m$alkyl; amino, mono & di-substituted $C_{1-4}$ alkyl amino, or $CF_3$;

$R_{4'}$ and $R_{14'}$ are each independently selected at each occurrence from hydrogen or $C_{1-4}$ alkyl, or $R_{4'}$ and $R_{14'}$ can cyclize together with the nitrogen to which they are attached to form a 5 to 7 membered ring which optionally contains an additional heteroatom selected from oxygen, sulfur or $NR_9$;

$R_{4''}$ and $R_{14''}$ are independently selected at each occurrence from hydrogen or $C_{1-4}$ alkyl, or $R_{4''}$, and $R_{14''}$ together with the nitrogen to which they are attached, cyclize to form a 5 to 7 membered ring which optionally contains an additional heteroatom selected from oxygen, sulfur or $NR_9$;

$R_5$ is independently selected from hydrogen, $C_{1-4}$ alkyl, $C_{2-4}$ alkenyl, $C_{2-4}$ alkynyl or $NR_4R_{14'}$, excluding the moieties $SR_5$ being $SNR_4R_{14'}$, $S(O)_2R_5$ being $SO_2H$ and $S(O)R_5$ being $SOH$;

$R_7$ is independently selected from $C_{1-6}$alkyl, aryl, aryl$C_{1-6}$ alkyl, heterocyclic, heterocyclyl$C_{1-6}$ alkyl, heteroaryl, or heteroaryl$C_{1-6}$alkyl; and wherein each of these moieties may be optionally substituted;

$R_8$ is independently selected from hydrogen, $C_{1-4}$ alkyl, halo-substituted $C_{1-4}$ alkyl, $C_{2-4}$ alkenyl, $C_{2-4}$ alkynyl, $C_{3-7}$ cycloalkyl, $C_{5-7}$ cycloalkenyl, aryl, aryl$C_{1-4}$ alkyl, heteroaryl, heteroaryl$C_{1-4}$ alkyl, heterocyclyl, heterocyclyl$C_{1-4}$ alkyl, $(CR_{10}R_{20})_t OR_7$, $(CR_{10}R_{20})_t S(O)_m R_7$, $(CR_{10}R_{20})_t N(R_{10'})S(O)_2R_7$, or $(CR_{10}R_{20})_t NR_4R_{14'}$; and wherein the cycloalkyl, cycloalkenyl, aryl, arylalkyl, heteroaryl, heteroaryl alkyl, heterocyclic and heterocyclic alkyl moieties may be optionally substituted independently;

$R_9$ is independently selected at each occurrence from hydrogen, $C(Z)R_6$, optionally substituted $C_{1-10}$ alkyl, optionally substituted aryl, optionally substituted aryl-$C_{1-4}$ alkyl;

$R_{9'}$ is independently selected from hydrogen, or $C_{1-4}$ alkyl.

$R_{10}$ and $R_{20}$ are independently selected at each occurrence from hydrogen or $C_{1-4}$alkyl;

$R_{10'}$ is independently selected at each occurrence from hydrogen or $C_{1-4}$alkyl;

$R_{11}$ is $C_{1-4}$ alkyl, halo-substituted $C_{1-4}$ alkyl, $C_{2-4}$ alkenyl, $C_{2-4}$ alkynyl, $C_{3-7}$ cycloalkyl, $C_{5-7}$ cycloalkenyl, aryl, aryl$C_{1-4}$ alkyl, heteroaryl, heteroaryl$C_{1-4}$ alkyl, heterocyclyl, heterocyclyl$C_{1-4}$ alkyl, $(CR_{10}R_{20})_tOR_7$, $(CR_{10}R_{20})_tS(O)_mR_7$, $(CR_{10}R_{20})_t$ $N(R_{10'})S(O)_2R_7$, or $(CR_{10}R_{20})_v$ $NR_4R_{14}$; and wherein the aryl, arylalkyl, heteroaryl, heteroaryl alkyl, heterocyclyl, and heterocyclylalkyl moieties may be optionally substituted;

$R_{12}$ is hydrogen, or an optionally substituted $C_{1-4}$ alkyl; $R_{16}$ and $R_{26}$ are each independently selected at each occurrence from hydrogen, or $C_{1-4}$ alkyl; or the $R_{16}$ and $R_{26}$ together with the nitrogen which they are attached form an unsubstituted or substituted heterocyclic ring of 4 to 7 members, which ring optionally contains an additional heteroatom selected from oxygen, sulfur or $NR_9$;

$R_{16}$ and $R_{26}$ are each independently selected at each occurrence from hydrogen, or $C_{1-4}$ alkyl; or the $R_{16}$ and $R_{26}$ together with the nitrogen which they are attached form an unsubstituted or substituted heterocyclic ring of 4 to 7 members, which ring optionally contains an additional heteroatom selected from oxygen, sulfur or $NR_9$;

$R_{18}$ and $R_{28}$ are each independently selected at each occurrence from hydrogen, $C_{1-4}$ alkyl, $C_{3-7}$ cycloalkyl, $C_{3-7}$ cycloalkyl$C_{1-4}$alkyl, aryl, or aryl-$C_{1-4}$ alkyl, heteroaryl or heteroaryl $C_{1-4}$ alkyl moiety, and wherein these moieties, excluding hydrogen may be optionally substituted; or $R_{18}$ and $R_{28}$ together with the nitrogen which they are attached form an optionally substituted heterocyclic ring of 4 to 7 members, which ring optionally contains an additional heteroatom selected from oxygen, sulfur or $NR_{9'''}$; and wherein these moieties are optionally substituted 1 to 4 times, independently by halogen; hydroxy; hydroxy substituted $C_{1-10}$alkyl; $C_{1-10}$ alkoxy; halosubstituted $C_{1-10}$ alkoxy; $C_{1-4}$ alkyl; halosubstituted $C_{1-4}$ alkyl; $SR_5$, $S(O)R_5$, $S(O)_2R_5$; $C(O)R_j$; $C(O)OR_j$; $C(O)NR_4R_{14'}$; $NR_4C(O)C_{1-10}$alkyl; $NR_4C(O)$aryl; $NR_4R_{14'}$; cyano; nitro; $C_{1-10}$ alkyl; $C_{3-7}$cycloalkyl; $C_{3-7}$cycloalkyl $C_{1-10}$ alkyl; halosubstituted $C_{1-10}$ alkyl; aryl, aryl $C_{1-4}$ alkyl, heteroaryl, or hetero $C_{1-4}$ alkyl, and wherein these aryl or heteroaryl containing moieties may also be substituted one to two times independently by halogen, $C_{1-4}$ alkyl, hydroxy, hydroxy substituted $C_{1-4}$ alkyl, $C_{1-10}$ alkoxy, $S(O)_m$alkyl, amino, mono & di-substituted $C_{1-4}$ alkyl amino, $C_{1-4}$ alkyl, or $CF_3$;

$R_a$ is hydrogen, or an optionally substituted $C_{1-4}$ alkyl;

$R_b$ is hydrogen, $C_{1-10}$ alkyl, $C_{3-7}$ cycloalkyl, $C_{3-7}$ cycloalkyl$C_{1-10}$ alkyl, aryl, aryl$C_{1-10}$alkyl, heteroaryl, heteroaryl$C_{1-10}$ alkyl, heterocyclic, or a heterocyclyl$C_{1-10}$ alkyl moiety, which moieties, excluding hydrogen, are all optionally substituted, one or more times, independently at each occurrence by halogen; hydroxy; hydroxy substituted $C_{1-10}$alkyl; $C_{1-10}$ alkoxy; halosubstituted $C_{1-10}$ alkoxy; $OR_8$; $SR_5$, $S(O)R_5$, $S(O)_2R_5$; $C(O)R_j$; $C(O)OR_j$; $C(O)NR_{4''}R_{14'}$; cyano; nitro; $NR_{18}R_{28}$; -Z'-$(CR_{10}R_{20})$s-Z'; $C_{1-10}$alkyl; $C_{3-7}$cycloalkyl; $C_{3-7}$cycloalkyl $C_{1-10}$ alkyl; halosubstituted $C_{1-10}$ alkyl; optionally substituted aryl or aryl $C_{1-10}$alkyl; optionally substituted heterocyclic or heterocyclic $C_{1-10}$alkyl; or optionally substituted heteroaryl or heteroaryl $C_{1-10}$alkyl, and wherein these aryl, heteroaryl, and heterocyclic containing moieties may also be substituted one to two times independently at each occurrence by halogen, hydroxy, hydroxy substituted $C_{1-4}$ alkyl, $C_{1-10}$ alkoxy, $S(O)_m$alkyl, amino, mono & di-substituted $C_{1-4}$ alkyl amino, $C_{1-4}$ alkyl, or $CF_3$;

$R_c$ is $C_{1-4}$ alkyl, halo-substituted $C_{1-4}$ alkyl, $C_{2-4}$ alkenyl, $C_{2-4}$ alkynyl, $C_{3-7}$ cycloalkyl, $C_{5-7}$ cycloalkenyl, aryl, aryl$C_{1-4}$ alkyl, heteroaryl, heteroaryl$C_{1-4}$ alkyl, heterocyclyl, heterocyclyl$C_{1-4}$ alkyl, $(CR_{10}R_{20})_vOR_7$, $(CR_{10}R_{20})_vS(O)_mR_7$, $(CR_{10}R_{20})_v$ $N(R_{10'})S(O)_2R_7$, or $(CR_{10}R_{20})_vNR_4R_{14}$; and wherein the alkyl, cycloalkyl, cycloalkenyl, aryl, arylalkyl, heteroaryl, heteroaryl alkyl, heterocyclic and heterocyclic alkyl moieties may be optionally substituted;

$R_d$ and $R_{d'}$ are each independently selected at each occurrence from hydrogen, $C_{1-4}$ alkyl, $C_{3-6}$ cycloalkyl, $C_{3-6}$ cycloalkyl$C_{1-4}$alkyl, or the $R_d$ and $R_{d'}$ together with the nitrogen which they are attached form an optionally substituted heterocyclic ring of 5 to 6 members, which ring optionally contains an additional heteroatom selected from oxygen, sulfur or $NR_9$; and wherein the $R_d$ and $R_{d'}$ moieties which are $C_{1-4}$ alkyl, $C_{3-6}$cycloalkyl, $C_{3-6}$cycloalkyl$C_{1-4}$ alkyl, and the $R_d$ and $R_{d'}$ cyclized ring are substituted, 1 to 4 times, independently at each occurrence by halogen; halosubstituted $C_{1-4}$ alkyl; hydroxy; hydroxy substituted $C_{1-4}$alkyl; $C_{1-4}$ alkoxy; halosubstituted $C_{1-4}$ alkoxy; S(O)mRf; C(O)Rj; C(O)ORj; C(O)NR$_4$R$_{14'}$; NR$_4$C(O)C$_{1-4}$alkyl; S(O)$_2$NR$_4$R$_{14}$C$_{1-4}$ alkyl; NR$_4$R$_{14}$S(O)$_2$C$_{1-4}$ alkyl; or NR$_4$R$_{14}$;

$R_f$ is independently selected at each occurrence from $C_{1-10}$alkyl, aryl, aryl $C_{1-10}$alkyl, heteroaryl, heteroaryl $C_{1-10}$alkyl, heterocyclic, or a heterocyclic $C_{1-10}$alkyl moiety, and wherein these moieties may all be optionally substituted;

$R_j$ is independently selected at each occurrence from hydrogen, $C_{1-4}$alkyl, aryl, aryl $C_{1-4}$alkyl, heteroaryl, heteroaryl $C_{1-4}$alkyl, heterocyclic, or a heterocyclic $C_{1-4}$alkyl moiety, and wherein these moieties, excluding hydrogen, may be optionally substituted;

$R_g$ is selected from an optionally substituted $C_{1-10}$ alkyl, —CH$_2$—CH$_2$—O—CH$_2$—CH$_2$—, —CH$_2$—C(O)—CH$_2$, CH$_2$—C(O)N(R$_{12}$)CH$_2$—CH$_2$—, CH$_2$—N(R$_{12}$)C(O)CH$_2$—, CH$_2$—CH(OR$_{12}$)—CH$_2$, CH$_2$—C(O)O—CH$_2$—CH$_2$, or CH$_2$—CH$_2$—O—C(O)CH$_2$—;

v is 0 or an integer having a value of 1 or 2;

n is independently selected at each occurrence from 0 or an integer having a value of 1 to 10;

n' is independently selected at each occurrence from 0, or an integer having a value of 1 to 10;

m is independently selected at each occurrence from 0 or an integer having a value of 1 or 2;

s is an integer having a value of 1, 2, or 3, independently selected at each occurrence;

t is independently selected at each occurrence from an integer having a value of 1 to 3;

Z is independently selected at each occurrence from oxygen or sulfur;

the dotted line is an optional double bond; and a pharmaceutically acceptable salt, solvate or physiologically functional derivative thereof.

Another aspect of the present invention are compounds represented by the formula:

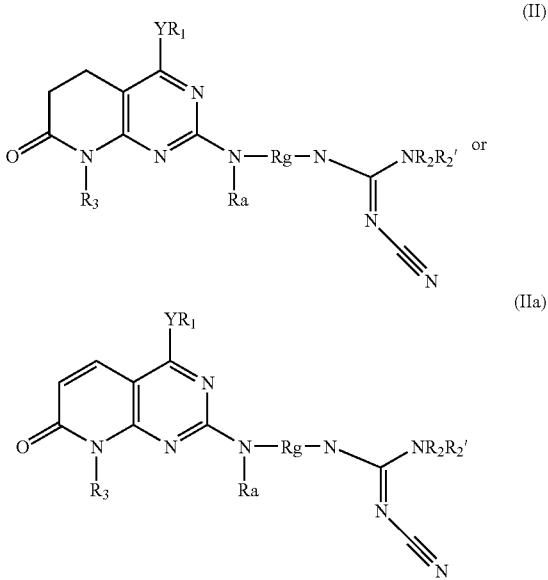

wherein

R₁ is an optionally substituted aryl or an optionally substituted heteroaryl ring;

Y is C(R$_{13'}$)(R$_{16'}$), C(O), N(R$_{16}$), N(R$_{17'}$)C(R$_{15'}$)(R$_{16'}$), oxygen, OC(R$_{15'}$)(R$_{16'}$), S(O)m, or S(O)$_m$C(R$_{15'}$)(R$_{16'}$);

R$_{13'}$ is hydrogen, C$_{1-2}$ alkyl, N(R$_{18'}$)$_2$, hydroxy, thio, C$_{1-2}$ alkoxy, or S(O)$_m$C$_{1-2}$alkyl;

R$_{15'}$ is hydrogen or C$_{1-2}$ alkyl;

R$_{16'}$ is hydrogen or C$_{1-2}$ alkyl;

R$_{17'}$ is hydrogen or C$_{1-2}$ alkyl;

R$_{18'}$ is independently selected at each occurrence from hydrogen or C$_{1-2}$ alkyl;

m is independently selected at each occurrence from 0 or an integer having a value of 1 or 2;

R$_2$ and R$_{2'}$ are independently selected from hydrogen, C$_{1-10}$ alkyl, C$_{3-7}$cycloalkyl, C$_{3-7}$cycloalkylC$_{1-10}$alkyl, C$_{5-7}$ cycloalkenyl, C$_{5-7}$ cycloalkenyl-C$_{1-10}$alkyl, aryl, aryl C$_{1-10}$ alkyl, heteroaryl, heteroarylC$_{1-10}$ alkyl, heterocyclic, or a heterocyclylC$_{1-10}$ alkyl moiety, wherein all of the moieties are optionally substituted, or R$_2$ and R$_{2'}$ together with the nitrogen to which they are attached form a 5 to 7 membered optionally substituted ring, which ring may contain an additional heteroatom selected from oxygen, nitrogen or sulfur;

R$_3$ is an C$_{1-10}$ alkyl, C$_{3-7}$ cycloalkyl, C$_{3-7}$ cycloalkyl C$_{1-4}$alkyl, aryl, arylC$_{1-10}$ alkyl, heteroaryl, heteroarylC$_{1-10}$ alkyl, heterocyclic, or a heterocyclylC$_{1-10}$ alkyl moiety, which moieties are all optionally substituted;

R$_a$ is hydrogen, or an optionally substituted C$_{1-4}$ alkyl;

R$_g$ is selected from an optionally substituted C$_{1-10}$ alkyl, —CH$_2$—CH$_2$—O—CH$_2$—CH$_2$—, —CH$_2$—C(O)—CH$_2$, CH$_2$—C(O)N(R$_{12}$)CH$_2$—CH$_2$—, CH$_2$—N(R$_{12}$)C(O)CH$_2$—, —CH$_2$—CH(OR$_{12}$)—CH$_2$, CH$_2$—C(O)O—CH$_2$—CH$_2$, or CH$_2$—CH$_2$—O—C(O)CH$_2$—;

R$_{12}$ is hydrogen, or an optionally substituted C$_{1-4}$ alkyl;

the dotted line is an optional double bond; and a pharmaceutically acceptable salt, solvate or physiologically functional derivative thereof.

The present invention is directed to novel compounds of Formula (I), (Ia), (II), and Formula (II), or a pharmaceutically acceptable salt, solvate or physiologically functional derivative thereof. As will be readily recognized, the difference between compounds of Formula (I) and that of Formula (II) lies in the R$_1$ moiety that contains the linker Y. The difference between compounds of Formula (I) and (Ia) and (II) and (IIa) respectively lies in the unsaturation in the fused ring. The respective R$_1$, R$_2$, and R$_3$ terms are the same for both groups. For purposes herein, everything applicable to Formula (I) is also applicable to Formula (Ia), and to (II) and (IIa) unless otherwise indicated.

Suitably, for compounds of Formula (I), R$_1$ is an aryl, or heteroaryl ring which may be optionally substituted one or more times, preferably 1 to 4 times, independently by substituents selected from halogen, C$_{1-4}$ alkyl, halo-substituted-C$_{1-4}$ alkyl, hydroxy, cyano, nitro, (CR$_{10}$R$_{20}$)$_v$NR$_4$R$_{14}$, (CR$_{10}$R$_{20}$)$_v$C(Z)NR$_4$R$_{14}$, (CR$_{10}$R$_{20}$)$_v$C(Z)OR$_8$, (CR$_{10}$R$_{20}$)$_v$CORc, (CR$_{10}$R$_{20}$)$_v$C(O)H, SR$_5$, S(O)R$_5$, S(O)$_2$R$_5$, (CR$_{10}$R$_{20}$)$_v$OR$_8$, ZC(Z)R$_{11}$, N(R$_{10'}$)C(Z)R$_{11}$, N(R$_{10'}$)S(O)$_2$R$_7$; C(Z)N(R$_{10'}$)(CR$_{10}$R$_{20}$)$_v$R$_b$, C(Z)O(CR$_{10}$R$_{20}$)$_v$R$_b$, N(R$_{10'}$)C(Z)(CR$_{10}$R$_{20}$)$_v$R$_b$, N(R$_{10'}$)C(Z)N(R$_{10'}$)(CR$_{10}$R$_{20}$)$_v$R$_b$, or N(R$_{10'}$)OC(Z)(CR$_{10}$R$_{20}$)$_v$R$_b$.

In one embodiment of the present invention, R$_1$ is an aryl moiety, such as a phenyl ring or a naphthyl ring, which ring is optionally substituted one or more times, preferably 1 to 4 times, independently at each occurrence, by halogen, C$_{1-4}$ alkyl, (CR$_{10}$R$_{20}$)$_v$OR$_8$, (CR$_{10}$R$_{20}$)$_v$NR$_4$R$_{14}$, or halo-substituted-C$_{1-4}$ alkyl. Preferably, the ring is a phenyl ring substituted one or more times independently at each occurrence by halogen, C$_{1-4}$ alkyl, hydroxy, amino, alkoxy, or halo-substituted-C$_{1-4}$ alkyl. In another embodiment the phenyl ring is substituted one or more times, independently at each occurrence by halogen, such as fluorine or chlorine; C$_{1-4}$ alkyl, such as methyl; or CF$_3$.

Suitably, when R$_1$ is a phenyl ring it is substituted in the 2, 4, or 6-position, or di-substituted in the 2,4-position, such as in 2-fluoro, 4-fluoro, 2,4-difluoro, or 2-methyl-4-fluoro; or tri-substituted in the 2,4,6-position such as 2,4,6-trifluoro.

In another embodiment when R$_1$ is a heteroaryl ring, the ring is not attached to the core pharmacophore via one of its heteroatoms, such as nitrogen to form a charged ring. For instance, a pyridinyl ring would be attached through a carbon atom to yield a 2-, 3- or 4-pyridyl moiety, which moiety may be optionally substituted.

For compounds of Formula (I) and (II), when R$_1$ is an aryl ring, preferably a phenyl ring and the ring is substituted in the ortho position by a substituent, and a second substituent is also substituted on the ring, then the second substitution is preferably not located on the ring in the other ortho position.

In one embodiment, when the aryl ring is optionally substituted one or more times, and the first substituent is selected from C(Z)N(R$_{10'}$)(CR$_{10}$R$_{20}$)$_v$R$_b$, C(Z)O(CR$_{10}$R$_{20}$)$_v$R$_b$, N(R$_{10'}$)C(Z)(CR$_{10}$R$_{20}$)$_v$R$_b$, N(R$_{10'}$)C(Z)N(R$_{10'}$)(CR$_{10}$R$_{20}$)$_v$R$_b$, or N(R$_{10'}$)OC(Z)(CR$_{10}$R$_{20}$)$_v$R$_b$; then the second substituent is selected from hydrogen, halogen, C$_{1-4}$ alkyl, halosubstituted-C$_{1-4}$ alkyl, cyano, nitro, (CR$_{10}$R$_{20}$)$_v$NR$_d$R$_{d'}$, (CR$_{10}$R$_{20}$)$_v$C(O)R$_{12}$, SR$_5$, S(O)R$_5$, S(O)$_2$R$_5$, or (CR$_{10}$R$_{20}$)$_{v'}$OR$_{22}$. In a further embodiment, the second substituent is independently selected at each occurrence from hydrogen, halogen, C$_{1-4}$ alkyl, or halo-substituted-C$_{1-4}$ alkyl.

Suitably, R$_c$ is C$_{1-4}$ alkyl, halo-substituted C$_{1-4}$ alkyl, C$_{2-4}$ alkenyl, C$_{2-4}$ alkynyl, C$_{3-7}$ cycloalkyl, C$_{5-7}$ cycloalkenyl, aryl, arylC$_{1-4}$ alkyl, heteroaryl, heteroarylC$_{1-4}$ alkyl, heterocyclyl, heterocyclylC$_{1-4}$ alkyl, (CR$_{10}$R$_{20}$)$_v$OR$_7$, (CR$_{10}$R$_{20}$)$_v$S(O)$_m$R$_7$, (CR$_{10}$R$_{20}$)$_v$N(R$_{10'}$)S(O)$_2$R$_7$, or (CR$_{10}$R$_{20}$)$_v$NR$_4$R$_{14}$; and wherein the alkyl, cycloalkyl, cycloalkenyl, aryl, arylalkyl, heteroaryl, heteroaryl alkyl, heterocyclic and heterocyclic alkyl moieties may be optionally substituted independently at each occurrence, one or more times, suitably 1 to 4 times.

Suitably, v is 0 or an integer having a value of 1 or 2.

Suitably, v' is 0 or an integer having a value of 1 or 2.

Suitably, $R_{22}$ is independently selected from hydrogen, $C_{1-4}$ alkyl, halo-substituted $C_{1-4}$ alkyl, $C_{2-4}$ alkenyl, $C_{2-4}$ alkynyl, $C_{3-7}$ cycloalkyl, $C_{3-7}$cycloalkyl$C_{1-4}$ alkyl, $C_{5-7}$ cycloalkenyl, $C_{5-7}$cycloalkenyl $C_{1-4}$ alkyl, aryl, aryl$C_{1-4}$ alkyl, heteroaryl, heteroaryl$C_{1-4}$ alkyl, heterocyclyl, or a heterocyclyl$C_{1-4}$ alkyl moiety, and wherein each of these moieties, excluding hydrogen, may be optionally substituted and wherein these moieties, excluding hydrogen, may be optionally substituted 1 to 4 times by halogen; halosubstituted $C_{1-4}$ alkyl; $C_{1-4}$ alkyl; hydroxy; hydroxy substituted $C_{1-4}$alkyl; $C_{1-4}$alkoxy; halosubstituted $C_{1-4}$ alkoxy; S(O)m$C_{1-4}$ alkyl; —C(O), C(O)$C_{1-4}$ alkyl; or $NR_{21}R_{31}$.

Suitably, $R_d$ and $R_{d'}$ are each independently selected from hydrogen, $C_{1-4}$ alkyl, $C_{3-5}$ cycloalkyl, $C_{3-5}$ cycloalkyl$C_{1-4}$ alkyl, or the $R_d$ and $R_{d'}$ together with the nitrogen which they are attached form an optionally substituted heterocyclic ring of 5 to 6 members, which ring optionally contains an additional heteroatom selected from oxygen, sulfur or $NR_9$, and wherein the $R_d$ and $R_{d'}$ moieties which are $C_{1-4}$ alkyl, $C_{3-6}$cycloalkyl, $C_{3-6}$cycloalkyl$C_{1-4}$ alkyl, and the $R_4$ and $R_{14}$ cyclized ring are optionally substituted, 1 to 4 times, independently by halogen; halosubstituted $C_{1-4}$ alkyl; hydroxy; hydroxy substituted $C_{1-4}$alkyl; $C_{1-4}$ alkoxy; halosubstituted $C_{1-4}$ alkoxy; S(O)mRf; C(O)Rj; C(O)ORj; C(O)$NR_{4'}R_{14'}$, $NR_4C(O)C_{1-4}$alkyl; $S(O)_2NR_{4'}R_{14'}C_{1-4}$ alkyl; $NR_{4'}R_{14'}S(O)_2$ $C_{1-4}$ alkyl; or $NR_{4'}R_{14''}$.

Suitably $R_{9'}$ is independently selected from hydrogen, or $C_{1-4}$ alkyl.

Suitably, $R_f$ is hydrogen, $C_{1-10}$alkyl, aryl, aryl $C_{1-10}$alkyl, heteroaryl, heteroaryl $C_{1-10}$alkyl, heterocyclic, or a heterocyclic $C_{1-10}$alkyl moiety, and wherein these moieties, excluding hydrogen, may be optionally substituted.

Suitably, $R_j$ is $C_{1-10}$alkyl, aryl, aryl $C_{1-10}$alkyl, heteroaryl, heteroaryl $C_{1-10}$alkyl, heterocyclic, or a heterocyclic $C_{1-10}$alkyl moiety, which moieties may all be optionally substituted.

In another embodiment, the $R_1$ aryl or heteroaryl ring is optionally substituted is independently at each occurrence by hydrogen, halogen, $C_{1-4}$ alkyl, or halo-substituted-$C_{1-4}$ alkyl. In another embodiment, $R_1$ is optionally substituted independently, at each occurrence by fluorine, chlorine, methyl, or $CF_3$.

Suitably $R_b$ is hydrogen, $C_{1-10}$ alkyl, $C_{3-7}$ cycloalkyl, $C_{3-7}$ cycloalkyl$C_{1-10}$ alkyl, aryl, aryl$C_{1-10}$alkyl, heteroaryl, heteroaryl$C_{1-10}$ alkyl, heterocyclic, or a heterocyclyl$C_{1-10}$ alkyl moiety, which moieties, excluding hydrogen, are all optionally substituted.

The $R_b$ moieties, excluding hydrogen, may be optionally substituted, one or more times, preferably 1 to 4 times independently at each occurrence by halogen, such as fluorine, chlorine, bromine or iodine; hydroxy; hydroxy substituted $C_{1-10}$alkyl; $C_{1-10}$ alkoxy, such as methoxy or ethoxy; halosubstituted $C_{1-10}$ alkoxy; $OR_8$, such as methoxy, ethoxy or phenoxy; $SR_5$, $S(O)R_5$, $S(O)_2R_5$, such as methyl thio, methylsulfinyl or methyl sulfonyl; C(O)$R_j$; C(O)O$R_j$; C(O)$NR_{4'}R_{14''}$; cyano; nitro; $NR_{18}R_{28'}$; -Z'-$(CR_{10}R_{20})$s-Z'; $C_{1-10}$alkyl, $C_{3-7}$cycloalkyl or a $C_{3-7}$cycloalkyl $C_{1-10}$ alkyl group, such as cyclopropyl, or cyclopropyl methyl, or cyclopropyl ethyl, etc.; halosubstituted $C_{1-10}$ alkyl, such $CF_2CF_2H$, $CH_2CF_3$, or $CF_3$; an optionally substituted aryl, such as phenyl, or an optionally substituted aryl $C_{1-10}$alkyl, such as benzyl or phenethyl; an optionally substituted heterocyclic or heterocyclic $C_{1-10}$alkyl, or an optionally substituted heteroaryl or heteroaryl $C_{1-10}$alkyl, and wherein these aryl, heteroaryl, and heterocyclic containing moieties may also be substituted one to two times independently at each occurrence by halogen, hydroxy, hydroxy substituted $C_{1-4}$ alkyl, $C_{1-10}$ alkoxy, S(O)$_m$alkyl, amino, mono & di-substituted $C_{1-4}$ alkyl amino, $C_{1-4}$ alkyl, or $CF_3$.

Suitably, when $R_b$ is an optionally substituted $C_{1-10}$alkyl, the moiety includes but is not limited to a methyl, ethyl, n-propyl, isopropyl, t-butyl, n-butyl, isobutyl, 1,2-dimethylpropyl, 2,2-dimethylpropyl, heptyl, 2-methylpropyl; a halosubstituted alkyl, such as 2,2,2-trifluroethyl, trifluoromethyl, 2-fluoroethyl; a cyano substituted alkyl, such as cyanomethyl, cyanoethyl; an alkoxy, thio or hydroxy substituted alkyl, such as 2-methoxy-ethyl, 2-hydroxy propyl or serinol, or an ethylthioethyl.

In an alternative embodiment, when $R_b$ is an optionally substituted $C_{1-10}$alkyl the moiety is a methyl, ethyl, n-propyl, isopropyl, t-butyl, n-butyl, or 2,2-dimethylpropyl or 2-hydroxy propyl group.

Suitably, when $R_b$ is an optionally substituted heteroaryl, heteroaryl alkyl they are as defined in the definition section, and include but are not limited, to furyl, pyranyl, thienyl, pyrrolyl, oxazolyl, thiazolyl, isoxazolyl, isothiazolyl, imidazolyl, pyrazolyl, oxadiazolyl, oxathiadiazolyl, triazolyl, tetrazolyl, thiadiazolyl, pyridyl, pyridazinyl, pyrimidinyl, pyrazinyl, triazinyl, and uracil, indolyl, isoindolyl, indazolyl, indolizinyl, azaindolyl, benzoxazolyl, benzimidazolyl, benzothiazolyl, benzofuranyl, benzothiophenyl, quinolyl, isoquinolyl, quinazolinyl, quinoxalinyl, naphthyridinyl, cinnolinyl, purinyl, and phthalazinyl.

Suitably, when $R_b$ is an optionally substituted heterocyclic, heterocyclic alkyl, they are as defined in the definition section, In one embodiment of the invention, when $R_b$ is an optionally substituted heteroaryl, heteroaryl alkyl, heterocyclic or heterocyclic alkyl, the moiety is a 1,3-thiazol-2-yl, 5-methyl-1,3-thiazol-2-yl, isoquinoline, 3-thiophene, indol-5yl, pyridin-3-yl, pyridine-4-yl, indazolyl, benzothiazolyl, 2-methyl-1,3-benzothiazol-5-yl, pyrazol-3-yl, 4-morpholino, 2-furanyl, 2-furanylmethyl, 2-thienyl, 2-thienylmethyl, tetrahydro-2H-pyran-4yl, tetrahydro-2H-pyran-4yl methyl, tetrahydro-2-furanyl, or tetrahydro-2-furanylmethyl, 1H-imidazol-4-yl or 1H-imidazol-4-ylethyl.

In an alternative embodiment, when $R_b$ is an optionally substituted heteroaryl the moiety is a 1,3-thiazol-2-yl or 5-methyl-1,3-thiazol-2-yl, isoquinolinyl, thiophene, pyridinyl, indazolyl, benzothiazolyl, e.g. 2-methyl-1,3-benzothiazol-5-yl.

In another embodiment, the heteroaryl ring is an optionally substituted thiazolyl, pyridyl, or thiophene ring.

Suitably, when $R_b$ is an optionally substituted aryl or arylalkyl moiety, the aryl containing is unsubstituted or substituted independently at each occurrence one or more times by halogen, alkyl, cyano, $OR_8$, $SR_5$, $S(O)_2R_5$, C(O)$R_j$, C(O)O$R_j$, -Z'-$(CR_{10}R_{20})$s-Z', halosubstituted $C_{1-10}$ alkyl, or an optionally substituted aryl.

In one embodiment, $R_b$ is a phenyl, or napthylene, 2-fluorophenyl, 3-fluorophenyl, 4-fluorophenyl, 2,3-difluorphenyl, 2,4-difluorophenyl, 3,4-difluorophenyl, 3,5-difluorophenyl, 3-chlorophenyl, 4-chlorophenyl, 3-chloro-4-fluorophenyl, 2-methyl phenyl, 3-methylphenyl, 4-methylphenyl, 6-methyl phenyl, 2-methyl phenyl, 3-amino phenyl, 3,4-dimethyl phenyl, 4-methyl-3-fluorophenyl, 4-trifluorophenyl, 4-ethoxyphenyl, 4-methoxyphenyl, 3-cyanophenyl, 4-cyanophenyl, 4-thiomethylphenyl, 4-acetylphenyl, 4-dimethylaminophenyl, benzyl, phenethyl, phenylpropyl, 2,3-difluoro-benzyl, 3,5-difluoro-benzyl, biphenyl, 4'-fluorobiphenyl, 4-sulfonamindo-2-methylphenyl, or 3-phenyloxyphenyl, 4-phenyloxyphenyl, 4-(1-piperidinylsulfonyl)-phenyl, or 3-(aminocarbonyl)phenyl.

In another embodiment, $R_b$ is a phenyl, 2-fluorophenyl, 3-fluorophenyl, 4-fluorophenyl, 2,4-difluorophenyl, 3,4-difluorophenyl, 3,5-difluorophenyl, 3-chlorophenyl, 4-chlorophenyl, 3-chloro-4-fluorophenyl, 4-methyl-3-fluorophenyl, 4-trifluorophenyl, 2-methylphenyl, 3-methylphenyl, 4-ethoxyphenyl, 4-methoxyphenyl, 3-cyanophenyl, 4-cyanophenyl, 4-thiomethylphenyl, 4-acetylphenyl, 4-dimethylaminophenyl, biphenyl, 4'-fluorobiphenyl, 4-sulfonamindo-2-methylphenyl, 3-phenyloxyphenyl, benzyl, or phenethyl.

Suitably, when $R_b$ is an optionally substituted cycloalkyl or cycloalkyl alkyl moiety, the moiety is a cyclopropyl, cyclobutyl, cyclopentyl, cyclohexyl, cyclopropylmethyl, or a cyclopentylmethyl. In another embodiment, $R_b$ is a cyclopropyl or cyclopropylmethyl group.

In another embodiment, $R_b$ is hydrogen, or an optionally substituted alkyl.

In another embodiment, $R_b$ is $C_{1-10}$ alkyl, heteroaryl, or aryl, all optionally substituted.

Suitably, m is independently selected at each occurrence from 0 or an integer having a value of 1 or 2.

For each of the integer variables where appropriate, e.g. n, n', m, q', s, t, or v', etc. they are independently chosen at each occurrence.

The moiety -Z'-$(CR_{10}R_{20})$s-Z' forms a cyclic ring, such as a dioxalane ring.

Suitably Z' is independently selected at each occurrence from oxygen, or sulfur.

Suitably, s is independently selected at each occurrence from an integer having a value of 1, 2, or 3.

Suitably, $R_{4'}$ and $R_{14'}$ are each independently hydrogen or $C_{1-4}$ alkyl, or $R_{4'}$ and $R_{14'}$ can cyclize together with the nitrogen to which to form a 5 to 7 membered ring which optionally contains an additional heteroatom selected from oxygen, sulfur or $NR_{9'}$.

Suitably, $R_{4''}$ and $R_{14''}$ are independently selected at each occurrence from hydrogen or $C_{1-4}$ alkyl, or $R_{4''}$ and $R_{14''}$ together with the nitrogen to which they are attached, cyclize to form a 5 to 7 membered ring which optionally contains an additional heteroatom selected from oxygen, sulfur or $NR_{9''}$. In one embodiment, when $R_{4'}$ and $R_{14'}$ cyclize to form an optionally substituted ring, such rings include, but are not limited to pyrrolidine, piperidine, piperazine, morpholine, and thiomorpholine (including oxidizing the sulfur).

Suitably, $R_{18}$ and $R_{28}$ are each independently selected at each occurrence from hydrogen, $C_{1-4}$ alkyl, $C_{3-7}$ cycloalkyl, $C_{3-7}$ cycloalkyl$C_{1-4}$alkyl, aryl, or aryl-$C_{1-4}$ alkyl, heteroaryl or heteroaryl $C_{1-4}$ alkyl moiety, and wherein these moieties, excluding hydrogen may be optionally substituted; or $R_{18}$ and $R_{28}$ together with the nitrogen which they are attached form an optionally substituted heterocyclic ring of 4 to 7 members, which ring optionally contains an additional heteroatom selected from oxygen, sulfur or $NR_9$; and wherein these moieties are optionally substituted 1 to 4 times, independently by halogen; hydroxy; hydroxy substituted $C_{1-10}$alkyl; $C_{1-10}$ alkoxy; halosubstituted $C_{1-10}$ alkoxy; $C_{1-4}$ alkyl; halosubstituted $C_{1-4}$ alkyl; $SR_5$, $S(O)R_5$, $S(O)_2R_5$; $C(O)R_j$; $C(O)OR_j$; $C(O)NR_{4'}R_{14'}$; $NR_4C(O)C_{1-10}$alkyl; $NR_4C(O)$aryl; $NR_4R_{14}$; cyano; nitro; $C_{1-10}$ alkyl; $C_{3-7}$cycloalkyl; $C_{3-7}$cycloalkyl $C_{1-10}$ alkyl; halosubstituted $C_{1-10}$ alkyl; aryl, aryl $C_{1-4}$ alkyl, heteroaryl, or hetero $C_{1-4}$ alkyl, and wherein these aryl or heteroaryl containing moieties may also be substituted one to two times independently by halogen, $C_{1-4}$ alkyl, hydroxy, hydroxy substituted $C_{1-4}$ alkyl, $C_{1-10}$ alkoxy, $S(O)_m$ alkyl, amino, mono & di-substituted $C_{1-4}$ alkyl amino, $C_{1-4}$ alkyl, or $CF_3$.

Suitably, $R_{19}$ is independently selected from hydrogen, $C_{1-4}$ alkyl, halo-substituted $C_{1-4}$ alkyl, $C_{2-4}$ alkenyl, $C_{2-4}$ alkynyl, $C_{3-7}$ cycloalkyl, $C_{3-7}$ cycloalkyl $C_{1-4}$ alkyl, $C_{5-7}$ cycloalkenyl, $C_{5-7}$cycloalkenyl $C_{1-4}$ alkyl, aryl, aryl$C_{1-4}$ alkyl, heteroaryl, heteroaryl$C_{1-4}$ alkyl, heterocyclyl, or a heterocyclyl$C_{1-4}$ alkyl moiety, and wherein these moieties, excluding hydrogen, may be optionally substituted 1 to 4 times by halogen; halosubstituted $C_{1-4}$ alkyl; $C_{1-4}$ alkyl; $C_{3-5}$cycloalkyl; $C_{3-5}$cycloalkyl $C_{1-4}$alkyl; halosubstituted $C_{1-4}$ alkyl; hydroxy; hydroxy substituted $C_{1-4}$alkyl; $C_{1-4}$alkoxy; halosubstituted $C_{1-4}$ alkoxy; $S(O)mC_{1-4}$ alkyl; —C(O), $C(O)C_{1-4}$ alkyl; $NR_{21}R_{31}$; or an aryl or arylalkyl, and wherein these aryl containing moieties may also be substituted one to two times by halogen, hydroxy, hydroxy substituted alkyl, $C_{1-4}$ alkoxy, $S(O)_mC_{1-4}$alkyl, amino, mono & di-substituted $C_{1-4}$ alkylamino, $C_{1-4}$ alkyl, or $CF_3$.

Suitably, $R_{21}$ and $R_{31}$ are each independently selected from hydrogen or $C_{1-4}$ alkyl, or $R_{21}$ and $R_{31}$ together with the nitrogen to which they are attached cyclize to form a 5 to 7 membered ring which optionally contains an additional heteroatom selected from oxygen, nitrogen, or sulfur.

Suitably, Z is independently selected from oxygen or sulfur.

Suitably, $R_2$ and $R_{2'}$ are independently selected from hydrogen, $C_{1-10}$ alkyl, $C_{3-7}$cycloalkyl, $C_{3-7}$cycloalkyl$C_{1-10}$ alkyl, $C_{5-7}$ cycloalkenyl, $C_{5-7}$ cycloalkenyl-$C_{1-10}$alkyl, aryl, aryl$C_{1-10}$ alkyl, heteroaryl, heteroaryl$C_{1-10}$ alkyl, heterocyclic, or a heterocyclyl$C_{1-10}$ alkyl moiety, wherein all of the moieties except for hydrogen, are optionally substituted; or $R_2$ and $R_{2'}$ together with the nitrogen to which they are attached form an optionally substituted 5 to 7 membered ring, which ring may contain an additional heteroatom selected from oxygen, nitrogen or sulfur. These moieties, excluding hydrogen, may be optionally substituted independently one or more times, suitably 1 to 4 times by hydrogen, $C_{1-4}$ alkyl, halo-substituted $C_{1-4}$ alkyl, $C_{2-4}$ alkenyl, $C_{2-4}$ alkynyl, $C_{3-7}$ cycloalkyl, $C_{3-7}$ cycloalkyl $C_{1-4}$ alkyl, $C_{5-7}$ cycloalkenyl, $C_{5-7}$cycloalkenyl $C_{1-4}$ alkyl, aryl, aryl$C_{1-4}$ alkyl, heteroaryl, heteroaryl$C_{1-4}$ alkyl, heterocyclyl, or a heterocyclyl$C_{1-4}$ alkyl moiety, and wherein these moieties, excluding hydrogen, may be optionally substituted 1 to 4 times by halogen; halosubstituted $C_{1-4}$ alkyl; $C_{1-4}$ alkyl; $C_{3-5}$cycloalkyl; $C_{3-5}$cycloalkyl $C_{1-4}$alkyl; halosubstituted $C_{1-4}$ alkyl; hydroxy; hydroxy substituted $C_{1-4}$alkyl; $C_{1-4}$alkoxy; halosubstituted $C_{1-4}$ alkoxy; $S(O)mC_{1-4}$ alkyl; —C(O), $C(O)C_{1-4}$ alkyl; $NR_{21}R_{31}$; or an aryl or arylalkyl, and wherein these aryl containing moieties may also be substituted one to two times by halogen, hydroxy, hydroxy substituted alkyl, $C_{1-4}$ alkoxy, $S(O)_mC_{1-4}$alkyl, amino, mono & di-substituted $C_{1-4}$ alkylamino, $C_{1-4}$ alkyl, or $CF_3$.

In one embodiment, $R_2$ and $R_{2'}$ are independently selected from hydrogen, or an optionally substituted $C_{1-10}$ alkyl.

Suitably, $R_a$ is independently selected from hydrogen, or an optionally substituted $C_{1-4}$ alkyl.

Suitably, $R_g$ is selected from an optionally substituted $C_{1-10}$ alkyl, —$CH_2$—$CH_2$—O—$CH_2$—$CH_2$—, —$CH_2$—$C(O)$—$CH_2$, $CH_2$—$C(O)N(R_{12})CH_2$—$CH_2$—, —$CH_2$—$N(R_{12})C(O)CH_2$—, $CH_2$—$CH(OR_{12})$—$CH_2$, $CH_2$—$C(O)O$—$CH_2$—$CH_2$, or —$CH_2$—$CH_2$—O—$C(O)CH_2$—.

The $C_{1-10}$ alkyl may be optionally substituted independently one or more times, suitably 1 to 4 times. In one embodiment $R_b$ is an optionally substituted $C_{1-4}$ alkyl.

Suitably, $R_{12}$ is hydrogen, or an optionally substituted $C_{1-4}$ alkyl wherein the $C_{1-4}$ alkyl is independently substituted one or more times, suitably 1 to 4 times.

Suitably, $R_3$ is a $C_{1-10}$ alkyl, $C_{3-7}$ cycloalkyl, $C_{3-7}$ cycloalkyl $C_{1-10}$ alkyl, aryl, aryl$C_{1-10}$ alkyl, heteroaryl, heteroaryl$C_{1-10}$ alkyl, heterocyclic, or heterocyclyl$C_{1-10}$ alkyl moiety, which moieties may be optionally substituted 1 to 4 times, independently at each occurrence by hydrogen, halogen, nitro, $C_{1-10}$ alkyl, halo-substituted $C_{1-10}$ alkyl, $C_{2-10}$ alkenyl, $C_{2-10}$alkynyl, $C_{3-7}$cycloalkyl, $C_{3-7}$cycloalkyl$C_{1-10}$ alkyl, $C_{5-7}$cycloalkenyl, $C_{5-7}$cycloalkenyl$C_{1-10}$ alkyl, $(CR_{10}R_{20})_nOR_6$, $(CR_{10}R_{20})_nSH$, $(CR_{10}R_{20})_nS(O)_mR_7$, $(CR_{10}R_{20})_nN(R_{10'})S(O)_2R_7$, $(CR_{10}R_{20})_n$ $NR_{16}R_{26}$, $(CR_{10}R_{20})_nCN$, $(CR_{10}R_{20})_nS(O)_2$ $NR_{16}R_{26}$, $(CR_{10}R_{20})_nC(Z)R_6$, $(CR_{10}R_{20})_nOC(Z)R_6$, $(CR_{10}R_{20})_nC(Z)OR_6$, $(CR_{10}R_{20})_nC(Z)NR_{16}R_{26}$, $(CR_{10}R_{20})_nN(R_{10'})C(Z)R_6$, $(CR_{10}R_{20})_nN(R_{10'})C(=N(R_{10'}))NR_{16}R_{26}$, $(CR_{10}R_{20})_nOC(Z)NR_{16}R_{26}$, $(CR_{10}R_{20})_nN(R_{10'})C(Z)$ $NR_{16}R_{26}$, or $(CR_{10}R_{20})_nN(v)C(Z)OR_7$.

Suitably, n is independently selected at each occurrence from 0, or an integer having a value of 1 to 10.

Suitably, n' is independently selected at each occurrence from 0, or an integer having a value of 1 to 10.

In one embodiment, $R_3$ is an optionally substituted $C_{1-10}$ alkyl, $C_{3-7}$ cycloalkyl, $C_{3-7}$ cycloalkyl$C_{1-4}$alkyl, or aryl moiety. In another embodiment, the $R_3$ moiety is optionally substituted one or more times, independently, by halogen, $C_{1-10}$ alkyl, halo-substituted $C_{1-10}$ alkyl, hydroxy, $C_{1-10}$ alkoxy, or amino.

In one embodiment, the $R_3$ moieties are optionally substituted 1 to 4 times, independently at each occurrence by halogen, nitro, $C_{1-4}$ alkyl, halo-substituted $C_{1-4}$ alkyl, $C_{2-4}$ alkenyl, $C_{2-4}$alkynyl, $C_{3-6}$cycloalkyl, $C_{3-6}$cycloalkyl$C_{1-4}$ alkyl, $C_{5-6}$cycloalkenyl, $C_{5-6}$cycloalkenyl$C_{1-4}$ alkyl, $(CR_{10}R_{20})_nOR_6$, $(CR_{10}R_{20})_nSH$, $(CR_{10}R_{20})_nS(O)_mR_7$, $(CR_{10}R_{20})_nNHS(O)_2R_7$, $(CR_{10}R_{20})_nS(O)_2NR_{16}R_{26}$, $(CR_{10}R_{20})_nNR_{16}R_{26}$, $(CR_{10}R_{20})_nCN$, $(CR_{10}R_{20})_nC(Z)R_6$, $(CR_{10}R_{20})_nOC(Z)R_6$, $(CR_{10}R_{20})_nC(Z)OR_6$, $(CR_{10}R_{20})_nN(R_{10'})C(Z)R_6$, or $(CR_{10}R_{20})_nC(Z)NR_{16}R_{26}$.

In one embodiment the $R_3$ moieties are optionally substituted independently, one or more times, suitably 1 to 4 times, independently at each occurrence by halogen, $C_{1-10}$ alkyl, hydroxy, $C_{1-10}$ alkoxy, cyano, nitro, amino, or halosubstituted $C_{1-10}$ alkyl. In another embodiment, the $R_3$ substituents are selected independently from halogen, such as fluorine, chlorine, bromine or iodine, or $C_{1-10}$ alkyl, such as methyl.

In one embodiment the $R_3$ moieties are an optionally substituted $C_{1-10}$ alkyl, optionally substituted $C_{3-7}$cycloalkyl, optionally substituted $C_{3-7}$cycloalkylalkyl, or optionally substituted aryl. In another embodiment, the $R_3$ moiety is an optionally substituted $C_{1-10}$ alkyl, or an optionally substituted aryl. In another embodiment, $R_3$ is an optionally substituted phenyl.

Suitably, in one embodiment when $R_3$ is an aryl moiety, it is an optionally substituted phenyl ring. The phenyl is optionally substituted one or more times, independently at each occurrence, suitably 1 to 4 times by halogen, $C_{1-4}$ alkyl, or halo-substituted-$C_{1-4}$ alkyl. The phenyl ring may be substituted in the 2, 4, or 6-position, or di-substituted in the 2,4-position or 2,6-position, such as 2-fluoro, 4-fluoro, 2,4-difluoro, 2,6-difluoro, or 2-methyl-4-fluoro; or tri-substituted in the 2,4,6-position, such as 2,4,6-trifluoro.

Suitably, $R_4$ and $R_{14}$ are each independently selected from hydrogen, optionally substituted $C_{1-4}$ alkyl, optionally substituted $C_{3-7}$ cycloalkyl, $C_{3-7}$ cycloalkyl$C_{1-4}$alkyl, optionally substituted aryl, or optionally substituted aryl-$C_{1-4}$ alkyl, heteroaryl, heteroaryl $C_{1-4}$ alkyl, heterocyclic, or heterocyclic $C_{1-4}$ alkyl; or $R_4$ and $R_{14}$ together with the nitrogen which they are attached form an optionally substituted heterocyclic ring of 4 to 7 members, which ring optionally contains an additional heteroatom selected from oxygen, sulfur or nitrogen, and wherein the $C_{1-10}$ alkyl, $C_{3-7}$cycloalkyl, $C_{3-7}$cycloalkyl$C_{1-4}$ alkyl, aryl, aryl-$C_{1-4}$ alkyl, heteroaryl and heteroaryl $C_{1-4}$ alkyl moieties, and the $R_4$ and $R_{14}$ cyclized ring are optionally substituted, 1 to 4 times, independently at each occurrence, by halogen; hydroxy; hydroxy substituted $C_{1-10}$alkyl; $C_{1-10}$ alkoxy; halosubstituted $C_{1-10}$ alkoxy; $C_{1-10}$ alkyl; halosubstituted $C_{1-10}$ alkyl; $SR_5$; $S(O)R_5$; $S(O)_2R_5$; $C(O)R_j$; $C(O)ORj$; $C(O)NR_4'R_{14'}$; $(CR_{10}R_{20})_{n'}$ $N(R_{10'})C(Z)OR_7$; $(CR_{10}R_{20})_{n'}N(R_{10'})C(Z)$ $NR_dR_{d'}$; $NR_4C(O)C_{1-10}$alkyl; $NR_4C(O)$aryl; $NR_4'R_{14'}$; cyano; nitro; $C_{3-7}$cycloalkyl; $C_{3-7}$cycloalkyl $C_{1-10}$ alkyl; $C_{1-10}$ alkyl substituted one or more times by an optionally substituted aryl; an unsubstituted or substituted aryl, or aryl$C_{1-4}$ alkyl; an unsubstituted or substituted heteroaryl, or heteroaryl $C_{1-4}$ alkyl; an unsubstituted or substituted heterocyclic, or heterocyclic $C_{1-4}$ alkyl, and wherein these aryl, heterocyclic and heteroaryl containing moieties are substituted one to two times independently at each occurrence by halogen; $C_{1-4}$ alkyl, hydroxy; hydroxy substituted $C_{1-4}$ alkyl; $C_{1-4}$ alkoxy; $S(O)_m$alkyl; amino, mono & di-substituted $C_{1-4}$ alkyl amino, or $CF_3$.

Suitably, $R_d$ and $R_{d'}$ are each independently selected at each occurrence from hydrogen, $C_{1-4}$ alkyl, $C_{3-6}$ cycloalkyl, $C_{3-6}$ cycloalkyl$C_{1-4}$alkyl, or the $R_d$ and $R_{d'}$ together with the nitrogen which they are attached form an optionally substituted heterocyclic ring of 5 to 6 members, which ring optionally contains an additional heteroatom selected from oxygen, sulfur or $NR_9$; and wherein the $R_d$ and $R_{d'}$ moieties which are $C_{1-4}$ alkyl, $C_{3-6}$cycloalkyl, $C_{3-6}$cycloalkyl$C_{1-4}$ alkyl, and the $R_d$ and $R_{d'}$ cyclized ring are substituted, 1 to 4 times, independently at each occurrence by halogen; halosubstituted $C_{1-4}$ alkyl; hydroxy; hydroxy substituted $C_{1-4}$alkyl; $C_{1-4}$ alkoxy; halosubstituted $C_{1-4}$ alkoxy; $S(O)mRf$; $C(O)Rj$; $C(O)ORj$; $C(O)NR_4'R_{14'}$; $NR_4'C(O)C_{1-4}$alkyl; $S(O)_2NR_4'R_{14'}C_{1-4}$ alkyl; $NR_4'R_{14'}S(O)_2C_{1-4}$ alkyl; or $NR_4'R_{14'}$.

Suitably, $R_5$ is independently selected from hydrogen, $C_{1-4}$ alkyl, $C_{2-4}$ alkenyl, $C_{2-4}$ alkynyl or $NR_4'R_{14'}$, excluding the moieties $SR_5$ being $SNR_4'R_{14'}$, $S(O)_2R_5$ being $SO_2H$ and $S(O)R_5$ being $SOH$.

Suitably, $R_6$ is independently selected from hydrogen, $C_{1-10}$ alkyl, $C_{3-7}$ cycloalkyl, heterocyclyl, heterocyclyl $C_{1-10}$alkyl, aryl, aryl$C_{1-10}$ alkyl, heteroaryl or heteroaryl$C_{1-10}$ alkyl, wherein each of these moieties may be optionally substituted independently one or more times, suitably 1 to 4 times.

Suitably, $R_7$ is independently selected from $C_{1-6}$alkyl, aryl, aryl$C_{1-6}$alkyl, heterocyclic, heterocyclyl$C_{1-6}$ alkyl, heteroaryl, or heteroaryl$C_{1-6}$alkyl; and wherein each of these moieties may be optionally substituted independently one or more times, suitably 1 to 4 times.

Suitably, $R_8$ is independently selected from hydrogen, $C_{1-4}$ alkyl, halo-substituted $C_{1-4}$ alkyl, $C_{2-4}$ alkenyl, $C_{2-4}$ alkynyl, $C_{3-7}$ cycloalkyl, $C_{5-7}$ cycloalkenyl, aryl, aryl$C_{1-4}$ alkyl, heteroaryl, heteroaryl$C_{1-4}$ alkyl, heterocyclyl, heterocyclyl$C_{1-4}$ alkyl, $(CR_{10}R_{20})_rOR_7$, $(CR_{10}R_{20})_rS(O)_mR_7$, $(CR_{10}R_{20})_rN(R_{10'})S(O)_2R_7$, or $(CR_{10}R_{20})_rNR_4R_{14}$; and wherein the cycloalkyl, cycloalkenyl, aryl, arylalkyl, heteroaryl, heteroaryl alkyl, heterocyclic and heterocyclic alkyl moieties may be optionally substituted independently at each occurrence one or more times, suitably 1 to 4 times, by halogen; halosubstituted$C_{1-4}$ alkyl; $C_{1-4}$ alkyl; $C_{3-5}$cycloalkyl; $C_{3-5}$cycloalkyl $C_{1-4}$alkyl; halosubstituted $C_{1-4}$ alkyl; hydroxy; hydroxy substituted $C_{1-4}$ alkyl; $C_{1-4}$alkoxy; halosubstituted $C_{1-4}$ alkoxy; $S(O)mC_{1-4}$ alkyl; —C(O), $C(O)C_{1-4}$ alkyl;

$NR_{21'}R_{31'}$; or an aryl or aryl $C_{1-4}$ alkyl, and wherein these aryl containing moieties may also be substituted one to two times independently at each occurrence, by halogen, hydroxy, hydroxy substituted alkyl, $C_{1-4}$ alkoxy, $S(O)_m C_{1-4}$alkyl, amino, mono & di-substituted $C_{1-4}$ alkylamino, $C_{1-4}$ alkyl, or $CF_3$.

Suitably, $R_{21'}$ and $R_{31'}$ are each independently selected at each occurrence from hydrogen or $C_{1-4}$ alkyl, or $R_{21'}$ and $R_{31'}$ together with the nitrogen to which they are attached cyclize to form a 5 to 7 membered ring which optionally contains an additional heteroatom selected from oxygen, nitrogen, or sulfur.

Suitably, $R_9$ is hydrogen, $C(Z)R_6$ or optionally substituted $C_{1-10}$ alkyl, optionally substituted aryl or optionally substituted aryl-$C_{1-4}$ alkyl, wherein the optional substituents are independently substituted one or more times, suitably 1 to 4 times.

Suitably, $R_{10}$ and $R_{20}$ are independently selected at each occurrence from hydrogen or $C_{1-4}$alkyl.

Suitably, $R_{11}$ is $C_{1-4}$ alkyl, halo-substituted $C_{1-4}$ alkyl, $C_{2-4}$ alkenyl, $C_{2-4}$ alkynyl, $C_{3-7}$ cycloalkyl, $C_{5-7}$ cycloalkenyl, aryl, aryl$C_{1-4}$ alkyl, heteroaryl, heteroaryl$C_{1-4}$ alkyl, heterocyclyl, heterocyclyl$C_{1-4}$ alkyl, $(CR_{10}R_{20})_tOR_7$, $(CR_{10}R_{20})_sS(O)_mR_7$, $(CR_{10}R_{20})_t N(R_{10'})S(O)_2R_7$, or $(CR_{10}R_{20})_vNR_4R_{14}$; and wherein the aryl, arylalkyl, heteroaryl, heteroaryl alkyl, heterocyclyl, and heterocyclylalkyl moieties may be optionally substituted independently one or more times, suitably 1 to 4 times.

Suitably m is independently selected at each occurrence from 0, or an integer having a value of 1 or 2.

Suitably, t is independently selected at each occurrence from an integer having a value of 1 to 3.

Suitably, q is independently selected at each occurrence from an integer having a value of 1 to 10.

Suitably, the dotted line is an optional double bond, providing for a saturated or unsaturated pyridyl containing ring.

Suitably, for compounds of Formula (II), Y is $C(R_{13'})(R_{16'})$, $C(O)$, $N(R_{16'})$, $N(R_{17'})C(R_{15'})(R_{16'})$, oxygen, $OC(R_{15'})(R_{16'})$, $S(O)m$, or $S(O)_m C(R_{15'})(R_{16'})$;

Suitably, $R_{13'}$ is hydrogen, $C_{1-2}$ alkyl, $N(R_{18'})_2$, hydroxy, thio, $C_{1-2}$ alkoxy, or $S(O)_m C_{1-2}$alkyl.

Suitably, $R_{15'}$ is hydrogen or $C_{1-2}$ alkyl.

Suitably, $R_{16'}$ is hydrogen or $C_{1-2}$ alkyl.

Suitably, $R_{17'}$ is hydrogen or $C_{1-2}$ alkyl.

Suitably, $R_{18'}$ is independently selected at each occurrence from hydrogen or $C_{1-2}$ alkyl.

For each of the integer variables where appropriate, e.g. n, n', m, q', s, t, or v', etc. they are independently chosen at each occurrence.

As used herein, "optionally substituted" unless specifically defined shall mean halogen, such as fluorine, chlorine, bromine or iodine; hydroxy; hydroxy substituted $C_{1-10}$alkyl; $C_{1-10}$ alkoxy, such as methoxy or ethoxy; halosubstituted $C_{1-10}$ alkoxy; $S(O)m$ alkyl, such as methyl thio, methylsulfinyl or methyl sulfonyl; a ketone (—$C(O)$), or an aldehyde (—$C(O)R_{6'}$), such as $C(O)C_{1-10}$ alkyl or $C(O)$aryl, wherein $R_{6'}$ is hydrogen, $C_{1-10}$ alkyl, $C_{3-7}$ cycloalkyl, heterocyclyl, heterocyclyl $C_{1-10}$alkyl, aryl, aryl$C_{1-10}$ alkyl, heteroaryl or heteroaryl$C_{1-10}$ alkyl, (and wherein the $R_{6'}$ moieties, excluding hydrogen, may themselves be optionally substituted 1 or 2 times, independently by halogen; hydroxy; hydroxy substituted alkyl; $C_{1-4}$ alkoxy; $S(O)_m$alkyl; amino, mono & di-substituted $C_{1-4}$ alkyl amino; $C_{1-4}$ alkyl, or $CF_3$); $NR_{4'}R_{14'}$, wherein $R_{4'}$ and $R_{14'}$ are each independently hydrogen or $C_{1-4}$ alkyl, such as amino or mono or -disubstituted $C_{1-4}$ alkyl or wherein the $R_{4'}R_{14'}$ can cyclize together with the nitrogen to which they are attached to form a 5 to 7 membered ring which optionally contains an additional heteroatom selected from O/N/S; $C_{1-10}$ alkyl, such as methyl, ethyl, propyl, isopropyl, t-butyl, etc.; a $C_{3-7}$cycloalkyl or $C_{3-7}$cycloalkyl $C_{1-10}$ alkyl group, such as cyclopropyl or cyclopropyl methyl; halosubstituted $C_{1-10}$ alkyl, such $CF_2CF_2H$, or $CF_3$; an optionally substituted aryl, such as phenyl, or an optionally substituted aryl $C_{1-10}$ alkyl, such as benzyl or phenethyl, (and wherein these containing moieties may also be substituted one to two times independently by halogen; hydroxy; hydroxy substituted alkyl; $C_{1-10}$ alkoxy; $S(O)_m$ $C_{1-4}$ alkyl; amino, mono & di-substituted $C_{1-4}$ alkylamino; $C_{1-4}$ alkyl, or $CF_3$).

It is to be understood that the present invention covers all combinations of particular and preferred groups described hereinabove. It is also to be understood that the present invention encompasses compounds of formula (I) in which a particular group or parameter, for example $R_5$, $R_6$, $R_8$, $R_9$, $R_{10}$, $R_{11}$, $R_{12}$, m, n, t or v, etc. may occur more than once. In such compounds it will be appreciated that each group or parameter is independently selected, at each occurrence, from the values listed. When any variable occurs more than one time in Formula I, its definition on each occurrence is independent of its definition at every other occurrence Particular compounds according to the invention include those mentioned in the examples and their pharmaceutically derivatives.

As used herein, the term "pharmaceutically acceptable" means a compound which is suitable for pharmaceutical use. Salts and solvates of compounds of the invention which are suitable for use in medicine are those wherein the counterion or associated solvent is pharmaceutically acceptable. However, salts and solvates having non-pharmaceutically acceptable counterions or associated solvents are within the scope of the present invention, for example, for use as intermediates in the preparation of other compounds of the invention and their pharmaceutically acceptable salts and solvates.

As used herein, the term "pharmaceutically acceptable derivative", means any pharmaceutically acceptable salt, solvate or prodrug e.g. ester, of a compound of the invention, which upon administration to the recipient is capable of providing (directly or indirectly) a compound of the invention, or an active metabolite or residue thereof. Such derivatives are recognizable to those skilled in the art, without undue experimentation. Nevertheless, reference is made to the teaching of Burger's Medicinal Chemistry and Drug Discovery, 5th Edition, Vol. 1: Principles and Practice, which is incorporated herein by reference to the extent of teaching such derivatives. In one embodiment of the present invention the pharmaceutically acceptable derivatives are salts, solvates, esters, carbamates and phosphate esters. In another embodiment pharmaceutically acceptable derivatives are salts, solvates and esters. In yet another embodiment, pharmaceutically acceptable derivatives are salts and esters, in particular salts.

Suitable pharmaceutically acceptable salts are well known to those skilled in the art and include basic salts of inorganic and organic acids, such as hydrochloric acid, hydrobromic acid, sulphuric acid, phosphoric acid, methane sulphonic acid, ethane sulphonic acid, acetic acid, malic acid, tartaric acid, citric acid, lactic acid, oxalic acid, succinic acid, fumaric acid, maleic acid, benzoic acid, salicylic acid, phenylacetic acid and mandelic acid.

The compounds of the present invention may be in the form of and/or may be administered as a pharmaceutically acceptable salt. For a review on suitable salts see Berge et al., J. Pharm. Sci., 1977, 66, 1-19.

Typically, a pharmaceutical acceptable salt may be readily prepared by using a desired acid or base as appropriate. The salt may precipitate from solution and be collected by filtration or may be recovered by evaporation of the solvent.

Pharmaceutically acceptable salts of compounds of Formula (I) may suitably be formed with a pharmaceutically acceptable cation, for instance, if a substituent group comprises a carboxy moiety. Suitable pharmaceutically acceptable cations are well known to those skilled in the art and include alkaline, alkaline earth, ammonium and quaternary ammonium cations.

Those skilled in the art of organic chemistry will appreciate that many organic compounds can form complexes with solvents in which they are reacted or from which they are precipitated or crystallized. These complexes are known as "solvates". As used herein, the term "solvate" refers to a complex of variable stoichiometry formed by a solute (in this invention, a compound of formula (I) or a salt thereof) and a solvent. Such solvents for the purpose of the invention may not interfere with the biological activity of the solute. Examples of suitable solvents include water, methanol, ethanol and acetic acid. Preferably the solvent used is a pharmaceutically acceptable solvent. Examples of suitable pharmaceutically acceptable solvents include water, ethanol and acetic acid. Most preferably the solvent used is water. A complex with water is known as a "hydrate". Solvates of the compound of the invention are within the scope of the invention.

The term "halo" or "halogens" is used herein to mean the halogens, chloro, fluoro, bromo and iodo.

The term "$C_{1-10}$alkyl" or "alkyl" or "alkyl$_{1-10}$" is used herein to mean both straight and branched chain radicals of 1 to 10 carbon atoms, unless the chain length is otherwise limited, including, but not limited to, methyl, ethyl, n-propyl, iso-propyl, n-butyl, sec-butyl, iso-butyl, tert-butyl, n-pentyl and the like.

The term "cycloalkyl" is used herein to mean cyclic radicals, such as a non-aromatic hydrocarbon ring containing a specified number of carbon atoms. For example, $C_{3-8}$cycloalkyl means a non-aromatic ring containing at least three, and at most eight, ring carbon atoms. Representative examples of "cycloalkyl" as used herein include, but are not limited to, cyclopropyl, cyclobutyl, cyclopentyl, cyclohexyl and cycloheptyl and the like.

The term "cycloalkenyl" is used herein to mean cyclic radicals, such as a non-aromatic hydrocarbon ring containing a specified number of carbon atoms preferably containing 5 to 8 carbons, which have at least one bond including but not limited to cyclopentenyl, cyclohexenyl, and the like.

The term "alkenyl" is used herein at all occurrences to mean straight or branched chain radical of 2-10 carbon atoms, unless the chain length is limited thereto, including, but not limited to ethenyl, 1-propenyl, 2-propenyl, 2-methyl-1-propenyl, 1-butenyl, 2-butenyl and the like.

The term "alkoxy" is used herein at all occurrences to refer to a straight or branched chain of an alkoxy group containing the specified number of carbon atoms. For example, $C_{1-6}$alkoxy means a straight or branched alkoxy containing at least 1, and at most 6, carbon atoms. Examples of "alkoxy" as used herein include, but are not limited to, methoxy, ethoxy, propoxy, prop-2-oxy, butoxy, but-2-oxy, 2-methylprop-1-oxy, 2-methylprop-2-oxy, pentoxy and hexyloxy.

The term "aryl" is used herein to mean phenyl, naphthyl and indene.

The term "heteroaryl" (on its own or in any combination, such as "heteroaryloxy", or "heteroaryl alkyl") as used herein refers to a monocyclic five- to seven-membered unsaturated hydrocarbon ring containing at least one heteroatom selected from oxygen, nitrogen and sulfur. Examples of heteroaryl rings include, but are not limited to, furyl, pyranyl, thienyl, pyrrolyl, oxazolyl, thiazolyl, isoxazolyl, isothiazolyl, imidazolyl, pyrazolyl, oxadiazolyl, oxathiadiazolyl, triazolyl, tetrazolyl, thiadiazolyl, pyridyl, pyridazinyl, pyrimidinyl, pyrazinyl, triazinyl, and uracil. The terms "heteroaryl ring", "heteroaryl moiety", and "heteroaryl" "(on its own or in any combination, such as "heteroaryloxy", or "heteroaryl alkyl") shall also refer to fused aromatic rings comprising at least one heteroatom selected from oxygen, nitrogen and sulfur. Each of the fused rings may have five or six ring atoms. Examples of fused aromatic rings include, but are not limited to, indolyl, isoindolyl, indazolyl, indolizinyl, azaindolyl, benzoxazolyl, benzimidazolyl, benzothiazolyl, benzofuranyl, benzothiophenyl, quinolyl, isoquinolyl, quinazolinyl, quinoxalinyl, naphthyridinyl, cinnolinyl, purinyl, and phthalazinyl.

The term "heterocyclic" (on its own or in any combination, such as "heterocyclylalkyl") is used herein to refer to a monocyclic three- to seven-membered saturated or non-aromatic, unsaturated hydrocarbon ring containing at least one heteroatom selected from nitrogen, oxygen, sulphur or oxidized sulphur moieties, such as S(O)m, and m is 0 or an integer having a value of 1 or 2. The terms "heterocyclic rings", "heterocyclic moieties", and "heterocyclyl" shall also refer to fused rings, saturated or partially unsaturated, and wherein one of the rings may be aromatic, or heteroaromatic. Each of the fused rings may have from four to seven ring atoms. Examples of heterocyclyl groups include, but are not limited to, the saturated or partially saturated versions of the heteroaryl moieties as defined above, such as tetrahydropyrrole, tetrahydropyran, tetrahydrofuran, tetrahydrothiophene (including oxidized versions of the sulfur moiety), azepine, diazepine, aziridinyl, pyrrolinyl, pyrrolidinyl, 2-oxo-1-pyrrolidinyl, 3-oxo-1-pyrrolidinyl, 1,3-benzdioxol-5-yl, imidazolinyl, imidazolidinyl, indolinyl, pyrazolinyl, pyrazolidinyl, piperidinyl, piperazinyl, morpholino and thiomorpholino (including oxidized versions of the sulfur moiety).

The term "aralkyl" or "heteroarylalkyl" or "heterocyclicalkyl" is used herein to mean $C_{1-4}$ alkyl as defined above attached to an aryl, heteroaryl or heterocyclic moiety as also defined herein unless otherwise indicated.

The term "sulfinyl" is used herein to mean the oxide S(O) of the corresponding sulfide, the term "thio" refers to the sulfide, and the term "sulfonyl" refers to the fully oxidized $S(O)_2$ moiety.

The term "aroyl" is used herein to mean C(O)Ar, wherein Ar is as phenyl, naphthyl, or aryl alkyl derivative such as defined above, such group include but are not limited to benzyl and phenethyl.

The term "alkanoyl" is used herein to mean $C(O)C_{1-10}$ alkyl wherein the alkyl is as defined above.

As used herein, the term "optionally" means that the subsequently described event(s) may or may not occur, and includes both event(s) which occur and events that do not occur.

As used herein, the term "substituted" refers to substitution with the named substituent or substituents, multiple degrees of substitution being allowed unless otherwise stated.

With regard to stereoisomers, the compounds of the Formulas herein may have one or more asymmetric carbon atom and may occur as racemates, racemic mixtures and as individual enantiomers or diastereomers. All such isomeric forms are included within the present invention, including mixtures thereof.

Cis (E) and trans (Z) isomerism may also occur. The present invention includes the individual stereoisomers of the compound of the invention and where appropriate, the individual tautomeric forms thereof, together with mixtures thereof.

Separation of diastereoisomers or cis and trans isomers may be achieved by conventional techniques, e.g. by fractional crystallisation, chromatography or H.P.L.C. A stereoisomeric mixture of the agent may also be prepared from a corresponding optically pure intermediate or by resolution, such as H.P.L.C. of the corresponding racemate using a suitable chiral support or by fractional crystallisation of the diastereoisomeric salts formed by reaction of the corresponding racemate with a suitable optically active acid or base, as appropriate.

Furthermore, some of the crystalline forms of the compounds of the Formulas herein may exist as polymorphs, which are included in the present invention.

Exemplified compounds of the compounds of this invention include the racemates, or optically active forms of the compounds of the working examples herein, and pharmaceutically acceptable salts thereof.

All numbers expressing quantities of ingredients, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

It is to be understood that the present invention covers all combinations of particular and preferred groups described hereinabove. It is also to be understood that the present invention encompasses compounds of formula (I) in which a particular group or parameter, for example $R_5$, $R_6$, $R_9$, $R_{10}$, $R_{11}$, $R_{12}$, $R_{13}$, n, m or t, etc. may occur more than once. In such compounds it will be appreciated that each group or parameter is independently selected from the values listed. When any variable occurs more than one time in a Formula (as described herein), its definition on each occurrence is independent of its definition at every other occurrence.

Exemplified compounds of Formula (I) are:

8-(2,6-Difluorophenyl)-4-(4-fluoro-2-methylphenyl)-2-(2-[N'-cyanoguanadino]-aminoethyl)amino]-8H-pyrido[2,3-d]pyrimidin-7-one;

8-(2,6-Difluorophenyl)-4-(4-fluoro-2-methylphenyl)-2-(2-[N'-cyano-N"-methylguanadino]-aminoethyl)amino]-8H-pyrido[2,3-d]pyrimidin-7-one;

8-(2,6-Difluorophenyl)-4-(4-fluoro-2-methylphenyl)-2-(2-[N'-cyano-N"-ethylguanadino]-aminoethyl)amino]-8H-pyrido[2,3-d]pyrimidin-7-one;

N-Cyano-N'-(2-{[4-(2,4-difluorophenyl)-8-(2-fluorophenyl)-7-oxo-7,8-dihydropyrido[2,3-d]pyrimidin-2-yl]amino}ethyl)guanidine;

N-Cyano-N'-(2-{[8-(2,6-difluorophenyl)-4-(2-methylphenyl)-7-oxo-7,8-dihydropyrido[2,3-d]pyrimidin-2-yl]amino}ethyl)guanidine;

N-Cyano-N'-(2-{[8-(2,6-difluorophenyl)-4-(4-fluorophenyl)-7-oxo-7,8-dihydropyrido[2,3-d]pyrimidin-2-yl]amino}ethyl)guanidine;

N-cyano-N'-(2-{[4-(2,4-difluorophenyl)-8-(2,6-difluorophenyl)-7-oxo-7,8-dihydropyrido[2,3-d]pyrimidin-2-yl]amino}ethyl)guanidine;

or pharmaceutically acceptable salts thereof.

METHODS OF TREATMENT

The compounds of Formula (I) and (II) or a pharmaceutically acceptable salt, solvate, or physiologically functional derivative thereof can be used in the manufacture of a medicament for the prophylactic or therapeutic treatment of any disease state in a human, or other mammal, which is exacerbated or caused by excessive or unregulated cytokine production by such mammal's cell, such as but not limited to monocytes and/or macrophages.

For purposes herein, compounds of Formula (I) and (II) will all be referred to as compounds of Formula (I) herein unless otherwise indicated.

Compounds of Formula (I) are capable of inhibiting proinflammatory cytokines, such as IL-1, IL-6, IL-8, and TNF and are therefore of use in therapy. IL-1, IL-6, IL-8 and TNF affect a wide variety of cells and tissues and these cytokines, as well as other leukocyte-derived cytokines, are important and critical inflammatory mediators of a wide variety of disease states and conditions. The inhibition of these pro-inflammatory cytokines is of benefit in controlling, reducing and alleviating many of these disease states.

Accordingly, the present invention provides a method of treating the inflammatory component of a cytokine-mediated disease which comprises administering an effective cytokine-interfering amount of a compound of Formula (I) or a pharmaceutically acceptable salt thereof.

Compounds of Formula (I) are capable of inhibiting inducible proinflammatory proteins, such as COX-2, also referred to by many other names such as prostaglandin endoperoxide synthase-2 (PGHS-2) and are therefore of use in therapy. These proinflammatory lipid mediators of the cyclooxygenase (CO) pathway are produced by the inducible COX-2 enzyme. Regulation, therefore of COX-2 which is responsible for the these products derived from arachidonic acid, such as prostaglandins affect a wide variety of cells and tissues are important and critical inflammatory mediators of a wide variety of disease states and conditions. Expression of COX-1 is not effected by compounds of Formula (I). This selective inhibition of COX-2 may alleviate or spare ulcerogenic liability associated with inhibition of COX-1 thereby inhibiting prostoglandins essential for cytoprotective effects. Thus inhibition of these pro-inflammatory mediators is of benefit in controlling, reducing and alleviating many of these disease states. Most notably these inflammatory mediators, in particular prostaglandins, have been implicated in pain, such as in the sensitization of pain receptors, or edema. This aspect of pain management therefore includes treatment of neuromuscular pain, headache, cancer pain, and arthritis pain. Compounds of Formula (I) or a pharmaceutically acceptable salt thereof, are of use in the prophylaxis or therapy in a human, or other mammal, by inhibition of the synthesis of the COX-2 enzyme.

Accordingly, the present invention provides a method of inhibiting the synthesis of COX-2 which comprises administering an effective amount of a compound of Formula (I) or a pharmaceutically acceptable salt thereof. The present invention also provides for a method of prophylaxis treatment in a human, or other mammal, by inhibition of the synthesis of the COX-2 enzyme.

In particular, compounds of Formula (I) or a pharmaceutically acceptable salt thereof are of use in the prophylaxis or therapy of any disease state in a human, or other mammal, which is exacerbated by or caused by excessive or unregulated IL-1, IL-6, IL-8 or TNF production by such mammal's cell, such as, but not limited to, monocytes and/or macrophages.

Accordingly, in another aspect, this invention relates to a method of inhibiting the production of IL-1 in a mammal in need thereof which comprises administering to said mammal an effective amount of a compound of Formula (I) or a pharmaceutically acceptable salt thereof.

There are many disease states in which excessive or unregulated IL-1 production is implicated in exacerbating and/or causing the disease. These include rheumatoid arthritis, osteoarthritis, meningitis, ischemic and hemorrhagic stroke, neurotrauma/closed head injury, stroke, endotoxemia and/or toxic shock syndrome, other acute or chronic inflammatory disease states such as the inflammatory reaction induced by endotoxin or inflammatory bowel disease, tuberculosis, atherosclerosis, muscle degeneration, multiple sclerosis, cachexia, bone resorption, psoriatic arthritis, Reiter's syndrome, gout, traumatic arthritis, rubella arthritis and acute synovitis. Recent evidence also links IL-1 activity to diabetes, pancreatic β cell diseases and Alzheimer's disease.

Use of a CSAID inhibitor compound for the treatment of CSBP mediated disease states, can include, but not be limited to neurodegenerative diseases, such as Alzheimer's disease (as noted above), Parkinson's disease and multiple sclerosis, etc.

In a further aspect, this invention relates to a method of inhibiting the production of TNF in a mammal in need thereof which comprises administering to said mammal an effective amount of a compound of Formula (I) or a pharmaceutically acceptable salt thereof.

Excessive or unregulated TNF production has been implicated in mediating or exacerbating a number of diseases including rheumatoid arthritis, rheumatoid spondylitis, osteoarthritis, gouty arthritis and other arthritic conditions, sepsis, septic shock, endotoxic shock, gram negative sepsis, toxic shock syndrome, adult respiratory distress syndrome, chronic pulmonary inflammatory disease and chronic obstructive pulmonary disease, silicosis, pulmonary sarcoisosis, bone resorption diseases, such as osteoporosis, cardiac, brain and renal reperfusion injury, graft vs. host reaction, allograft rejections, fever and myalgias due to infection, such as influenza, brain infections including encephalitis (including HIV-induced forms), cerebral malaria, meningitis, ischemic and hemorrhagic stroke, cachexia secondary to infection or malignancy, cachexia secondary to acquired immune deficiency syndrome (AIDS), AIDS, ARC (AIDS related complex), keloid formation, scar tissue formation, inflammatory bowel disease, Crohn's disease, ulcerative colitis and pyresis.

Compounds of Formula (I) are also useful in the treatment of viral infections, where such viruses are sensitive to upregulation by TNF or will elicit TNF production in vivo. The viruses contemplated for treatment herein are those that produce TNF as a result of infection, or those which are sensitive to inhibition, such as by decreased replication, directly or indirectly, by the TNF inhibiting-compounds of Formula (1). Such viruses include, but are not limited to HIV-1, HIV-2 and HIV-3, Cytomegalovirus (CMV), Influenza, adenovirus and the Herpes group of viruses, such as but not limited to, Herpes Zoster and Herpes Simplex. Accordingly, in a further aspect, this invention relates to a method of treating a mammal afflicted with a human immunodeficiency virus (HIV) which comprises administering to such mammal an effective TNF inhibiting amount of a compound of Formula (I) or a pharmaceutically acceptable salt thereof.

It is also recognized that both IL-6 and IL-8 are produced during rhinovirus (HRV) infections and contribute to the pathogenesis of common cold and exacerbation of asthma associated with HRV infection (Turner et al. (1998), Clin. Infec. Dis., Vol. 26, p 840; Teren et al. (1997), Am. J. Respir. Crit. Care Med., Vol. 155, p 1362; Grunberg et al. (1997), Am. J. Respir. Crit. Care Med. Vol. 156, p 609 and Zhu et al, J. Clin. Invest (1996), 97:421). It has also been demonstrated in vitro that infection of pulmonary epithelial cells with HRV results in production of IL-6 and IL-8 (Subauste et al., J. Clin. Invest. 1995, 96:549.) Epithelial cells represent the primary site of infection of HRV. Therefore another aspect of the present invention is a method of treatment to reduce inflammation associated with a rhinovirus infection, not necessarily a direct effect on virus itself.

Compounds of Formula (I) may also be used in association with the veterinary treatment of mammals, other than in humans, in need of inhibition of TNF production. TNF mediated diseases for treatment, therapeutically or prophylactically, in animals include disease states such as those noted above, but in particular viral infections. Examples of such viruses include, but are not limited to, lentivirus infections such as, equine infectious anaemia virus, caprine arthritis virus, visna virus, or maedi virus or retrovirus infections, such as but not limited to feline immunodeficiency virus (FIV), bovine immunodeficiency virus, or canine immunodeficiency virus or other retroviral infections.

The compounds of Formula (I) may also be used topically in the treatment or prophylaxis of topical disease states mediated by or exacerbated by excessive cytokine production, such as by IL-1 or TNF respectively, such as inflamed joints, eczema, psoriasis and other inflammatory skin conditions such as sunburn; inflammatory eye conditions including conjunctivitis; pyresis, pain and other conditions associated with inflammation. Periodontal disease has also been implemented in cytokine production, both topically and systemically. Hence use of compounds of Formula (I) to control the inflammation associated with cytokine production in such peroral diseases such as gingivitis and periodontitis is another aspect of the present invention.

Compounds of Formula (I) have also been shown to inhibit the production of IL-8 (Interleukin-8, NAP). Accordingly, in a further aspect, this invention relates to a method of inhibiting the production of IL-8 in a mammal in need thereof which comprises administering to said mammal an effective amount of a compound of Formula (I) or a pharmaceutically acceptable salt thereof.

There are many disease states in which excessive or unregulated IL-8 production is implicated in exacerbating and/or causing the disease. These diseases are characterized by massive neutrophil infiltration such as, psoriasis, inflammatory bowel disease, asthma, cardiac, brain and renal reperfusion injury, adult respiratory distress syndrome, thrombosis and glomerulonephritis. All of these diseases are associated with increased IL-8 production which is responsible for the chemotaxis of neutrophils into the inflammatory site. In contrast to other inflammatory cytokines (IL-1, TNF, and IL-6), IL-8 has the unique property of promoting neutrophil chemotaxis and activation. Therefore, the inhibition of IL-8 production would lead to a direct reduction in the neutrophil infiltration.

The compounds of Formula (I) are administered in an amount sufficient to inhibit cytokine, in particular IL-1, IL-6, IL-8 or TNF, production such that it is regulated down to normal levels, or in some case to subnormal levels, so as to ameliorate or prevent the disease state. Abnormal levels of IL-1, IL-6, IL-8 or TNF, for instance in the context of the present invention, constitute: (i) levels of free (not cell bound) IL-1, IL-6, IL-8 or TNF greater than or equal to 1 picogram per ml; (ii) any cell associated IL-1, IL-6, IL-8 or TNF; or (iii)

the presence of IL-1, IL-6, IL-8 or TNF mRNA above basal levels in cells or tissues in which IL-1, IL-6, IL-8 or TNF, respectively, is produced.

The discovery that the compounds of Formula (I) are inhibitors of cytokines, specifically IL-1, IL-6, IL-8 and TNF is based upon the effects of the compounds of Formulas (I) on the production of the IL-1, IL-8 and TNF in in vitro assays which are described herein.

As used herein, the term "inhibiting the production of IL-1 (IL-6, IL-8 or TNF)" refers to:

a) a decrease of excessive in vivo levels of the cytokine (IL-1, IL-6, IL-8 or TNF) in a human to normal or sub-normal levels by inhibition of the in release of the cytokine by all cells, including but not limited to monocytes or macrophages;

b) a down regulation, at the genomic level, of excessive in vivo levels of the cytokine (IL-1, IL-6, IL-8 or TNF) in a human to normal or sub-normal levels;

c) a down regulation, by inhibition of the direct synthesis of the cytokine (IL-1, IL-6, IL-8 or TNF) as a postranslational event; or d) a down regulation, at the translational level, of excessive in vivo levels of the cytokine (IL-1, IL-6, IL-8 or TNF) in a human to normal or sub-normal levels.

As used herein, the term "TNF mediated disease or disease state" refers to any and all disease states in which TNF plays a role, either by production of TNF itself, or by TNF causing another monokine to be released, such as but not limited to IL-1, IL-6 or IL-8. A disease state in which, for instance, IL-1 is a major component, and whose production or action, is exacerbated or secreted in response to TNF, would therefore be considered a disease stated mediated by TNF.

As used herein, the term "cytokine" refers to any secreted polypeptide that affects the functions of cells and is a molecule which modulates interactions between cells in the immune, inflammatory or hematopoietic response. A cytokine includes, but is not limited to, monokines and lymphokines, regardless of which cells produce them. For instance, a monokine is generally referred to as being produced and secreted by a mononuclear cell, such as a macrophage and/or monocyte. Many other cells however also produce monokines, such as natural killer cells, fibroblasts, basophils, neutrophils, endothelial cells, brain astrocytes, bone marrow stromal cells, epideral keratinocytes and B-lymphocytes. Lymphokines are generally referred to as being produced by lymphocyte cells. Examples of cytokines include, but are not limited to, Interleukin-1 (IL-1), Interleukin-6 (IL-6), Interleukin-8 (IL-8), Tumor Necrosis Factor-alpha (TNF-α) and Tumor Necrosis Factor beta (TNF-β).

As used herein, the term "cytokine interfering" or "cytokine suppressive amount" refers to an effective amount of a compound of Formula (I) which will cause a decrease in the in vivo levels of the cytokine to normal or sub-normal levels, when given to a patient for the prophylaxis or treatment of a disease state which is exacerbated by, or caused by, excessive or unregulated cytokine production.

As used herein, the cytokine referred to in the phrase "inhibition of a cytokine, for use in the treatment of a HIV-infected human" is a cytokine which is implicated in (a) the initiation and/or maintenance of T cell activation and/or activated T cell-mediated HIV gene expression and/or replication and/or (b) any cytokine-mediated disease associated problem such as cachexia or muscle degeneration.

As TNF-β (also known as lymphotoxin) has close structural homology with TNF-α (also known as cachectin) and since each induces similar biologic responses and binds to the same cellular receptor, both TNF-α and TNF-β are inhibited by the compounds of the present invention and thus are herein referred to collectively as "TNF" unless specifically delineated otherwise.

A member of the MAP kinase family, alternatively termed CSBP, p38, or RK, has been identified independently by several laboratories. Activation of this novel protein kinase via dual phosphorylation has been observed in different cell systems upon stimulation by a wide spectrum of stimuli, such as physicochemical stress and treatment with lipopolysaccharide or proinflammatory cytokines such as interleukin-1 and tumor necrosis factor. The cytokine biosynthesis inhibitors, of the present invention, compounds of Formula (I) have been determined to be potent and selective inhibitors of CSBP/p38/RK kinase activity. It has been found that some p38 compounds exhibit reversible time-dependent inhibition of the p38 kinase due to the kinetics of slow binding and/or slow dissociation, resulting in an improved apparent IC50 when a compound has been preincubated with the enzyme or with cells. This slow, tight binding property may contribute to enhanced potency of such compounds both in vitro and in vivo.

These inhibitors are of aid in determining the signaling pathways involvement in inflammatory responses. In particular, for the first time a definitive signal transduction pathway can be prescribed to the action of lipopolysaccharide in cytokine production in macrophages. In addition to those diseases already noted, treatment of stroke, neurotrauma, cardiac and renal reperfusion injury, congestive heart failure, coronary arterial bypass grafting (CABG) surgery, chronic renal failure, angiogenesis & related processes, such as cancer, thrombosis, glomerulonephritis, diabetes and pancreatic β cells, multiple sclerosis, muscle degeneration, eczema, psoriasis, sunburn, and conjunctivitis are also included.

The CSBP inhibitors were subsequently tested in a number of animal models for anti-inflammatory activity. Model systems were chosen that were relatively insensitive to cyclooxygenase inhibitors in order to reveal the unique activities of cytokine suppressive agents. The inhibitors exhibited significant activity in many such in vivo studies. Most notable are its effectiveness in the collagen-induced arthritis model and inhibition of TNF production in the endotoxic shock model. In the latter study, the reduction in plasma level of TNF correlated with survival and protection from endotoxic shock related mortality. Also of great importance are the compounds effectiveness in inhibiting bone resorption in a rat fetal long bone organ culture system. Griswold et al., (1988) *Arthritis Rheum*. 31:1406-1412; Badger, et al., (1989) *Circ. Shock* 27, 51-61; Votta et al., (1994) *in vitro. Bone* 15,533-538; Lee et al., (1993). B *Ann. N.Y. Acad. Sci.* 696, 149-170.

Chronic diseases which have an inappropriate angiogenic component are various ocular neovasularizations, such as diabetic retinopathy and macular degeneration. Other chronic diseases which have an excessive or increased proliferation of vasculature are tumor growth and metastasis, atherosclerosis, and certain arthritic conditions. Therefore CSBP kinase inhibitors will be of utility in the blocking of the angiogenic component of these disease states.

The term "excessive or increased proliferation of vasculature inappropriate angiogenesis" as used herein includes, but is not limited to, diseases which are characterized by hemangiomas and ocular diseases.

The term "inappropriate angiogenesis" as used herein includes, but is not limited to, diseases which are characterized by vesicle proliferation with accompanying tissue proliferation, such as occurs in cancer, metastasis, arthritis and atherosclerosis.

Accordingly, the present invention provides a method of treating a CSBP kinase mediated disease in a mammal in need thereof, preferably a human, which comprises administering to said mammal, an effective amount of a compound of Formula (I) or a pharmaceutically acceptable salt thereof.

In order to use a compound of Formula (I) or a pharmaceutically acceptable salt thereof in therapy, it will normally be formulated into a pharmaceutical composition in accordance with standard pharmaceutical practice. This invention, therefore, also relates to a pharmaceutical composition comprising an effective, non-toxic amount of a compound of Formula (I) and a pharmaceutically acceptable carrier or diluent.

Compounds of Formula (I), pharmaceutically acceptable salts thereof and pharmaceutical compositions incorporating such may conveniently be administered by any of the routes conventionally used for drug administration, for instance, orally, topically, parenterally or by inhalation. The compounds of Formula (I) may be administered in conventional dosage forms prepared by combining a compound of Formula (I) with standard pharmaceutical carriers according to conventional procedures. The compounds of Formula (I) may also be administered in conventional dosages in combination with a known, second therapeutically active compound. These procedures may involve mixing, granulating and compressing or dissolving the ingredients as appropriate to the desired preparation. It will be appreciated that the form and character of the pharmaceutically acceptable character or diluent is dictated by the amount of active ingredient with which it is to be combined, the route of administration and other well-known variables. The carrier(s) must be "acceptable" in the sense of being compatible with the other ingredients of the formulation and not deleterious to the recipient thereof.

The pharmaceutical carrier employed may be, for example, either a solid or liquid. Exemplary of solid carriers are lactose, terra alba, sucrose, talc, gelatin, agar, pectin, acacia, magnesium stearate, stearic acid and the like. Exemplary of liquid carriers are syrup, peanut oil, olive oil, water and the like. Similarly, the carrier or diluent may include time delay material well known to the art, such as glyceryl mono-stearate or glyceryl distearate alone or with a wax.

A wide variety of pharmaceutical forms can be employed. Thus, if a solid carrier is used, the preparation can be tableted, placed in a hard gelatin capsule in powder or pellet form or in the form of a troche or lozenge. The amount of solid carrier will vary widely but preferably will be from about 25 mg. to about 1 g. When a liquid carrier is used, the preparation will be in the form of a syrup, emulsion, soft gelatin capsule, sterile injectable liquid such as an ampule or nonaqueous liquid suspension.

Compounds of Formula (I) may be administered topically, that is by non-systemic administration. This includes the application of a compound of Formula (I) externally to the epidermis or the buccal cavity and the instillation of such a compound into the ear, eye and nose, such that the compound does not significantly enter the blood stream. In contrast, systemic administration refers to oral, intravenous, intraperitoneal and intramuscular administration.

Formulations suitable for topical administration include liquid or semi-liquid preparations suitable for penetration through the skin to the site of inflammation such as liniments, lotions, creams, ointments or pastes, and drops suitable for administration to the eye, ear or nose. The active ingredient may comprise, for topical administration, from 0.001% to 10% w/w, for instance from 1% to 2% by weight of the formulation. It may however comprise as much as 10% w/w but preferably will comprise less than 5% w/w, more preferably from 0.1% to 1% w/w of the formulation.

Lotions according to the present invention include those suitable for application to the skin or eye. An eye lotion may comprise a sterile aqueous solution optionally containing a bactericide and may be prepared by methods similar to those for the preparation of drops. Lotions or liniments for application to the skin may also include an agent to hasten drying and to cool the skin, such as an alcohol or acetone, and/or a moisturizer such as glycerol or an oil such as castor oil or arachis oil.

Creams, ointments or pastes according to the present invention are semi-solid formulations of the active ingredient for external application. They may be made by mixing the active ingredient in finely-divided or powdered form, alone or in solution or suspension in an aqueous or non-aqueous fluid, with the aid of suitable machinery, with a greasy or non-greasy base. The base may comprise hydrocarbons such as hard, soft or liquid paraffin, glycerol, beeswax, a metallic soap; a mucilage; an oil of natural origin such as almond, corn, arachis, castor or olive oil; wool fat or its derivatives or a fatty acid such as stearic or oleic acid together with an alcohol such as propylene glycol or a macrogel. The formulation may incorporate any suitable surface active agent such as an anionic, cationic or non-ionic surfactant such as a sorbitan ester or a polyoxyethylene derivative thereof. Suspending agents such as natural gums, cellulose derivatives or inorganic materials such as silicaceous silicas, and other ingredients such as lanolin, may also be included.

Drops according to the present invention may comprise sterile aqueous or oily solutions or suspensions and may be prepared by dissolving the active ingredient in a suitable aqueous solution of a bactericidal and/or fungicidal agent and/or any other suitable preservative, and preferably including a surface active agent. The resulting solution may then be clarified by filtration, transferred to a suitable container which is then sealed and sterilized by autoclaving or maintaining at 98-100° C. for half an hour. Alternatively, the solution may be sterilized by filtration and transferred to the container by an aseptic technique. Examples of bactericidal and fungicidal agents suitable for inclusion in the drops are phenylmercuric nitrate or acetate (0.002%), benzalkonium chloride (0.01%) and chlorhexidine acetate (0.01%). Suitable solvents for the preparation of an oily solution include glycerol, diluted alcohol and propylene glycol.

Compounds of Formula (I) may be administered parenterally, that is by intravenous, intramuscular, subcutaneous intranasal, intrarectal, intravaginal or intraperitoneal administration. The subcutaneous and intramuscular forms of parenteral administration are generally preferred. Appropriate dosage forms for such administration may be prepared by conventional techniques. Compounds of Formula (I) may also be administered by inhalation, that is by intranasal and oral inhalation administration. Appropriate dosage forms for such administration, such as an aerosol formulation or a metered dose inhaler, may be prepared by conventional techniques.

In one embodiment of the present invention, the agents of the present invention are delivered via oral inhalation or intranasal administration. Appropriate dosage forms for such administration, such as an aerosol formulation or a metered dose inhaler, may be prepared by conventional techniques.

For administration by inhalation the compounds may be delivered in the form of an aerosol spray presentation from pressurized packs or a nebulizer, with the use of a suitable propellant, e.g. dichlorodifluoromethane, trichlorofluoromethane, dichlorotetrafluoroethane, a hydrofluoroalkane such as tetrafluoroethane or heptafluoropropane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of a compound of the invention and a suitable powder base such as lactose or starch.

Dry powder compositions for topical delivery to the lung by inhalation may, for example, be presented in capsules and cartridges of for example gelatine, or blisters of for example laminated aluminium foil, for use in an inhaler or insufflator. Powder blend formulations generally contain a powder mix for inhalation of the compound of the invention and a suitable powder base (carrier/diluent/excipient substance) such as mono-, di or poly-saccharides (e.g. lactose or starch). Use of lactose is preferred.

Each capsule or cartridge may generally contain between 20 μg-10 mg of the compound of formula (I) or (Ia) optionally in combination with another therapeutically active ingredient. Alternatively, the compound of the invention may be presented without excipients.

Suitably, the packing/medicament dispenser is of a type selected from the group consisting of a reservoir dry powder inhaler (RDPI), a multi-dose dry powder inhaler (MDPI), and a metered dose inhaler (MDI).

By reservoir dry powder inhaler (RDPI) it is meant an inhaler having a reservoir form pack suitable for comprising multiple (un-metered doses) of medicament in dry powder form and including means for metering medicament dose from the reservoir to a delivery position. The metering means may for example comprise a metering cup, which is movable from a first position where the cup may be filled with medicament from the reservoir to a second position where the metered medicament dose is made available to the patient for inhalation.

By multi-dose dry powder inhaler (MDPI) is meant an inhaler suitable for dispensing medicament in dry powder form, wherein the medicament is comprised within a multi-dose pack containing (or otherwise carrying) multiple, define doses (or parts thereof) of medicament. In a preferred aspect, the carrier has a blister pack form, but it could also, for example, comprise a capsule-based pack form or a carrier onto which medicament has been applied by any suitable process including printing, painting and vacuum occlusion.

In the case of multi-dose delivery, the formulation can be pre-metered (e.g. as in Diskus, see GB 2242134, U.S. Pat. Nos. 6,632,666, 5,860,419, 5,873,360 and 5,590,645 or Diskhaler, see GB 2178965, 2129691 and 2169265, U.S. Pat. Nos. 4,778,054, 4,811,731, 5,035,237, the disclosures of which are hereby incorporated by reference) or metered in use (e.g. as in Turbuhaler, see EP 69715 or in the devices described in U.S. Pat. No. 6,321,747 the disclosures of which are hereby incorporated by reference). An example of a unit-dose device is Rotahaler (see GB 064336 and U.S. Pat. No. 4,353,656, the disclosures of which are hereby incorporated by reference).

The Diskus inhalation device comprises an elongate strip formed from a base sheet having a plurality of recesses spaced along its length and a lid sheet hermetically but peelably sealed thereto to define a plurality of containers, each container having therein an inhalable formulation containing a compound of formula (I) or (Ia) preferably combined with lactose. Preferably, the strip is sufficiently flexible to be wound into a roll. The lid sheet and base sheet will preferably have leading end portions which are not sealed to one another and at least one of the said leading end portions is constructed to be attached to a winding means. Also, preferably the hermetic seal between the base and lid sheets extends over their whole width. The lid sheet may preferably be peeled from the base sheet in a longitudinal direction from a first end of the said base sheet.

In one aspect, the multi-dose pack is a blister pack comprising multiple blisters for containment of medicament in dry powder form. The blisters are typically arranged in regular fashion for ease of release of medicament there from.

In one aspect, the multi-dose blister pack comprises plural blisters arranged in generally circular fashion on a disc-form blister pack. In another aspect, the multi-dose blister pack is elongate in form, for example comprising a strip or a tape.

Preferably, the multi-dose blister pack is defined between two members peelably secured to one another. U.S. Pat. Nos. 5,860,419, 5,873,360 and 5,590,645 describe medicament packs of this general type. In this aspect, the device is usually provided with an opening station comprising peeling means for peeling the members apart to access each medicament dose. Suitably, the device is adapted for use where the peelable members are elongate sheets which define a plurality of medicament containers spaced along the length thereof, the device being provided with indexing means for indexing each container in turn. More preferably, the device is adapted for use where one of the sheets is a base sheet having a plurality of pockets therein, and the other of the sheets is a lid sheet, each pocket and the adjacent part of the lid sheet defining a respective one of the containers, the device comprising driving means for pulling the lid sheet and base sheet apart at the opening station.

By metered dose inhaler (MDI) it is meant a medicament dispenser suitable for dispensing medicament in aerosol form, wherein the medicament is comprised in an aerosol container suitable for containing a propellant-based aerosol medicament formulation. The aerosol container is typically provided with a metering valve, for example a slide valve, for release of the aerosol form medicament formulation to the patient. The aerosol container is generally designed to deliver a predetermined dose of medicament upon each actuation by means of the valve, which can be opened either by depressing the valve while the container is held stationary or by depressing the container while the valve is held stationary.

Where the medicament container is an aerosol container, the valve typically comprises a valve body having an inlet port through which a medicament aerosol formulation may enter said valve body, an outlet port through which the aerosol may exit the valve body and an open/close mechanism by means of which flow through said outlet port is controllable.

The valve may be a slide valve wherein the open/close mechanism comprises a sealing ring and receivable by the sealing ring a valve stem having a dispensing passage, the valve stem being slidably movable within the ring from a valve-closed to a valve-open position in which the interior of the valve body is in communication with the exterior of the valve body via the dispensing passage.

Typically, the valve is a metering valve. The metering volumes are typically from 10 to 100 μl, such as 25 μl, 50 μl or 63 μl. Suitably, the valve body defines a metering chamber for metering an amount of medicament formulation and an open/close mechanism by means of which the flow through the inlet port to the metering chamber is controllable. Preferably, the valve body has a sampling chamber in communication with the metering chamber via a second inlet port, said inlet port being controllable by means of an open/close mechanism thereby regulating the flow of medicament formulation into the metering chamber.

The valve may also comprise a 'free flow aerosol valve' having a chamber and a valve stem extending into the chamber and movable relative to the chamber between dispensing and non-dispensing positions. The valve stem has a configuration and the chamber has an internal configuration such that a metered volume is defined there between and such that during movement between is non-dispensing and dispensing positions the valve stem sequentially: (i) allows free flow of aerosol formulation into the chamber, (ii) defines a closed metered volume for pressurized aerosol formulation between the external surface of the valve stem and internal surface of the chamber, and (iii) moves with the closed metered volume within the chamber without decreasing the volume of the closed metered volume until the metered volume communicates with an outlet passage thereby allowing dispensing of the metered volume of pressurized aerosol formulation. A valve of this type is described in U.S. Pat. No. 5,772,085. Additionally, intra-nasal delivery of the present compounds is effective.

To formulate an effective pharmaceutical nasal composition, the medicament must be delivered readily to all portions of the nasal cavities (the target tissues) where it performs its pharmacological function. Additionally, the medicament should remain in contact with the target tissues for relatively long periods of time. The longer the medicament remains in contact with the target tissues, the medicament must be capable of resisting those forces in the nasal passages that function to remove particles from the nose. Such forces, referred to as 'mucociliary clearance', are recognised as being extremely effective in removing particles from the nose in a rapid manner, for example, within 10-30 minutes from the time the particles enter the nose.

Other desired characteristics of a nasal composition are that it must not contain ingredients which cause the user discomfort, that it has satisfactory stability and shelf-life properties, and that it does not include constituents that are considered to be detrimental to the environment, for example ozone depletors.

A suitable dosing regime for the formulation of the present invention when administered to the nose would be for the patient to inhale deeply subsequent to the nasal cavity being cleared. During inhalation the formulation would be applied to one nostril while the other is manually compressed. This procedure would then be repeated for the other nostril.

A preferable means for applying the formulation of the present invention to the nasal passages is by use of a pre-compression pump. Most preferably, the pre-compression pump will be a VP7 model manufactured by Valois S A. Such a pump is beneficial as it will ensure that the formulation is not released until a sufficient force has been applied, otherwise smaller doses may be applied. Another advantage of the pre-compression pump is that atomisation of the spray is ensured as it will not release the formulation until the threshold pressure for effectively atomising the spray has been achieved. Typically, the VP7 model may be used with a bottle capable of holding 10-50 ml of a formulation. Each spray will typically deliver 50-100 µl of such a formulation; therefore, the VP7 model is capable of providing at least 100 metered doses.

Spray compositions for topical delivery to the lung by inhalation may for example be formulated as aqueous solutions or suspensions or as aerosols delivered from pressurised packs, such as a metered dose inhaler, with the use of a suitable liquefied propellant. Aerosol compositions suitable for inhalation can be either a suspension or a solution and generally contain the compound of formula (I) or (Ia) optionally in combination with another therapeutically active ingredient and a suitable propellant such as a fluorocarbon or hydrogen-containing chlorofluorocarbon or mixtures thereof, particularly hydrofluoroalkanes, e.g. dichlorodifluoromethane, trichlorofluoromethane, dichlorotetra-fluoroethane, especially 1,1,1,2-tetrafluoroethane, 1,1,1,2,3,3,3-heptafluoro-n-propane or a mixture thereof. Carbon dioxide or other suitable gas may also be used as propellant. The aerosol composition may be excipient free or may optionally contain additional formulation excipients well known in the art such as surfactants, e.g., oleic acid or lecithin and cosolvents, e.g. ethanol. Pressurised formulations will generally be retained in a canister (e.g. an aluminium canister) closed with a valve (e.g. a metering valve) and fitted into an actuator provided with a mouthpiece.

Medicaments for administration by inhalation desirably have a controlled particle size. The optimum particle size for inhalation into the bronchial system is usually 1-10 µm, preferably 2-5 µm. Particles having a size above 20 µm are generally too large when inhaled to reach the small airways. To achieve these particle sizes the particles of the active ingredient as produced may be size reduced by conventional means e.g., by micronization. The desired fraction may be separated out by air classification or sieving. Suitably, the particles will be crystalline in form. When an excipient such as lactose is employed, generally, the particle size of the excipient will be much greater than the inhaled medicament within the present invention. When the excipient is lactose it will typically be present as milled lactose, wherein not more than 85% of lactose particles will have a MMD of 60-90 µm and not less than 15% will have a MMD of less than 15 µm.

Intranasal sprays may be formulated with aqueous or non-aqueous vehicles with the addition of agents such as thickening agents, buffer salts or acid or alkali to adjust the pH, isotonicity adjusting agents or anti-oxidants.

Solutions for inhalation by nebulization may be formulated with an aqueous vehicle with the addition of agents such as acid or alkali, buffer salts, isotonicity adjusting agents or antimicrobials. They may be sterilised by filtration or heating in an autoclave, or presented as a non-sterile product.

For all methods of use disclosed herein for the compounds of Formula (I), the daily oral dosage regimen will preferably be from about 0.05 to about 80 mg/kg of total body weight, preferably from about 0.1 to 30 mg/kg, more preferably from about 0.5 mg to 15 mg/kg, administered in one or more daily doses. The daily parenteral dosage regimen about 0.1 to about 80 mg/kg of total body weight, preferably from about 0.2 to about 30 mg/kg, and more preferably from about 0.5 mg to 15 mg/kg, administered in one or more daily doses. The daily topical dosage regimen will preferably be from 0.01 mg to 150 mg, administered one to four times daily. The daily inhalation dosage regimen will be from about 0.05 microgram/kg to about 1 mg/kg per day, preferably from about 0.2 microgram/kg to about 20 microgram/kg, administered in one or more daily doses. It will also be recognized by one of skill in the art that the optimal quantity and spacing of individual dosages of a compound of Formula (I) or a pharmaceutically acceptable salt thereof will be determined by the nature and extent of the condition being treated, the form, route and site of administration, and the particular patient being treated, and that such optimums can be determined by conventional techniques. It will also be appreciated by one of skill in the art that the optimal course of treatment, i.e., the number of doses of a compound of Formula (I) or a pharmaceutically acceptable salt thereof given per day for a defined number of days, can be ascertained by those skilled in the art using conventional course of treatment determination tests.

The novel compounds of Formula (I) may also be used in association with the veterinary treatment of mammals, other than humans, in need of inhibition of CSBP/p38 or cytokine inhibition or production. In particular, CSBP/p38 mediated diseases for treatment, therapeutically or prophylactically, in animals include disease states such as those noted herein in the Methods of Treatment section, but in particular viral infections. Examples of such viruses include, but are not limited to, lentivirus infections such as, equine infectious anaemia virus, caprine arthritis virus, visna virus, or maedi virus or retrovirus infections, such as but not limited to feline immunodeficiency virus (FIV), bovine immunodeficiency virus, or canine immunodeficiency virus or other retroviral infections.

Another aspect of the present invention is a method of treating the common cold or respiratory viral infection caused by human rhinovirus (HRV), other enteroviruses, coronavirus, influenza virus, parainfluenza virus, respiratory syncytial virus, or adenovirus in a human in need thereof which method comprises administering to said human an effective amount of a CBSP/p38 inhibitor.

Another aspect of the present invention is a method of treating, including prophylaxis of influenza induced pneumonia in a human in need thereof which method comprises administering to said human an effective amount of a CBSP/p38 inhibitor The present invention also relates to the use of the CSBP/p38 kinase inhibitor for the treatment, including prophylaxis, of inflammation associated with a viral infection of a human rhinovirus (HRV), other enteroviruses, coronavirus, influenza virus, parainfluenza virus, respiratory syncytial virus, or adenovirus.

In particular, the present invention is directed to the treatment of a viral infection in a human, which is caused by the human rhinovirus (HRV), other enterovirus, coronavirus, influenza virus, parainfluenza virus, respiratory syncytial virus, or an adenovirus. In particular the invention is directed to respiratory viral infections that exacerbate asthma (induced by such infections), chronic bronchitis, chronic obstructive pulmonary disease, otitis media, and sinusitis. While inhibiting IL-8 or other cytokines may be beneficial in treating a rhinovirus may be known, the use of an inhibitor of the p38 kinase for treating HRV or other respiratory viral infections causing the common cold is believed novel.

It should be noted that the respiratory viral infection treated herein may also be associated with a secondary bacterial infection, such as otitis media, sinusitis, or pneumonia.

For use herein treatment may include prophylaxis for use in a treatment group susceptible to such infections. It may also include reducing the symptoms of, ameliorating the symptoms of, reducing the severity of, reducing the incidence of, or any other change in the condition of the patient, which improves the therapeutic outcome.

It should be noted that the treatment herein is not directed to the elimination or treatment of the viral organism itself but is directed to treatment of the respiratory viral infection that exacerbates other diseases or symptoms of disease, such as asthma (induced by such infections), chronic bronchitis, chronic obstructive pulmonary disease, otitis media, and sinusitis.

It should be understood that in addition to the ingredients particularly mentioned above, the formulations of this invention may include other agents conventional in the art having regard to the type of formulation in question, for example those suitable for oral administration may include flavouring agents.

The compounds and pharmaceutical formulations according to the invention may be used in combination with or include one or more other therapeutic agents, for example selected from anti-inflammatory agents, anticholinergic agents (particularly an $M_1$, $M_2$, $M_1/M_2$ or $M_3$ receptor antagonist), $\beta_2$-adrenoreceptor agonists, antiinfective agents (e.g. antibiotics, antivirals), or antihistamines. The invention thus provides, in a further aspect, a combination comprising a compound of formula (I) or a pharmaceutically acceptable salt, solvate or physiologically functional derivative thereof together with one or more other therapeutically active agents, for example selected from an anti-inflammatory agent (for example a corticosteroid or an NSAID), an anticholinergic agent, $\beta_2$-adrenoreceptor agonist, an antiinfective agent (e.g. an antibiotic or an antiviral), or an antihistamine. One aspect of the present invention are combinations comprising a compound of Formula (I) or a pharmaceutically acceptable salt, solvate or physiologically functional derivative thereof together with a corticosteroid, and/or an anticholinergic, and/or a PDE-4 inhibitor. Preferred combinations are those comprising one or two other therapeutic agents.

It will be clear to a person skilled in the art that, where appropriate, the other therapeutic ingredient(s) may be used in the form of salts, (e.g. as alkali metal or amine salts or as acid addition salts), or prodrugs, or as esters (e.g. lower alkyl esters), or as solvates (e.g. hydrates) to optimise the activity and/or stability and/or physical characteristics (e.g. solubility) of the therapeutic ingredient. It will be clear also that where appropriate, the therapeutic ingredients may be used in optically pure form.

Suitable anti-inflammatory agents include corticosteroids and NSAIDs. Suitable corticosteroids which may be used in combination with the compounds of the invention are those oral and inhaled corticosteroids and their pro-drugs which have anti-inflammatory activity. Examples include, but are not limited to, methyl prednisolone, prednisolone, dexamethasone, fluticasone propionate, 6α,9α-difluoro-17α-[(2-furanylcarbonyl)oxy]-11β-hydroxy-16α-methyl-3-oxo-androsta-1,4-diene-17β-carbothioic acid S-fluoromethyl ester, 6α,9α-difluoro-11β-hydroxy-16α-methyl-3-oxo-17α-propionyloxy-androsta-1,4-diene-17β-carbothioic acid S-(2-oxo-tetrahydro-furan-3S-yl) ester, beclomethasone esters (e.g. the 17-propionate ester or the 17,21-dipropionate ester), budesonide, flunisolide, mometasone esters (e.g. the furoate ester), triamcinolone acetonide, rofleponide, ciclesonide, butixocort propionate, RPR-106541, and ST-126. Preferred corticosteroids include fluticasone propionate, 6α,9α-difluoro-11β-hydroxy-16α-methyl-17α-[(4-methyl-1,3-thiazole-5-carbonyl)oxy]-3-oxo-androsta-1,4-diene-17β-carbothioic acid S-fluoromethyl ester and 6α,9α-difluoro-17α-[(2-furanylcarbonyl)oxy]-11β-hydroxy-16α-methyl-3-oxo-androsta-1,4-diene-17β-carbothioic acid S-fluoromethyl ester, more preferably 6α,9α-difluoro-17α-[(2-furanylcarbonyl)oxy]-11β-hydroxy-16α-methyl-3-oxo-androsta-1,4-diene-17β-carbothioic acid S-fluoromethyl ester.

Suitable NSAIDs include sodium cromoglycate, nedocromil sodium, phosphodiesterase (PDE) inhibitors (e.g. theophylline, PDE4 inhibitors or mixed PDE3/PDE4 inhibitors), leukotriene antagonists, inhibitors of leukotriene synthesis, iNOS inhibitors, tryptase and elastase inhibitors, beta-2 integrin antagonists and adenosine receptor agonists or antagonists (e.g. adenosine 2a agonists), cytokine antagonists (e.g. chemokine antagonists) or inhibitors of cytokine synthesis. Suitable other $\beta_2$-adrenoreceptor agonists include salmeterol (e.g. as the xinafoate), salbutamol (e.g. as the sulphate or the free base), formoterol (e.g. as the fumarate), fenoterol or terbutaline and salts thereof.

Another embodiment of the invention is the use of the compound of a Formula (I) or (Ia) in combination with a phosphodiesterase 4 (PDE4) inhibitor or a mixed PDE3/PDE4 inhibitor. The PDE4-specific inhibitor useful in this aspect of the invention may be any compound that is known to inhibit the PDE4 enzyme or which is discovered to act as a PDE4 inhibitor, and which are only PDE4 inhibitors, not compounds which inhibit other members of the PDE family as well as PDE4. Generally it is preferred to use a PDE4 inhibitor which has an $IC_{50}$ ratio of about 0.1 or greater as regards the $IC_{50}$ for the PDE4 catalytic form which binds rolipram with a high affinity divided by the $IC_{50}$ for the form which binds rolipram with a low affinity. For the purposes of this disclosure, the cAMP catalytic site which binds R and S rolipram with a low affinity is denominated the "low affinity" binding site (LPDE 4) and the other form of this catalytic site which binds rolipram with a high affinity is denominated the "high affinity" binding site (HPDE 4). This term "HPDE4" should not be confused with the term "hPDE4" which is used to denote human PDE4.

A method for determining $IC_{50}$s ratios is set out in U.S. Pat. No. 5,998,428 which is incorporated herein in full by reference as though set out herein. See also PCT application WO 00/51599 for another description of said assay. In one embodiment, PDE4 inhibitors of use in this invention will be those compounds which have a salutary therapeutic ratio, i.e., compounds which preferentially inhibit cAMP catalytic activity where the enzyme is in the form that binds rolipram with a low affinity, thereby reducing the side effects which apparently are linked to inhibiting the form which binds rolipram with a high affinity. Another way to state this is that the compounds will have an $IC_{50}$ ratio of about 0.1 or greater as regards the $IC_{50}$ for the PDE4 catalytic form which binds rolipram with a high affinity divided by the $IC_{50}$ for the form which binds rolipram with a low affinity.

A further refinement of this standard is that of one wherein the PDE4 inhibitor has an $IC_{50}$ ratio of about 0.1 or greater; said ratio is the ratio of the $IC_{50}$ value for competing with the binding of 1 nM of [$^3$H]R-rolipram to a form of PDE4 which binds rolipram with a high affinity over the $IC_{50}$ value for inhibiting the PDE4 catalytic activity of a form which binds rolipram with a low affinity using 1 µM[$^3$H]-cAMP as the substrate.

Suitable PDE compounds are cis 4-cyano-4-(3-cyclopentyloxy-4-methoxyphenyl)cyclohexan-1-carboxylic acid, 2-carbomethoxy-4-cyano-4-(3-cyclopropylmethoxy-4-difluoromethoxyphenyl)cyclohexan-1-one and cis-[4-cyano-4-(3-cyclopropylmethoxy-4-difluoromethoxyphenyl)cyclohexan-1-ol]; these are examples of compounds which bind preferentially to the low affinity binding site and which have an $IC_{50}$ ratio of 0.1 or greater.

Other compounds of interest include: Compounds set out in U.S. Pat. No. 5,552,438 issued 03 Sep. 1996; this patent and the compounds it discloses are incorporated herein in full by reference. The compound of particular interest, which is disclosed in U.S. Pat. No. 5,552,438, is cis-4-cyano-4-[3-(cyclopentyloxy)-4-methoxyphenyl]cyclohexane-1-carboxylic acid (also known as cilomalast) and its salts, esters, pro-drugs or physical forms; AWD-12-281 from elbion (Hofgen, N. et al. 15th EFMC Int. Symp. Med. Chem. (September 6-10, Edinburgh) 1998, Abst. P.98; CAS reference No. 247584020-9); a 9-benzyladenine derivative nominated NCS-613 (INSERM); D-4418 from Chiroscience and Schering-Plough; a benzodiazepine PDE4 inhibitor identified as CI-1018 (PD-168787) and attributed to Pfizer; a benzodioxole derivative disclosed by Kyowa Hakko in WO99/16766; K-34 from Kyowa Hakko; V-11294A from Napp (Landells, L. J. et al. Eur Resp J [Annu Cong Eur Resp Soc (September 19-23, Geneva) 1998] 1998, 12 (Suppl. 28): Abst P2393); roflumilast (CAS reference No 162401-32-3) and a pthalazinone (WO99/47505, the disclosure of which is hereby incorporated by reference) from Byk-Gulden; Pumafentrine, (−)-p-[(4aR*,10bS*)-9-ethoxy-1,2,3,4,4a,10b-hexahydro-8-methoxy-2-methylbenzo[c][1,6]naphthyridin-6-yl]-N,N-diisopropylbenzamide which is a mixed PDE3/PDE4 inhibitor which has been prepared and published on by Byk-Gulden, now Altana; arofylline under development by Almirall-Prodesfarma; VM554/UM565 from Vernalis; or T-440 (Tanabe Seiyaku; Fuji, K. et al. J Pharmacol Exp Ther, 1998, 284(1): 162), and T2585. Other possible PDE-4 and mixed PDE3/PDE4 inhibitors include those listed in WO01/13953, the disclosure of which is hereby incorporated by reference.

Suitable anticholinergic agents are those compounds that act as antagonists at the muscarinic receptor, in particular those compounds which are antagonists of the $M_1$ and $M_2$ receptors. Exemplary compounds include the alkaloids of the belladonna plants as illustrated by the likes of atropine, scopolamine, homatropine, hyoscyamine; these compounds are normally administered as a salt, being tertiary amines. These drugs, particularly the salt forms, are readily available from a number of commercial sources or can be made or prepared from literature data via, to wit:

Atropine—CAS-51-55-8 or CAS-51-48-1 (anhydrous form), atropine sulfate—CAS-5908-99-6; atropine oxide—CAS-4438-22-6 or its HCl salt—CAS-4574-60-1 and methylatropine nitrate—CAS-52-88-0; Homatropine—CAS-87-00-3, hydrobromide salt—CAS-51-56-9, methylbromide salt—CAS-80-49-9; Hyoscyamine (d, l)—CAS-101-31-5, hydrobromide salt—CAS-306-03-6 and sulfate salt—CAS-6835-16-1; and Scopolamine—CAS-51-34-3, hydrobromide salt—CAS-6533-68-2, methylbromide salt—CAS-155-41-9.

Suitable anticholinergics for use herein include, but are not limited to, ipratropium (e.g. as the bromide), sold under the name Atrovent, oxitropium (e.g. as the bromide) and tiotropium (e.g. as the bromide) (CAS-139404-48-1). Also of interest are: methantheline (CAS-53-46-3), propantheline bromide (CAS-50-34-9), anisotropine methyl bromide or Valpin 50 (CAS-80-50-2), clidinium bromide (Quarzan, CAS-3485-62-9), copyrrolate (Robinul), isopropamide iodide (CAS-71-81-8), mepenzolate bromide (U.S. Pat. No. 2,918,408), tridihexethyl chloride (Pathilone, CAS-4310-35-4), and hexocyclium methylsulfate (Tral, CAS-115-63-9). See also cyclopentolate hydrochloride (CAS-5870-29-1), tropicamide (CAS-1508-75-4), trihexyphenidyl hydrochloride (CAS-144-11-6), pirenzepine (CAS-29868-97-1), telenzepine (CAS-80880-90-9), AF-DX 116, or methoctramine, and the compounds disclosed in WO01/04118, the disclosure of which is hereby incorporated by reference.

Suitable antihistamines (also referred to as $H_1$-receptor antagonists) include any one or more of the numerous antagonists known which inhibit $H_1$-receptors, and are safe for human use. All are reversible, competitive inhibitors of the interaction of histamine with $H_1$-receptors. The majority of these inhibitors, mostly first generation antagonists, have a core structure, which can be represented by the following formula:

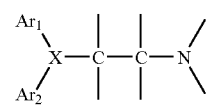

This generalized structure represents three types of antihistamines generally available: ethanolamines, ethylenediamines, and alkylamines. In addition, other first generation antihistamines include those which can be characterized as based on piperizine and phenothiazines. Second generation antagonists, which are non-sedating, have a similar structure-activity relationship in that they retain the core ethylene group (the alkylamines) or mimic the tertiary amine group with piperizine or piperidine. Exemplary antagonists are as follows:

Ethanolamines: carbinoxamine maleate, clemastine fumarate, diphenylhydramine hydrochloride, and dimenhydrinate.

Ethylenediamines: pyrilamine amleate, tripelennamine HCl, and tripelennamine citrate.

Alkylamines: chloropheniramine and its salts such as the maleate salt, and acrivastine.

Piperazines: hydroxyzine HCl, hydroxyzine pamoate, cyclizine HCl, cyclizine lactate, meclizine HCl, and cetirizine HCl.

Piperidines: Astemizole, levocabastine HCl, loratadine or its descarboethoxy analogue, and terfenadine and fexofenadine hydrochloride or another pharmaceutically acceptable salt.

Azelastine hydrochloride is yet another $H_1$ receptor antagonist which may be used in combination with a PDE4 inhibitor.

The combinations referred to above may conveniently be presented for use in the form of a pharmaceutical formulation and thus pharmaceutical formulations comprising a combination as defined above together with a physiologically acceptable diluent or carrier represent a further aspect of the invention.

The individual compounds of such combinations may be administered either sequentially or simultaneously in separate or combined pharmaceutical formulations. Appropriate doses of known therapeutic agents will be readily appreciated by those skilled in the art.

The invention will now be described by reference to the following biological examples, which are merely illustrative and are not to be construed as a limitation of the scope of the present invention.

BIOLOGICAL EXAMPLES

The cytokine-inhibiting effects of compounds of the present invention may be determined by the following in vitro assays:

Assays for Interleukin-1 (IL-1beta), Interleukin-8 (IL-8), and Tumour Necrosis Factor (TNFalpha) are well known in the art, and may be found in a number of publications, and patents. Representative suitable assays for use herein are described in Adams et al., U.S. Pat. No. 5,593,992, whose disclosure is incorporated by reference in its entirety.

It is recognized that the respective assays herein may have been run multiple times for particular compounds of Formula (I) or (Ia), etc. as described herein. The determination of activity, as reported in these assays, will be based upon a mean or median of these values.

Interleukin-1 (IL-1)

Human peripheral blood monocytes are isolated and purified from either fresh blood preparations from volunteer donors, or from blood bank buffy coats, according to the procedure of Colotta et al, J Immunol, 132, 936 (1984), or another suitable procedure such as positive selection selection using MACS CD14+beads. These monocytes ($1 \times 10^6$) are plated in 24, 48, 96 or 384-well plates at a concentration of 1-2 million/ml per well. The cells are allowed to adhere for 2 hours, after which time non-adherent cells can be removed by gentle washing. Test compounds are then added to the cells for 1 h before the addition of lipopolysaccharide (50-200 ng/ml), and the cultures are incubated at 37° C. for an additional 24 h. At the end of this period, culture supernatants are removed and clarified of cells and all debris. IL-1beta levels in the cell-free supernatant are then determined by enzyme-linked immunoassay (ELISA) or other antibody based procedure.

In Vivo TNF Assay:

(I) Griswold et al., Drugs Under Exp. and Clinical Res., XIX (6), 243-248 (1993); or (2) Boehm, et al., *Journal of Medicinal Chemistry* 39, 3929-3937 (1996) whose disclosures are incorporated by reference herein in their entirety.

LPS-Induced TNFα Production in Mice and Rats

In order to evaluate in vivo inhibition of LPS-induced TNFα production in rodents, both mice or rats are injected with LPS.

Mouse Method

Male Balb/c mice from Charles River Laboratories are pretreated (30 minutes) with compound or vehicle. After the 30 min. pretreat time, the mice are given LPS (lipopolysaccharide from *Esherichia coli* Serotype 055-B5, Sigma Chemical Co., St Louis, Mo.) 25 ug/mouse in 25 ul phosphate buffered saline (pH 7.0) intraperitoneally. Two hours later the mice are killed by $CO_2$ inhalation and blood samples are collected by exsanguination into heparinized blood collection tubes and stored on ice. The blood samples are centrifuged and the plasma collected and stored at −20° C. until assayed for TNFα by ELISA.

Rat Method

Male Lewis rats from Charles River Laboratories are pretreated at various times with compound or vehicle. After a determined pretreat time, the rats are given LPS (lipopolysaccharide from *Esherichia coli* Serotype 055-B5, Sigma Chemical Co., St Louis, Mo.) 3.0 mg/kg intraperitoneally. The rats are killed by $CO_2$ inhalation and heparinized whole blood is collected from each rat by cardiac puncture 90 minutes after the LPS injection. The blood samples are centrifuged and the plasma collected for analysis by ELISA for TNFα levels.

ELISA Method

TNFα levels were measured using a sandwich ELISA, Olivera et al., Circ. Shock, 37, 301-306, (1992), whose disclosure is incorporated by reference in its entirety herein, using a hamster monoclonal antimurine TNFα (Genzyme, Boston, Mass.) as the capture antibody and a polyclonal rabbit antimurine TNFa (Genzyme) as the second antibody. For detection, a peroxidase-conjugated goat antirabbit antibody (Pierce, Rockford, Ill.) was added, followed by a substrate for peroxidase (1 mg/ml orthophenylenediamine with 1% urea peroxide). TNFα levels in the plasma samples from each animal were calculated from a standard curve generated with recombinant murine TNFα (Genzyme).

LPS-Stimulated Cytokine Production in Human Whole Blood

Assay: Test compound concentrations were prepared at 10× concentrations and LPS prepared at 1 ug/ml (final conc. of 50 ng/ml LPS) and added in 50 uL volumes to 1.5 mL eppendorf tubes. Heparinized human whole blood was obtained from healthy volunteers and was dispensed into eppendorf tubes or multiwell plates containing compounds and LPS in 0.2-0.4 mL volumes and the tubes incubated at 37 C. In some studies, compound was incubated with blood for up to 30 min prior to addition of LPS. Following a 4 hour incubation, the tubes or plates were centrifuged to remove cells and plasma was withdrawn and frozen at −80 C.

Cytokine measurement: IL-Ibeta and/or TNFalpha were quantified using a standardized ELISA, or similar technology. Concentrations of IL-1beta or TNFalpha were determined from standard curves of the appropriate cytokine and IC50 values for test compound (concentration that inhibited 50% of LPS-stimulated cytokine production) were calculated by linear regression analysis.

Results

Compounds would be considered active in this assay if they demonstrated an IC50 of less than 10 uM up to about an IC50 of less than 0.0001 uM.

A representative compound of Formula (I), Example 10 was tested and found active in this assay.

CSBP/p38 Kinase Assay:

This assay measures the CSBP/p38-catalyzed transfer of $^{32}P$ from [$\alpha$-$^{32}P$]ATP to threonine residue in an epidermal growth factor receptor (EGFR)-derived peptide (T669) with the following sequence: KRELVEPLTPSGEAPNQALLR (residues 661-681). (See Gallagher et al., "Regulation of Stress Induced Cytokine Production by Pyridinyl Imidazoles: Inhibition of CSBP Kinase", BioOrganic & Medicinal Chemistry, 1997, 5, 49-64).

Reactions are carried in round bottom 96 well plate (from Corning) in a 30 ml volume. Reactions contain (in final concentration): 25 mM Hepes, pH 7.5; 8 mM $MgCl_2$; 0.17 mM ATP (the $Km_{[ATP]}$ of p38 (see Lee et al., Nature 300, n72 pg. 639-746 (December 1994)); 2.5 uCi of [γ-32P]ATP; 0.2 mM sodium orthovanadate; 1 mM DTT; 0.1% BSA; 10% glycerol; 0.67 mM T669 peptide; and 2-4 nM of yeast-expressed, activated and purified p38. Reactions are initiated by the addition of [gamma-32P]Mg/ATP, and incubated for 25 min. at 37° C. Inhibitors (dissolved in DMSO) are incubated with the reaction mixture on ice for 30 minutes prior to adding the 32P-ATP. Final DMSO concentration was 0.16%. Reactions are terminated by adding 10 ul of 0.3 M phosphoric acid, and phosphorylated peptide was isolated from the reactions by capturing it on p81 phosphocellulose filters. Filters are washed with 75 mM phosphoric acids, and incorporated 32P was quantified using beta scintillation counter. Under these conditions, the specific activity of p38 will be determined and is generally 400-450 pmol/pmol enzyme, and the activity being linear for up to 2 hours of incubation. The kinase activity values are obtained after subtracting values generated in the absence of substrate which were 10-15% of total values.

Results

Compounds would be considered active in this assay if they demonstrate an $IC_{50}$ of less than 16.7 uM to an $IC_{50}$ less than 0.0001 uM. Representative compounds of Formula I and (Ia) as described in Examples 10-12 were tested in the above assay and found active.

Fluorescence Anisotropy Kinase Binding Assay—Standard Volume

The kinase enzyme, fluorescent ligand and a variable concentration of test compound are incubated together to reach thermodynamic equilibrium under conditions such that in the absence of test compound the fluorescent ligand is significantly (>50%) enzyme bound and in the presence of a sufficient concentration (>10×$K_i$) of a potent inhibitor the anisotropy of the unbound fluorescent ligand is measurably different from the bound value.

The concentration of kinase enzyme should preferably be $\geq 2\times K_f$. The concentration of fluorescent ligand required will depend on the instrumentation used, and the fluorescent and physicochemical properties. The concentration used must be lower than the concentration of kinase enzyme, and preferably less than half the kinase enzyme concentration.

The fluorescent ligand is the following compound:

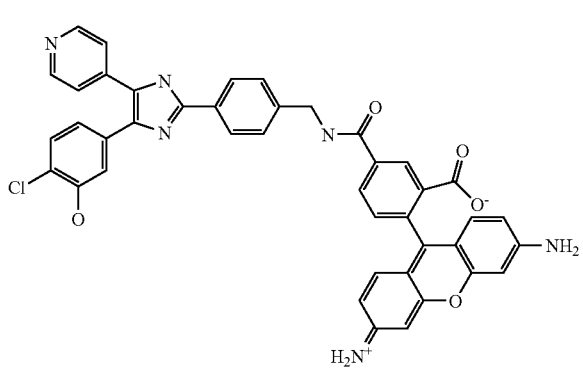

which is derived from 5-[2-(4-aminomethylphenyl)-5-pyridin-4-yl-1H-imidazol-4-yl]-2-chlorophenol and rhodamine green.

Recombinant human p38α was expressed as a GST-tagged protein. To activate this protein, 3.5 μM unactivated p38α was incubated in 50 mM Tris-HCl pH 7.5, 0.1 mM EGTA, 0.1% 2-mercaptoethanol, 0.1 mM sodium vanadate, 10 mM MgAc, 0.1 mM ATP with 200 nM MBP-MKK6 DD at 30 degrees for 30 mins. Following activation p38α was re-purified and the activity assessed using a standard filter-binding assay.

Protocol: All components are dissolved in buffer of composition 62.5 mM HEPES, pH 7.5, 1.25 mM CHAPS, 1 mM DTT, 12.5 mM $MgCl_2$ with final concentrations of 12 nM p38α and 5 nM fluorescent ligand. 30 μl of this reaction mixture is added to wells containing 1 μl of various concentrations of test compound (0.28 nM-16.6 μM final) or DMSO vehicle (3% final) in NUNC 384 well black microtitre plate and equilibrated for 30-60 mins at room temperature. Fluorescence anisotropy is read in Molecular Devices Acquest (excitation 485 nm/emission 535 nm).

Definitions: Ki=dissociation constant for inhibitor binding
Kf=dissociation constant for fluorescent ligand binding Fluorescence Anisotropy Kinase Binding Low Volume Assay The kinase enzyme, fluorescent ligand and a variable concentration of test compound are incubated together to reach thermodynamic equilibrium under conditions such that in the absence of test compound the fluorescent ligand is significantly (>50%) enzyme bound and in the presence of a sufficient concentration (>10×Ki) of a potent inhibitor the anisotropy of the unbound fluorescent ligand is measurably different from the bound value.

The concentration of kinase enzyme should preferably be 2×Kf. The concentration of fluorescent ligand required will depend on the instrumentation used, and the fluorescent and physicochemical properties. The concentration used must be lower than the concentration of kinase enzyme, and preferably less than half the kinase enzyme concentration.

The fluorescent ligand is the following compound:

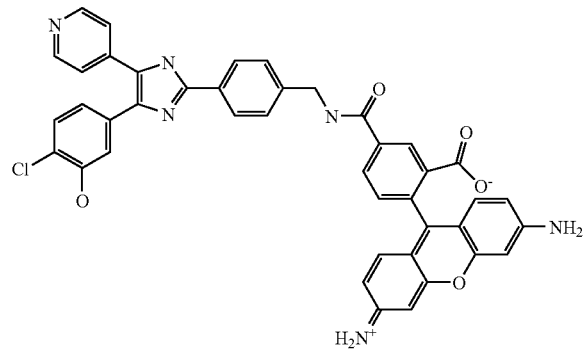

which is derived from 5-[2-(4-aminomethylphenyl)-5-pyridin-4-yl-1H-imidazol-4-yl]-2-chlorophenol and rhodamine green.

Recombinant human p38α was expressed as a GST-tagged protein. To activate this protein, 3.5 μM unactivated p38α was incubated in 50 mM Tris-HCl pH 7.5, 0.1 mM EGTA, 0.1% 2-mercaptoethanol, 0.1 mM sodium vanadate, 10 mM MgAc, 0.1 mM ATP with 200 nM MBP-MKK6 DD at 30 degrees for 30 mins. Following activation p38α was re-purified and the activity assessed using a standard filter-binding assay.

Protocol: All components are dissolved in buffer of composition 62.5 mM HEPES, pH 7.5, 1.25 mM CHAPS, 1 mM DTT, 12.5 mM $MgCl_2$ with final concentrations of 12 nM p38α and 5 nM fluorescent ligand. 30 μl of this reaction mixture is added to wells containing 0.1 μl of various concentrations of test compound (0.02 nM-25 μM final) or DMSO vehicle (1.7% final) in Greiner low volume 384 well black microtitre plate and equilibrated for 30-60 mins at room temperature. Fluorescence anisotropy is read in Molecular Devices Acquest (excitation 485 nm/emission 535 nm).

Definitions: Ki=dissociation constant for inhibitor binding
Kf=dissociation constant for fluorescent ligand binding It is noted that there are two assay formats shown above for the Fluorescence anisotropy kinase binding assay. The only difference between these two assays is the volume used and the plate type. It has been demonstrated that there is no difference in potency between the two formats, and that the assays are considered to be equivalent. The results described herein may have been performed in either assay format and are not differentiated as to which.

Results

Compounds would be considered active in this assay if they demonstrate a $pIC_{50}$ of greater than 4.6 up to a $pIC_{50}$ of greater than 9.0. Representative compounds of Formula (I) and (Ia) as described in Examples 10-12, 13(d), 14(e), 15(c), and 16(c) were tested in the above assay and found active.

TR-FRET ASSAY

Time-Resolved Fluorescence Resonance Energy Transfer Kinase Standard Assay

Recombinant human p38α is expressed as a His-tagged protein. To activate this protein, 3 μM unactivated p38α is incubated in 200 mM Hepes pH7.4, 625 mM NaCl, 1 mM DTT with 27 nM active MKK6 (Upstate), 1 mM ATP and 10 mM $MgCl_2$. The activity of the MKK6-activated p38α is assessed using a time-resolved fluorescence resonance energy transfer (TR-FRET) assay.

Biotinylated-GST-ATF2 (residues 19-96, 400 nM final), ATP (125M final) and MgCl2 (5 mM final) in assay buffer (40 mM HEPES pH 7.4, 1 mM DTT) is added to wells containing 1 ul of various concentrations of compound or DMSO vehicle (3% final) in NUNC 384 well black plate. The reaction is initiated by the addition of MKK6-activated p38 (100 pM final) to give a total volume of 30 ul. The reaction is incubated for 120 minutes at room temperature, then terminated by the addition of 15 μl of 100 mM EDTA pH 7.4. Detection reagent (15 μl) in buffer (100 mM HEPES pH 7.4, 150 mM NaCl, 0.1% w/v BSA, 1 mM DTT) containing antiphosphothreonine-ATF2-71 polyclonal antibody (Cell Signalling Technology, Beverly Mass., USA) labelled with W-1024 europium chelate (Wallac O Y, Turku, Finland), and APC-labelled streptavidin (Prozyme, San Leandro, Calif., USA) is added and the reaction was further incubated for 60 minutes at room temperature. The degree of phosphorylation of GST-ATF2 was measured using a Packard Discovery plate reader (Perkin-Elmer Life Sciences, Pangbourne, UK) as a ratio of specific 665 nm energy transfer signal to reference europium 620 nm signal.

Time-Resolved Fluorescence Resonance Energy Transfer Kinase Low Volume Assay

Recombinant human p38α is expressed as a His-tagged protein. To activate this protein, 3 μM unactivated p38α is incubated in 200 mM Hepes pH7.4, 625 mM NaCl, 1 mM DTT with 27 nM active MKK6 (Upstate), 1 mM ATP and 10 mM $MgCl_2$ The activity of the MKK6-activated p38α was assessed using a time-resolved fluorescence resonance energy transfer (TR-FRET) assay.

Biotinylated-GST-ATF2 (residues 19-96, 400 nM final), ATP (125 μM final) and $MgCl_2$ (5 mM final) in assay buffer (40 mM HEPES pH 7.4, 1 mM DTT) are added to wells containing 0.1 μl of various concentrations of compound or DMSO vehicle (1.7% final) in Greiner low volume 384 well black plate. The reaction is initiated by the addition of MKK6-activated p38α (100 pM final) to give a total volume of 6 μl. The reaction is incubated for 120 minutes at room temperature, then terminated by the addition of 3 μl of detection reagent in buffer (100 mM HEPES pH 7.4, 150 mM NaCl, 0.1% w/v BSA, 1 mM DTT, 100 mM EDTA) containing antiphosphothreonine-ATF2-71 polyclonal antibody (Cell Signalling Technology, Beverly Mass., USA) labelled with W-1024 europium chelate (Wallac O Y, Turku, Finland), and APC-labelled streptavidin (Prozyme, San Leandro, Calif., USA). The reaction is further incubated for 60 minutes at room temperature. The degree of phosphorylation of GST-ATF2 is measured using a BMG Rubystar plate reader (BMG, UK) as a ratio of specific 665 nm energy transfer signal to reference europium 620 nm signal.

It is noted that there are two assay formats shown above for the Time-resolved fluorescence resonance energy transfer kinase assay. The only difference between these two assays is the volume used and the plate type. It has been demonstrated that there is no difference in potency between the two formats, and that the assays are considered to be equivalent. Reported results may have been performed in either assay format and are not differentiated as to which.

TNF-Stimulated IL-8 Production from Human Neutrophils

The effect of test compounds on TNF-stimulated IL8 production by human neutrophils is measured as follows. Neutrophils are prepared from blood obtained from consenting donors, using standard methods. Blood is collected in heparinized syringes and layered over histopaque (30 ml/20 ml).

Following centrifugation, the red cell pellet is resuspended in PBS and purified over a dextran gradient. Red blood cells are lysed with water for 40 sec, remaining granulocytes collected by centrifugation and resuspended at 1.5×10^6 cells/ml. Cells are added (0.5-1 ml) to 48 well plates already containing compound at 1000× final concentration in neat DMSO or 10% DMSO in RPMI1640 with 10% FBS. TNF (final concentration 100 ng/ml) is used as the stimulus. Cells incubated for approximately 20 hrs at 37° C., 5% CO2. Levels of IL-8 in the cell free supernatant are determined by sandwich ELISA, and inhibition relative to a control with DMPO but no compound is calculated.

Results

Compounds would be considered active in this assay if they demonstrated a IC50 of less than 10 uM up to about an IC50 of less than 0.0001 uM.

Compound of Formula (I) and (Ia) as described in Example 10 was tested in the above assay and found active.

Rat LPS Neutrophilia Model

The effect of compounds on the influx of neutrophils to the lung in LPS-challenged rats is evaluated as follows. The test compound is suspended in one of the following solutions: 0.5% tween 80/PBS, 0.5% tween 80/saline, 10% EtOH/saline (with pH adjusted to 2.0, or 8.0 with HCl, or unadjusted), Saline@pH 2.0, 6.5 or 8.0, 0.5% Tragacanth, 1% DMSO/20% Encapsin/Saline, or acidified 5% Tragacanth. The suspension process may be aided by the use of a glass homogenizer. For intratracheal administration, the animals are anesthetized with inhaled isoflurane and placed in a supine position, the trachea is intubated with a steel gavage needle (1.5 inch, 22 gauge, small ball) or a Penn-Century Microsprayer Aerosolizer (model IA-1B) and 200 ul of dosing solution is delivered. The animals are visually monitored during the recovery process, which typically occurs within two minutes. It is noted that the test compounds may be alternatively administered via the microsprayer in a dry powder blend with a suitable excipient, such as lactose.

Rats treated with compound or vehicle (15 min-24 hours pretreatment) are exposed to an LPS aerosol (100 ug/ml) for 15 min. Four hours later the rats are euthanized with pentobarbital (100 mg/kg, i.p.) and the airways are lavaged with 5 washes of 5 ml of phosphate buffered saline. The harvested cells are stained (Diffquick) and counted to determine total and differential cell data. In a typical study, macrophages represent 40-70% of the total cells, and polymorphonuclear cells 30-60% of the total cells. Inhibition of neutrophil levels relative to no compound controls is calculated based on the differential counts.

The assay has varying conditions, such as concentration, pretreat time, form of the compound (crystalline, amorphous, salts, micronised), and a wet or dry application of the compound.

The data is obtained as % inhibition using a particular concentration and pretreat time. While a number of the compounds were found to be statistically nonsignificant (p>0.05), it is expected that upon retesting with either increasing concentrations, and/or a change in pretreat time that some of them may reach statistical significance (p<0.05).

TNF-α in Traumatic Brain Injury Assay

This assay provides for examination of the expression of tumor necrosis factor mRNA in specific brain regions which follow experimentally induced lateral fluid-percussion traumatic brain injury (TBI) in rats. Since TNF-α is able to induce nerve growth factor (NGF) and stimulate the release of other cytokines from activated astrocytes, this post-traumatic alteration in gene expression of TNF-α plays an important role in both the acute and regenerative response to CNS trauma. A suitable assay may be found in WO 97/35856 whose disclosure is incorporated herein by reference.

CNS Injury Model for IL-b mRNA

This assay characterizes the regional expression of interleukin-1β (IL-1β) mRNA in specific brain regions following experimental lateral fluid-percussion traumatic brain injury (TBI) in rats. Results from these assays indicate that following TBI, the temporal expression of IL-1β mRNA is regionally stimulated in specific brain regions. These regional changes in cytokines, such as IL-1β play a role in the post-traumatic pathologic or regenerative sequelae of brain injury. A suitable assay may be found in WO 97/35856 whose disclosure is incorporated herein by reference.

Angiogenesis Assay:

Described in WO 97/32583, whose disclosure is incorporated herein by reference, is an assay for determination of inflammatory angiogenesis which may be used to show that cytokine inhibition will stop the tissue destruction of excessive or inappropriate proliferation of blood vessels.

Rhinovirus/Influenza Assay:

Cell lines, rhinovirus serotype 39, and influenza virus A/PR/8/34 were purchased from American Type Culture Collection (ATCC). BEAS-2B cells were cultured according to instructions provided by ATCC using BEGM (bronchial epithelial growth media) purchased from Clonetics Corp. HELA cell cultures, used for detection and titration of virus, were maintained in Eagle's minimum essential media containing 10% fetal calf serum, 2 mM 1-glutamine, and 10 mM HEPES buffer (MEM).

A modification of the method reported by Subauste et al., Supra, for in vitro infection of human bronchial epithelial cells with rhinovirus was used in these studies. BEAS-2B cells ($2\times10^5$/well) were cultured in collagen-coated wells for 24 hours prior to infection with rhinovirus. Rhinovirus serotype 39 was added to cell cultures for one hour incubation at 34° C. after which inoculum was replaced with fresh media and cultures were incubated for an additional 72 hours at 34° C. Supernatants collected at 72 hours post-infection were assayed for cytokine protein concentration by ELISA using commercially available kits (R&D Systems). Virus yield was also determined from culture supernatants using a microtitration assay in HELA cell cultures (Subauste et al., supra 1995). In cultures treated with p38 kinase inhibitors, drug was added 30 minutes prior to infection. Stocks of compounds were prepared in DMSO (10 mM drug) and stored at −20° C.

For detection of p38 kinase, cultures were incubated in basal media without growth factors and additives to reduce endogenous levels of activated p38 kinase. Cells were harvested at various time points after addition of rhinovirus. Detection of tyrosine phosphorylated p38 kinase by immunoblot was analyzed by a commercially available kit and was performed according to the manufacturer's instructions (PhosphoPlus p38 MAPK Antibody Kit: New England BioLabs Inc.).

In some experiments, BEAS-2B cells were infected with influenza virus a (strain A/PR/8/34) in place of rhinovirus. Culture supernatant was harvested 48 and 72 hour post-infection and tested by ELISA for cytokine as described above.

Cells and Virus: Influenza A/PR/8/34 sub type HIN1 (VR-95 American Type Culture Collection, Rockville, Md.) was grown in the allantoic cavity of 10 day old chicken eggs. Following incubation at 37° C., and refrigeration for 2½ hours at 4° C., allantoic fluid was harvested, pooled, and centrifuged (1,000 rcf; 15 min; 4° C.) to remove cells. Supematent was aliquoted and stored at −70° C. The titer of the stock culture of virus was $1.0 \times 10^{10}$ Tissue Culture Infective Dose/ml ($TCID_{50}$)

Inoculation procedure: Four-six week old female Balb/cAnNcrlBr mice were obtained from Charles River, Raleigh, N.C. Animals were infected intranasally. Mice were anesthetized by intraperitoneal injection of Ketamine (40 mg/kg; Fort Dodge Labs, Fort Dodge, Ia) and Xylazine (5 mg/kg; Miles, Shawnee Mission, Ks) and then inoculated with 100 TCID50 of PR8 diluted in PBS in 20 ul. Animals were observed daily for signs of infection. All animal studies were approved by SmithKline Beecham Pharmaceuticals Institutional Animal Care and Use Committee.

Virus titration: At various times post infection, animals were sacrificed and lungs were aseptically harvested. Tissues were homogenized, in vials containing 1 micron glass beads (Biospec Products, Bartlesville, Okla.) and 1 ml. of Eagles minimal essential medium. Cell debris was cleared by centrifugation at 1,000 rcf for 15 minutes at 4° C., and supernatants were serially diluted on Madin-Darby canine kidney (MDCK) cells. After 5 days of incubation at 37° C. (5% $CO_2$), 50 µl of 0.5% chick red blood cells were added per well, and agglutination was read after 1 hour at room temperature. The virus titer is expressed as 50% tissue culture infective dose ($TCID_{50}$) calculated by logistic regression.

ELISA: Cytokine levels were measured by quantitative ELISA using commercially available kits. Ear samples were homogenized using a tissue minser in PBS. Cell debris was cleared by centrifugation at 14,000 rpm for 5 minutes. The cytokine concentrations and thresholds were determined as described by the manufacturer; IL-6, IFN-γ, and KC (R&D Systems, Minneapolis, Minn.).

Myeloperoxidase Assay: Myeloperoxidase (MPO) activity was determined kinetically as described by Bradley et al. (1982). Briefly, rabbit cornea were homogenized in Hexadecyl Trimethyl-Ammonium Bromide (HTAB) (Sigma Chemical Co. St. Louis, Mo.) which was dissolved in 0.5 m Potassium phosphate buffer (J. T. Baker Scientific, Phillipsburg, N.J.). Following homogenization, the samples were subjected to freeze-thaw-sonication (Cole-Parmer 8853, Cole-Parmer, Vernon Hills, Il.) 3 times. Suspensions were then cleared by centrifugation at 12,500×g for 15 minutes at 4° C. MPO enzymatic activity was determined by colorimetric change in absorbance during a reaction of O-Dianisidine dihydrochloride (ODI) 0.175 mg/ml (Sigma Chemical Co. St. Louis, Mo.) with 0.0002% Hydrogen peroxide (Sigma Chemical Co. St. Louis, Mo.). Measurements were performed by using a Beckman Du 640 Spectrophotometer (Fullerton, Calif.) fitted with a temperature control device. 50 ul of material to be assayed was added to 950 ul of ODI and change in absorbance was measured at a wave length of 460 nm for 2 minutes at 25° C.

Whole Body Plethysomography: Influenza virus infected mice were placed into a whole body plethysomograph box with an internal volume of approximately 350-ml. A bias airflow of one l/min was applied to the box and flow changes were measured and recorded with a Buxco XA data acquisition and respiratory analysis system (Buxco Electronics, Sharon, Conn.). Animals were allowed to acclimate to the plethysmograph box for 2 min. before airflow data was recorded. Airway measurements were calculated as Penh (enhanced pause). Penh has previously been shown as an index of airway obstruction and correlates with increased intrapleural pressure. The algorithm for Penh calculation is as follows: Penh=[(expiratory time/relaxation time)−1]×(peak expiratory flow/peak inspiratory flow) where relaxation time is the amount of time required for 70% of the tidal volume to be expired.

Determination of arterial oxygen saturation. A Nonin veterinary hand held pulse oximeter 8500V with lingual sensor (Nonin Medical, Inc., Plymouth Minn.) was used to determine daily arterial oxygen saturation % SpO2 as described (Sidwell et al. 1992 Antimicrobial Agents and Chemotherapy 36:473-476).

Additional data and assay modifications may be found in PCT/US00/25386, (WO 01/19322) filed 15 Sep. 2000, whose disclosure is incorporated herein by reference in its entirety.

SYNTHETIC EXAMPLES

The compounds of this invention may be made by a variety of methods, including standard chemistry. Any previously defined variable will continue to have the previously defined meaning unless otherwise indicated. Illustrative general synthetic methods are set out below and then specific compounds of the invention are prepared in the working Examples.

An illustration of the preparation of the compounds of the present invention is shown in the Schemes below.

Scheme 1

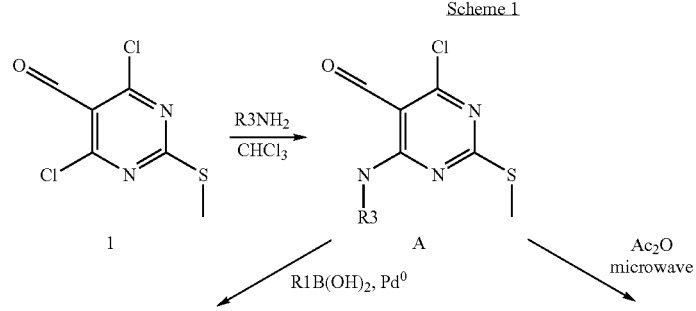

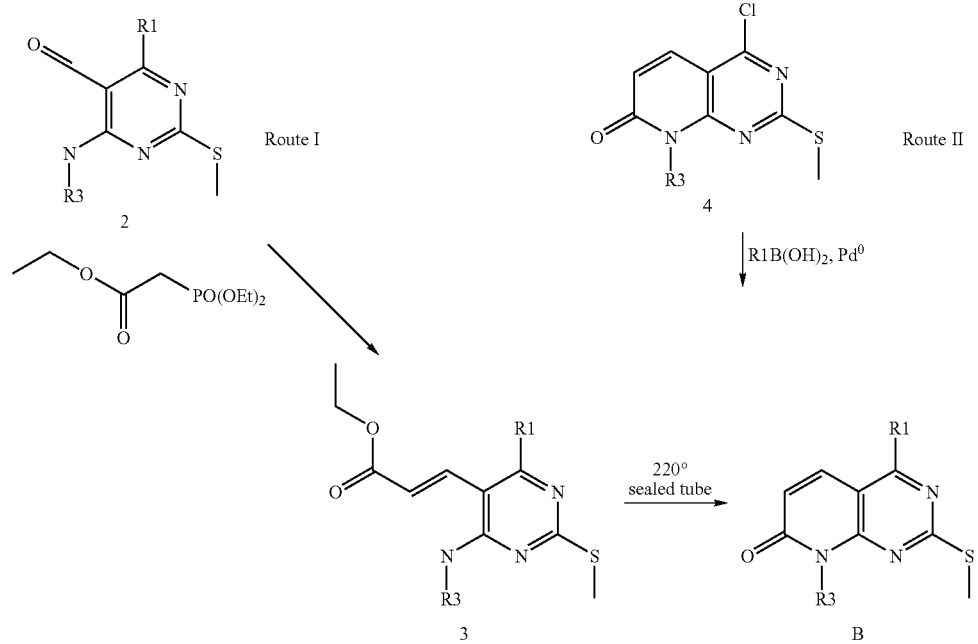

Scheme 1 illustrates synthesis of key intermediate Compound B from intermediate Compound A by two possible routes illustrated. Thus 4,6-dichloro-2-methylsulfanyl-pyrimidine-5-carbaldehyde, 1, (Santilli, et al *J. Heterocycl Chem*, 1971, 8, 445-453) can be displaced by a reaction not shown in Scheme 1 with a single equivalent of amine in the presence of NaH in DMSO (Santilli et al., *J. Heterocycl. Chem.* 1971 445-53) affording the desired compound Compound A along with imine. The imine side product may be converted to Compound A by treatment with aqueous HCl in THF. Direct conversion of Compound 1 to Compound A with no side products may be achieved as depicted in Scheme 1 using triethylamine and the desired amine in chloroform at room temperature for 10 minutes. The reaction was very effective for a range of alkyl amines (78-95% yield). For aryl amines, elevated temperatures (reflux) and longer reaction time (24 hours) may be necessary for reaction completion. Use of the base might be omitted when 3 or more equivalent of amine were used. Other suitable bases, include but are not limited to pyridine, diisopropyl ethylamine or pyrrolidine, which may also be used in an appropriate organic solvent, including but not limited to THF, diethyl ether or dioxane.

Intermediate Compound A can then be converted to Compound B via two routes as illustrated in Scheme 1. In Route I the monochloropyrimidine A may be first reacted with boronic acid or ester in the presence of a Pd⁰ catalyst (Suzuki reaction) to afford compound 2 in Scheme 1. These reactions may be otimized for any particular compound by variations in catalyst, solvent as well as temperature and the use of microwave or thermal conditions. Alternatively, the bi-aryl coupling reaction of Compound A may be performed using aryl or heteroaryl organozinc, organocopper, organotin, or other organometallic reagents known to afford bi-aryl cross-coupling products such as 2-Scheme I [see for example Solberg, J.; Undheim, K. *Acta Chemica Scandinavia* 1989, 62-68]. Displacement of the chlorine in A-Scheme I may also be achieved with nitrogen nucleophiles [for related aminations see U.S. Pat. Nos. 3,631,045 and 3,910,913], sulphur nucleophiles, [see Tumkevicius, S. *Liebigs Ann.* 1995, 1703-1705], oxygen nucleophiles, or alkyl nucleophiles.

Conversion to Compound B via Route 1 may proceed through intermediate 3 by a Horner-Emmons reaction (Wadsworth, *Org. Reactions*, 1977, 25, 73-253.) of triethyl phosphonoacetate with the aldehyde in Compound 2. Heating the resulting trans esters 3 in a sealed tube at 220° affords the key intermediates Compound B. Alternatively the intermediate Compound 2 can be converted in one step to Compound B by heating to solvent reflux a solution of Compound 2 in pyridine and acetic anhydride (WO02059083).

By Route 2, Compound A is cyclized in acetic anhydride with microwave heating to afford the 4-chloro-pyrido[2,3,d]pyrimidin-7(8H)one, 4. Conversion of Compound 4 to Compound B can proceed under the conditions described above for the conversion of Compound A to Compound 2.

Scheme 2

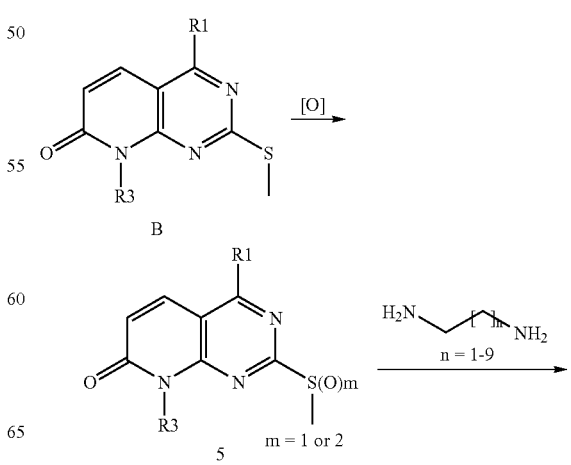

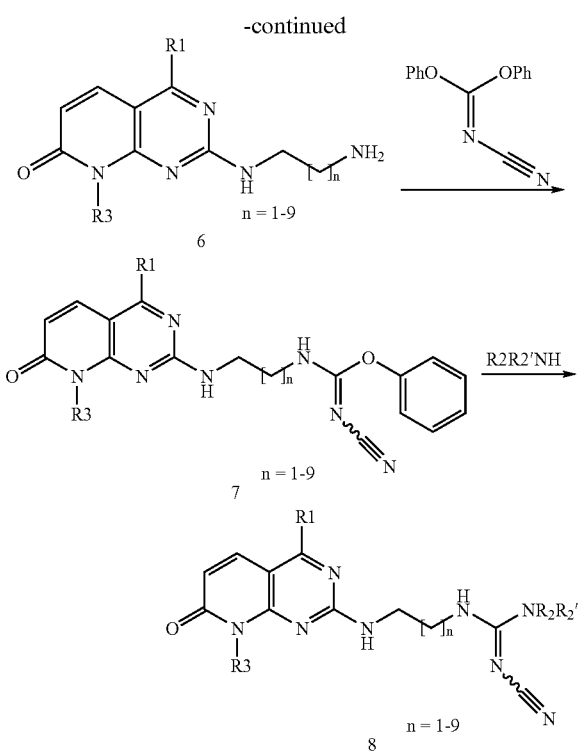

Key intermediate B is converted to the target cyanoguanidines by methods such as those depicted in Scheme 2. The sulfide in B is oxidized with a suitable oxidizing agent, such as oxone or meta-3-choloroperbezoic acid (commercially available from Sigma-Aldrich) or sodium periodate, H2O2 or other suitable oxidizing agent to afford the sulfones or sulfoxides 5 (For example March, J. *Advanced Organic Chemistry Reactions, Mechanisms and Structure*. Third Edition 1985, John Wiley & Sons, p 1089.) Either the sulfone or the sulfoxide are readily displaced by excess diamines to afford the usymmetrically substituted diamino analogs 6. Reaction of analogs 6 with diphenyl N-cyanocarbonimidate (Sigma-Aldrich) affords the intermediate 3-amino-3-phenyloxy-2-propenenitriles which could be detected via LCMS but were not isolated. In situ treatment with a second amine in a sealed vessel at varying temperatures and time depending on the amine afforded the unsymmetrically substituted cyanoguanidines 8. Microwave irradiation could improve yield and reduce reaction times for some of the final products. The order of addition of the amines to the diphenylcyanocarbonimidate may be altered depending on the desired products.

An alternative synthesis of the cyanoguanidines utilizes the method of Atwal and coworkers (Atwal, K S, et al *Tetrahedron Lett* 1989, 30, 7313-7316). By this method the amines 6 are converted to isothiocyanates which are in turn reacted with sodium cyanamide to form N-cyanothioureas. These intermediates are then reacted with R2R'2NH in the presence of EDC to afford the desired cyanoguanidines 8 as described by Atwal. The order of addition of the amines may be varied depending on the desired products.

Yet another embodiment of the invention is a synthetic approach that affords the cyanoguanidine(s) 8. This synthetis utilizes dimethyl N-cyanodithioimino-carbonate (Sigma-Aldrich) by essentially the same procedures as described herein to obtain the product(s) 8 with diphenyl N-cyanobonimidate.

SYNTHETIC EXAMPLES

The invention will now be described by reference to the following examples, which are merely illustrative and are not to be construed as a limitation of the scope of the present invention. All temperatures are given in degrees centigrade, all solvents are highest available purity and all reactions run under anhydrous conditions in an Ar atmosphere where necessary.

Mass spectra were run on an open access LC-MS system using electrospray ionization. LC conditions: 4.5% to 90% $CH_3CN$ (0.02% TFA) in 3.2 min with a 0.4 min hold and 1.4 min re-equilibration; detection by MS, UV at 214 nm, and a light scattering detector (ELS). Column: 1×40 mm Aquasil (C18) $^1$H-NMR (hereinafter "NMR") spectra were recorded at 400 MHz using a Bruker A M 400 spectrometer or a Bruker AVANCE 400. Multiplicities indicated are: s=singlet, d=doublet, t=triplet, q=quartet, m=multiplet and br indicates a broad signal. For preparative (prep) hplc; ca 50 mg of the final products were injected in 500 uL of DMSO onto a 50×20 mm I. D. YMC CombiPrep ODS-A column at 20 mL/min with a 10 min gradient from 10% $CH_3CN$ (0.1% TFA) to 90% $CH_3CN$ (0.1% TFA) in $H_2O$ (0.1% TFA) and a 2 min hold (unless otherwise stated). Flash chromatography was run over Merck Silica gel 60 (230-400 mesh) in solvent mixtures containing varying relative concentrations of dichloromethane and methanol, or EtOAc, and hexane, unless otherwise stated. Chromatotron chromatography as has been previously described (Desai, HK; Joshi, BS; Panu, AM; Pelletier, SW *J. Chromatogr.* 1985 223-227.) was run on chromatotron plates available from Analtech, Wilmington Del., USA.

| List of Abbreviations | |
|---|---|
| EDC: 1-(3-Dimethylaminopropyl)-3-ethylcarbodiimide hydrochloride | dppf: 1,1'-Bis(diphenylphosphino)-ferrocene |
| DMAP: 4-(Dimethylamino)pyridine | DMSO: Dimethylsulfoxide |
| m-CPBA: 3-Chlorobenzene-carboperoxoic acid | EtOAc: Ethyl acetate |
| THF: Tetrahydrofuran | DIPEA or DIEA: N,N-Diisopropylethylamine |
| DCM: Dichloromethane | SPE: Solid phase extraction |
| TFA: Trifluoroacetic anhydride | MDAP: Mass directed auto preparation |
| HATU: O-(7-Azabenzotriazol-1-yl)-N,N,N',N'-tetramethyluronium hexafluorophosphate | HBTU: O-Benzotriazol-1-yl-N,N,N',N'-tetramethyluronium hexafluorophosphate |
| NIS: N-Iodosuccinimide | HOBT: 1-Hydoxybenzotriazole hydrate |
| DMF: N,N-Dimethylformamide | HPLC: High Pressure Liquid Chromatography |
| IPA: isopropyl alcohol | M: molar |
| DSC: differential scanning calorimetry | mmol: millimoles |
| L: liters | mol: moles |
| mL: milliliters | aq: aqueous |
| mg: milligrams | eq: equivalents |
| g: grams | h: hours |
| rt: room temperature | mp: melting point |
| satd = saturated | min: minutes |
| dppf = 1,1'-bis(diphenylphosphino)ferrocene | NMP = 1-methyl-2-pyrrolidinone |

Other abbreviations are as described in the ACS Style Guide (American Chemical Society, Washington, DC, 1986).

Example 1

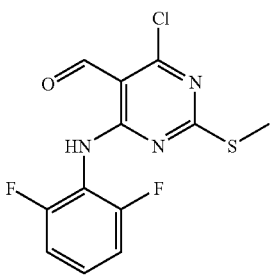

4-Chloro-6-[(2,6-difluorophenyl)amino]-2-(methylthio)-5-pirimidinecarbaldehyde

To a solution of 4,6-dichloro-2-methylsulfanyl-pyrimidine-5-carbaldehyde (11.1 grams(hereinafter "g"), 50 millimoles (hereinafter "mmol")) in CHCl₃ (100 milliliters (hereinafter "mL")) was added 2,6-difluoroaniline (8.07 mL, 75 mmol, 1.5 equivalents (hereinafter "eq")) followed by Et₃N (10.43 mL, 75 mmol, 1.5 eq). The reaction mixture turned yellow and was heated to reflux for 24 h, H₂O (50 mL) was added and the layers were separated. The organic layer was evaporated and the crude product was recrystallized from 200 mL of a methanol: H₂O mixture (2:1) to give 12.03 g (76%) of pure 4-chloro-6-(2,6-difluoro-phenylamino)-2-methylsulfanyl-pyrimidine-5-carbaldehyde. ¹H-NMR: δ 2.21 (s, 3H), 6.91 (m, 2H), 7.24 (m, 1H), 10.29 (s, 1H), 10.35 (br s, 1H). LC MS (m/e)=316 (MH+).

Example 2

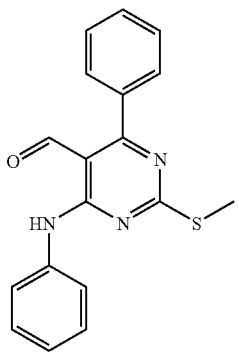

2-(Methylthio)-4-phenyl-6-(phenylamino)-5-pyrimidinecarbaldehyde

To a solution of 4-chloro-2-methylsulfanyl-6-phenylamino-pyrimidine-5-carbaldehyde (300 mg, 1.07 mmol) in dioxane (21 mL) and H₂O (7 mL) was added anhydrous K₂CO₃ (443 mg, 3.21 mmol, 3 eq) followed by phenylboronic acid (196 mg, 1.6 mmol, 1.5 eq). The reaction mixture was degassed and tetrakis(triphenylphosphine)-palladium (61 mg, 0.053 mmol, 0.05 eq) was added. The reaction mixture was then heated under reflux for 24 h and cooled 23°, the layers were separated, EtOAc (50 mL), followed by H₂O (10 mL), was added, the organic layer was separated, washed with sat'd aqueous (hereinafter "aq") NaCl, dried (MgSO₄) and filtered. The yellow solution was then evaporated. Product was purified by column chromatography or by crystallization from 10 mL of isopropanol: H₂O (2:1) to give 240 mg (70% yield) of pure 2-methylsulfanyl-4-phenyl-6-phenylamino-pyrimidine-5-carbaldehyde. ¹H-NMR δ 2.60 (s, 3H), 7.22 (m, 1H), 7.35-7.81 (m, 9H), 9.89 (s, 1H), 11.31 (br s, 1H), LC MS (m/e)=322 (MH+).

Example 3

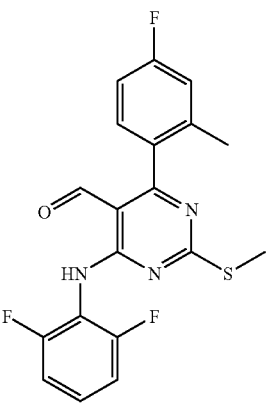

4-[(2,6-Difluorophenyl)amino]-6-(4-fluoro-2-methylphenyl)-2-(methylthio)-5-pyrimidinecarbaldehyde Prepared as described above in Example 2 starting from 4-chloro-6-(2,6-difluoro-phenylamino)-2-methylsulfanyl-pyrimidine-5-carbaldehyde and 4-fluoro-2-methyl-phenyl-boronic acid to give the title compound 4-(2,6-difluoro-phenylamino)-6-(4-fluoro-2-methyl-phenyl)-2-methylsulfanyl-pyrimidine-5-carbaldehyde. ¹H-NMR: δ 2.21 (s, 3H), 2.25 (s, 3H), 6.95 (m, 4H), 7.18 (m, 4H), 9.54 (s, 1H), 10.29 (br s, 1H). LC MS (m/e)=390 (MH+).

Example 4

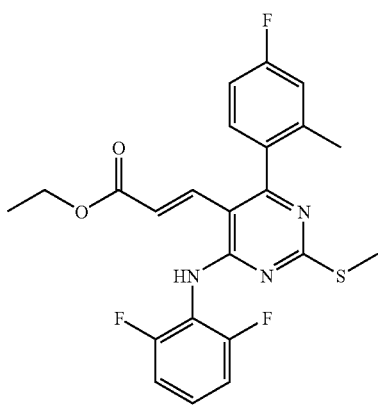

Ethyl (2E)-3-[4-[(2,6-difluorophenyl)amino]-6-(4-fluoro-2-methylphenyl)-2-(methylthio)-5-pyrimidinyl]-2-propenoate To a solution of triethyl phosphonoacetate (8.18 mL, 41.3 mmol, 2 eq) in 120 mL of anhyd THF was added NaH (2.05 g, 60% dispersion in mineral oil, 51.4 mmol, 2.5 eq) and the reaction mixture was stirred for 30 min at 23°. To this solution was added 4-(2,6-difluoro-phenylamino)-6-(4-fluoro-2-methyl-phenyl)-2-methylsulfanyl-pyrimidine-5-carbaldehyde (8 g, 20.65 mmol) as a solution in 10 mL of anhyd. THF and the reaction mixture was heated under reflux for 3 h while being monitored by HPLC. After completion, 20 mL of sat'd. aq. NH$_4$Cl was added and the layers were separated. The aq. layer was washed with Et$_2$O (100 mL) and the organic layers were combined. The organic layer was washed with H$_2$O, and sat'd aq. NaCl, dried (MgSO$_4$), filtered and solvent was evaporated. The crude product was recrystallized from 100 mL of methanol: H$_2$O (1:1) to afford 8.1 g (88%) of pure (E)-3-[4-(2,6-difluoro-phenylamino)-6-(4-fluoro-2-methyl-phenyl)-2-methylsulfanyl-pyrimidin-5-yl]-acrylic acid ethyl ester. LC MS (m/e)=460 (MH+). Rt=2.49 min Example 5

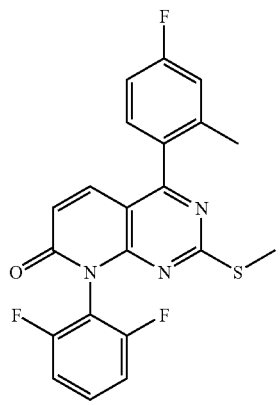

8-(2,6-Difluorophenyl)-4-(4-fluoro-2-methylphenyl)-2-(methylthio)pyrido[2,3-d]pyrimidin-7(8H)-one The product of example 4 [(E)-3-[4-(2,6-difluoro-phenylamino)-6-(4-fluoro-2-methyl-phenyl)-2-methylsulfanyl-pyrimidin-5-yl]-acrylic acid ethyl ester] (8.1 g, 17.6 mmol) was dissolved in 50 mL of anhydrous toluene. Reaction mixture was heated in a sealed tube at 220° C. for 48 h, toluene was evaporated and the yellow residue purified by Flash chromatography to give 7.1 g (96%) of 8-(2,6-difluoro-phenyl)-4-(4-fluoro-2-methyl-phenyl)-2-methylsulfanyl-8H-pyrido[2,3-d]pyrimidin-7-one. $^1$H-NMR (CDCl$_3$) δ 2.24 (s, 3H), 2.29 (s, 3H), 6.63 (d, 1H, J=9.6 Hz), 7.03-7.20 (m, 4H), 7.25 (m, 1H), 7.51 (m, 2H); LC MS (m/e)=414 (MH+).

Example 6

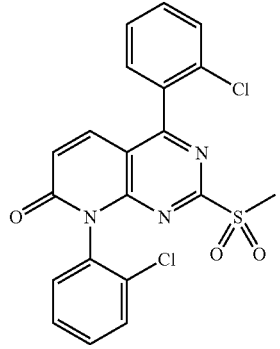

4,8-Bis(2-chlorophenyl)-2-(methylsulfonyl)pyrido[2,3-d]primidin-7(8H)-one

To a solution of 4,8-bis-(2-chloro-phenyl)-2-methylsulfanyl-8H-pyrido[2,3-d]pyrimidin-7-one (414 mg, 1 mmol) in CHCl$_3$ (15 mL) was added 3-chloro-peroxybenzoic acid (549 mg, 3 mmol, 3 eq) and the reaction mixture was stirred 5 h at 23°, then 1 M aq Na$_2$CO$_3$ (10 mL) was added, the layers were separated, and the organic layer was washed with H$_2$O, dried (MgSO$_4$) and the solvent was evaporated to afford 4,8-bis-(2-chloro-phenyl)-2-methanesulfonyl-8H-pyrido[2,3-d]pyrimidin-7-one (550 mg, 89% yield). $^1$H-NMR (CDCl$_3$) δ 3.15 (s, 3H), 6.96 (d, 1H, J=9.8 Hz), 7.26 (m, 2H), 7.51-7.80 (m, 9H). LC MS (m/e)=446 (MH+).

Example 7

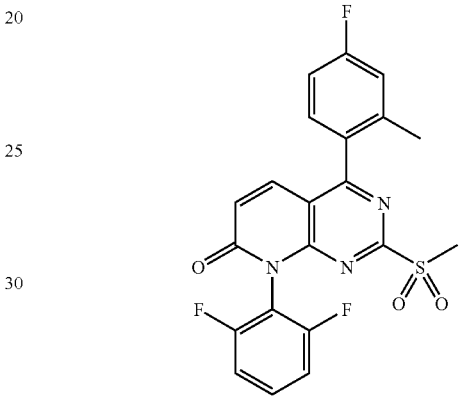

8-(2,6-Difluorophenyl)-4-(4-fluoro-2-methylphenyl)-2-(methylsulfonyl)pyrido[2,3-d]pyrimidin-7(8H)-one Prepared as described above in Example 6 starting from 8-(2,6-difluoro-phenyl)-4-(4-fluoro-2-methyl-phenyl)-2-methylsulfanyl-8H-pyrido[2,3-d]pyrimidin-7-one to give the title compound 8-(2,6-difluoro-phenyl)-4-(4-fluoro-2-methyl-phenyl)-2-methane-sulfonyl-8H-pyrido[2,3-d]pyrimidin-7-one. LC MS (m/e)=446 (MH+). Rt=2.13 min.

Example 8

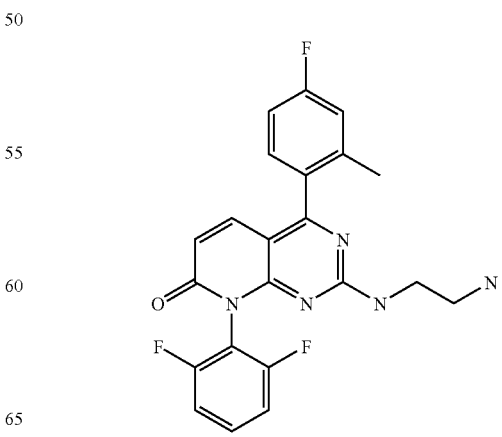

2-[(2-Aminoethyl)amino]-8-(2,6-difluorophenyl)-4-(4-fluoro-2-methylphenyl)pyrido[2,3-d]pyrimidin-7(8H)-one The title compound of Example 7 [8-(2,6-difluorophenyl)-4-(4-fluoro-2-methylphenyl)-2-methanesulfonyl-8H-pyrido[2,3-d]pyrimidin-7-one] (0.89 g, 0.002 mol) in dry THF, stirring at 23°, under Ar, was treated with ethylenediamine (668 uL, 0.01 mol). The color became bright orange. LC MS showed no starting material after 5 min. Reaction was stripped to dryness; the residue taken up in ethyl acetate-water. The layers were separated and the aqueous phase adjusted to pH 10.5 with 10% NaOH. Aqueous phase was extracted twice with ethyl acetate; combined organic layers were dried ($Na_2SO_4$), then evaporated to give 0.762 g (89%) of the title compound as an amber glass. LC MS (m/e)=426 (MH+). Rt=1.52 min.

Example 9

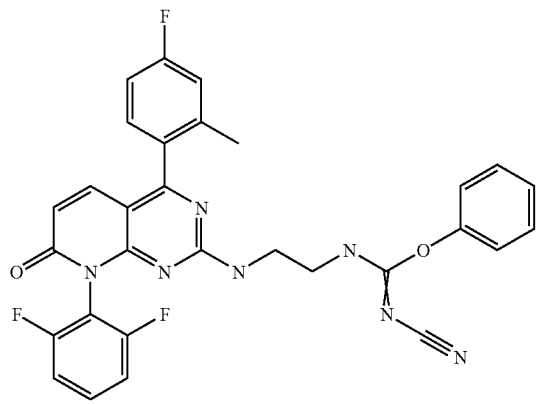

Phenyl N-cyano-N'-(2-{[8-(2,6-difluorophenyl)-4-(4-fluoro-2-methylphenyl)-7-oxo-7,8-dihydropyrido[2,3-d]pyrimidin-2-yl]amino}ethyl)imidocarbamate The title compound from Example 8 [8-(2,6-Difluorophenyl)-4-(4-fluoro-2-methylphenyl)-2-[(2-aminoethyl)amino]-8H-pyrido[2,3-d]pyrimidin-7-one](0.382 g, 0.0009 mol) was treated with stirring with diphenylcyanocarbonimidate (0.214 g, 0.0009 mol) in isopropanol (5 mL). Stirred at 23° for 0.5 hours. LC/MS showed a new major peak corresponding to the desired product and no starting material in the solution. LC MS (m/e)=570(MH+). Rt=2.24 min.

Example 10

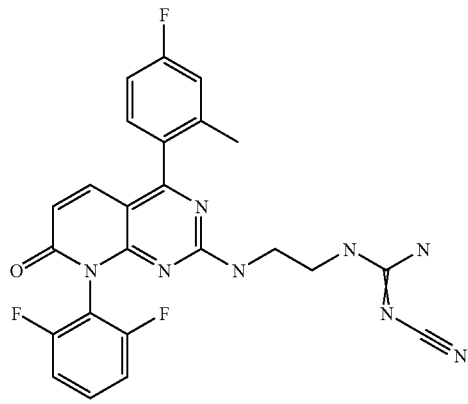

8-(2,6-Difluorophenyl)-4-(4-fluoro-2-methylphenyl)-2-(2-[N'-cyanopuanadino]-aminoethyl)amino]-8H-pyrido[2,3-d]pyrimidin-7-one, or alternatively N-cyano-N'-(2-{[8-(2,6-difluorophenyl)-4-(4-fluoro-2-methylphenyl)-7-oxo-7,8-dihydropyrido [2,3-d]pyrimidin-2-yl]amino}ethyl)guanidine The title compound from Example 9 [8-(2,6-Difluorophenyl)-4-(4-fluoro-2-methylphenyl)-2-N-[(2-[1-phenoxy-2-cyano-2-azaethylene]aminoethyl)amino]-8H-pyrido[2,3-d]pyrimidin-7-one] (0.0009 mol) in isopropanol (5 mL) was saturated with $NH_3$ (g), then stirred overnight at 23° in a sealed tube. The solution stripped to a reddish residue. This was purified on a Chromatotron™ rotor plate (silica gel) methylene chloride-methanol (94:6); eluted product fractions combined and stripped to dryness; taken up in ether containing a small amount of methanol which, upon sonication, yielded a pink microcrystalline solid which upon drying afforded 195 mg (44%) title compound. [m.p. 204°-206°] LC MS (m/e)=493(MH+). Rt=1.79 min.

Example 11

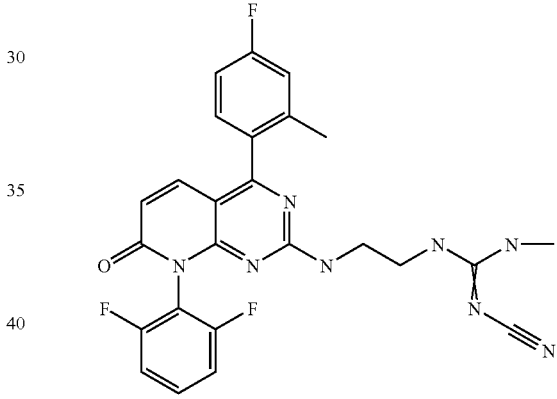

8-(2,6-Difluorophenyl)-4-(4-fluoro-2-methylphenyl)-2-(2-[N'-cyano-N''-methylguanadinol-aminoethyl)amino]-8H-pyrido[2,3-d]pyrimidin-7-one, or alternatively N-cyano-N'-(2-{[8-(2,6-difluorophenyl)-4-(4-fluoro-2-methylphenyl-7-oxo-7,8-dihydropyrido[2,3-d]pyrimidin-2-yl]amino}ethyl)-N''-methylguanidine The title compound from Example 9 [8-(2,6-Difluorophenyl)-4-(4-fluoro-2-methylphenyl)-2-N-[(2-[1-phenoxy-2-cyano-2-azaethylene]aminoethyl)amino]-8H-pyrido[2,3-d]pyrimidin-7-one] (0.00064 mol) in isopropanol (4 mL) was treated with 1M methylamine in THF (1.5 mL), then stirred overnight 23° in a sealed tube. The solution stripped to a residue. This was purified on a Chromatotron™ rotor plate (silica gel) methylene chloride-methanol (94:6); eluted product fractions combined and stripped to dryness to afford 135.3 mg (44%) desired product. LC MS (m/e)=507(MH+). Rt=1.90 min.

Example 12

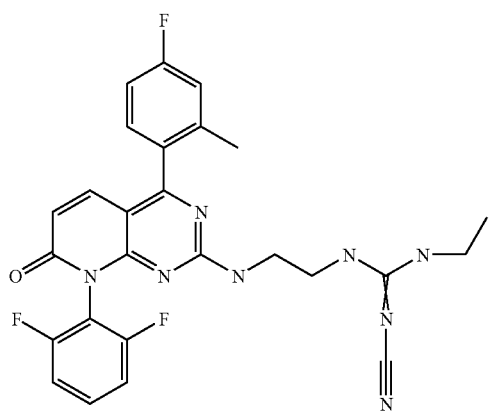

8-(2,6-Difluorophenyl)-4-(4-fluoro-2-methylphenyl)-2-(2-[N'-cyano-N''-ethylguanadino]-aminoethyl)amino]-8H-pyrido[2,3-d]pyrimidin-7-one, or alternatively, N-cyano-N'-(2-{[8-(2,6-difluorophenyl)-4-(4-fluoro-2-methylphenyl)-7-oxo-7,8-dihydropyrido[2,3-d]pyrimidin-2-yl]amino}ethyl)-N''-ethylizuanidine The title compound from Example 9 [8-(2,6-Difluorophenyl)-4-(4-fluoro-2-methylphenyl)-2-N-[(2-[1-phenoxy-2-cyano-2-azaethylene]aminoethyl)amino]-8H-pyrido[2,3-d]pyrimidin-7-one] (0.00064 mol) in isopropanol (4 mL) was treated with 1M ethylamine in THF (1.5 mL), then stirred overnight at 23° in a sealed tube. The reaction was only 50% complete by LC/MS; therefore, the reaction was warmed to 60° for 3 hrs which drove the reaction to completion. The solution stripped to a residue. This was purified on a Chromatotron™ rotor plate (silica gel) methylene chloride-methanol (94:6); eluted product fractions combined and stripped to dryness to afford 107 mg (34%) desired product. LC MS (m/e)=521.2(MH+). Rt=2.13 min.

Example 13

N-Cyano-N'-(2-{[4-(2,4-difluorophenyl)-8-(2-fluorophenyl)-7-oxo-7,8-dihydropyrido[2,3-d]pyrimidin-2-yl]amino}ethyl)guanidine a) 4-(2,4-difluorophenyl)-8-(2-fluorophenyl)-2-(methylsulfonyl)pyrido[2,3-d]pyrimidin-7(8H)-one

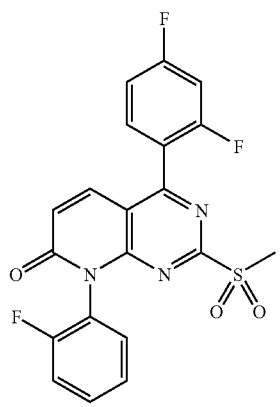

The title compound was prepared by following the procedures of steps a, b, c and d in Example 1 of WO 03/088972, whose disclosure is incorporated herein by reference, except that 2-fluoroaniline was used for the displacement in step a. See also the description in WO 02/059083 whose disclosure is incorporated herein by reference herein.

b) 2-[(2-Aminoethyl)amino]-4-(2,4-difluorophenyl)-8-(2-fluorophenyl)pyrido[2,3-d]pyrimidin-7(8H)-one

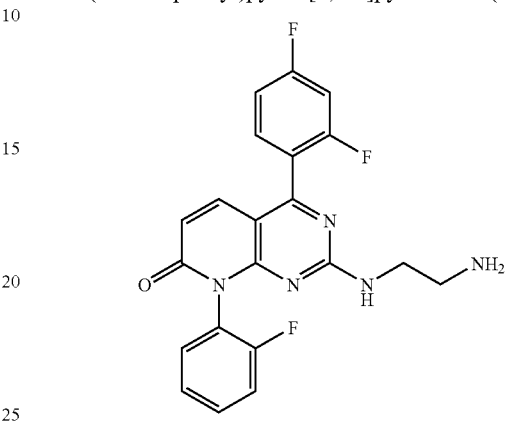

To a solution of 4-(2,4-difluorophenyl)-8-(2-fluorophenyl)-2-(methylsulfonyl)-pyrido[2,3-d]pyrimidin-7(8H)-one (30 mg, 0.070 mmol) in dry THF (1 mL) was added ethylenediamine (23 uL, 0.35 mmol). The white precipitate initially formed redissolved on stirring. The mixture was stirred for about 15 min at about 20° C. LC/MS showed no starting material. The solvent was evaporated and the residue redissolved in DCM (1 mL) and water (1 mL). The layers were separated and the aqueous phase was basified with 2M sodium hydroxide (1 mL). The aqueous phase was extracted with DCM (2×1 mL) and the combined organic layers were evaporated to give 28 mg (100%) of the title compound. LC-MS m/z 412 (M+H)+, 2.19 min (ret time).

c) Phenyl N-cyano-N'-(2-{[4-(2,4-difluorophenyl)-8-(2-fluorophenyl)-7-oxo-7,8-dihydropyrido[2,3-d]pyrimidin-2-yl]amino}ethyl)imidocarbamate

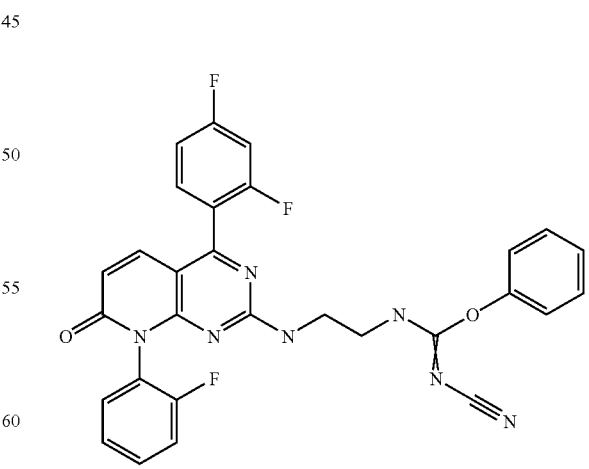

To a solution of 2-[(2-aminoethyl)amino]-4-(2,4-difluorophenyl)-8-(2-fluorophenyl)pyrido[2,3-d]pyrimidin-7(8H)-one (28 mg, 0.070 mmol) in isopropanol (2 mL) was added diphenyl cyanocarbonimidate (17 mg, 0.070 mmol).

The mixture was stirred for about 30 min at about 20° C. LC/MS showed a new peak corresponding to the desired product and no starting material in the solution. LC-MS m/z 556 (M+H)⁺, 3.24 min (ret time).

d) N-Cyano-N'-(2-{[4-(2,4-difluorophenyl)-8-(2-fluorophenyl)-7-oxo-7,8-dihydropyrido[2,3-d]pyrimidin-2-yl]amino}ethyl)guanidine

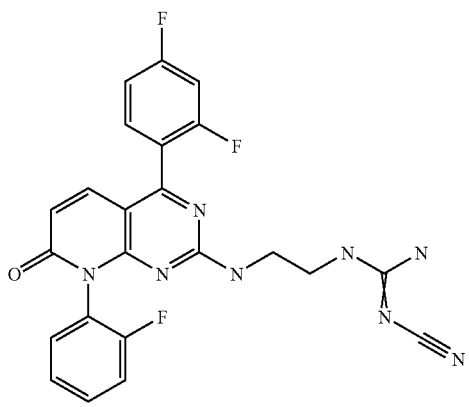

To a solution of phenyl N-cyano-N'-(2-{[4-(2,4-difluorophenyl)-8-(2-fluorophenyl)-7-oxo-7,8-dihydropyrido[2,3-d]pyrimidin-2-yl]amino}-ethyl)imidocarbamate in isopropanol (2 mL) was added a 2M solution of ammonia in isopropanol (2 mL). The mixture was irradiated with microwave at about 60° C. for about 20 min. LC/MS showed a mixture containing approximately 25% product and 75% starting material. The mixture was kept in a sealed tube for 6 days. LC/MS showed 100% product. The solvent was evaporated and the residue was purified to give the title compound (20 mg, 60%). LC-MS m/z 479 (M+H)⁺, 2.84 min (ret time).

Example 14

N-Cyano-N'-(2-{[8-(2,6-difluorophenyl)-4-(2-methylphenyl)-7-oxo-7,8-dihydropyrido[2,3-d]pyrimidin-2-yl]amino}ethyl)guanidine a) 4-Chloro-8-(2,6-difluorophenyl)-2-(methylthio)pyrido[2,3-d]pyrimidin-7(8H)-one

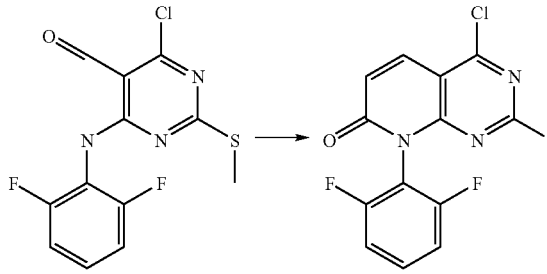

A solution of 4-chloro-6-[(2,6-difluorophenyl)amino]-2-(methylthio)-5-pyrimidinecarbaldehyde (200 mg, 0.63 mmol) in DMF (4.0 mL) and acetic anhydride (2.0 mL) was heated with a microwave reactor (160° C.) for 30 minutes. The resultant mixture was then concentrated. Flash chromatography (EtOAc/Hexane, 1:5) provided the title compound (109 mg, 50%): LC-MS m/z 340 (M+H)⁺; ¹H-NMR(CDCl₃) 2.24 (s, 3H), 6.80 (d, J=9.8 Hz, 1H), 7.12 (m, 2H), 7.49 (m, 1H), 8.04 (d, J=9.8 Hz, 1H).

b) 8-(2,6-Difluorophenyl)-4-(2-methylphenyl)-2-(methylthio)pyrido[2,3-d]pyrimidin-7(8H)-one

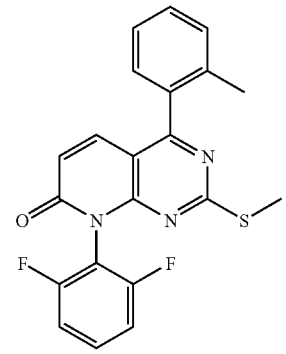

THF (10 mL) and 2M sodium carbonate (2 mL) were added to a mixture of 4-chloro-8-(2,6-difluorophenyl)-2-(methylthio)pyrido[2,3-d]pyrimidin-7(8H)-one (0.34 g, 1.0 mmol, solid-supported tetrakis(triphenylphosphine)palladium(0) (0.39 g, 0.1 mmol) and 4-fluorobenzeneboronic acid (0.21 g, 1.5 mmol). The mixture was irradiated with microwave at about 150° C. for about 20 min, then filtered and the filtrate evaporated. The crude product was redissolved in ethyl acetate (10 mL) and water (10 mL). The layers were separated and the organic layer was dried over magnesium sulphate, filtered and evaporated. The crude product was purified by flash chromatography on silica gel with cyclohexane containing ethyl acetate (0 to 50%) to give the title compound (0.25 g, 63%). LC-MS m/z 396 (M+H)⁺, 3.55 min (ret time).

c) 8-(2,6-Difluorophenyl)-4-(2-methylphenyl)-2-(methylsulfonyl)pyrido[2,3-d]pyrimidin-7(8H)-one

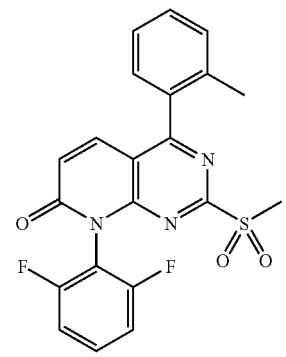

To a solution of 8-(2,6-difluorophenyl)-4-(2-methylphenyl)-2-(methylthio)pyrido-[2,3-d]pyrimidin-7(8H)-one (0.25 g, 0.65 mmol) in dry DCM (20 mL) was added 3-chloroperoxybenzoic acid (0.33 g, 1.95 mmol) and the mixture was stirred for about 16 hours at 20° C. 1M sodium carbonate (10 mL) was added and the layers were separated. The organic layer was evaporated to give the title product (0.28 g, 100%). LC-MS m/z 428 (M+H)⁺, 3.14 min (ret time).

d) 2-[(2-Aminoethyl)amino]-8-(2,6-difluorophenyl)-4-(2-methylphenyl)pyrido[2,3-d]pyrimidin-7(8H)-one

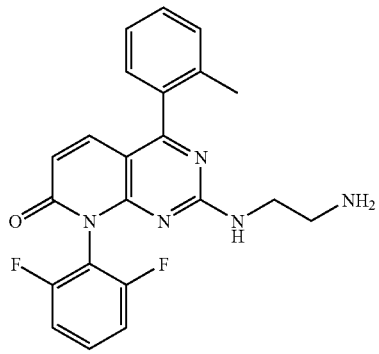

The title compound was prepared from 8-(2,6-difluorophenyl)-4-(2-methylphenyl)-2-(methylsulfonyl)pyrido[2,3-d]pyrimidin-7(8H)-one by following the procedures in Example 13b. LC-MS m/z 408 (M+H)⁺, 2.30 min (ret time).

e) N-Cyano-N'-(2-{[8-(2,6-difluorophenyl)-4-(2-methylphenyl)-7-oxo-7,8-dihydropyrido[2,3-d]pyrimidin-2-yl]amino}ethyl) guanidine

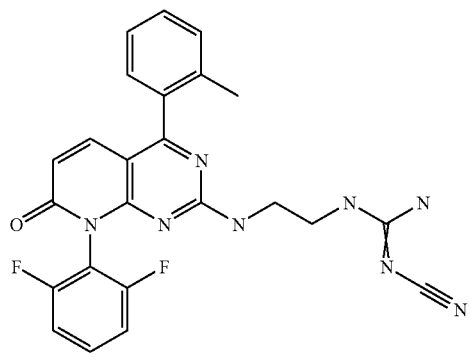

To a solution of 2-[(2-aminoethyl)amino]-8-(2,6-difluorophenyl)-4-(2-methylphenyl)pyrido[2,3-d]pyrimidin-7(8H)-one (20 mg, 0.050 mmol) in isopropanol (2 mL) was added diphenyl cyanocarbonimidate (12 mg, 0.050 mmol) and the mixture stirred for about 1 hour at about 20° C. A 2M solution of ammonia in isopropanol (2 ml) was added and the mixture stirred at about 20° C. for about 3 days. The solvent was evaporated and the residue redissolved in 2M ammonia in isopropanol (2 mL). The mixture was irradiated with microwave at about 60° C. for about 40 min. The mixture was stored in a sealed tube for 7 days. The solvent was evaporated and the crude product was purified to give the title compound (14 mg, 59%). LC-MS m/z 475 (M+H)⁺, 2.93 min (ret time).

Example 15

N-Cyano-N'-(2-{[8-(2,6-difluorophenyl)-4-(4-fluorophenyl)-7-oxo-7,8-dihydropyrido[2,3-d]pyrimidin-2-yl]amino}ethyl)guanidine a) 8-(2,6-Difluorophenyl)-4-(4-fluoroohenyl)-2-(methylsulfonyl)pyrido[2,3-d]pyrimidin-7(8H)-one

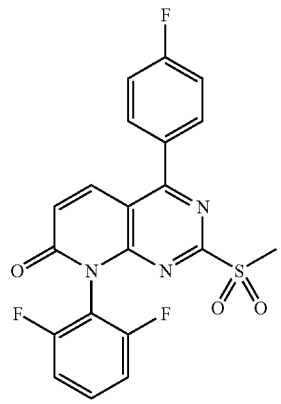

The title compound was prepared by following the procedures in Examples 14b and 14c except 4-fluorobenzeneboronic acid was used for the Suzuki cross coupling reaction. LC-MS m/z 432 (M+H)⁺, 3.10 min (ret time).

b) 2-[(2-Aminoethyl)amino]-8-(2,6-difluorophenyl)-4-(4-fluorophenyl)pyrido[2,3-d]pyrimidin-7(8H)-one

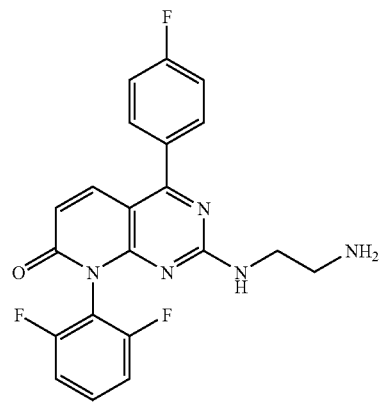

The title compound was prepared from 8-(2,6-difluorophenyl)-4-(4-fluorophenyl)-2-(methylsulfonyl)pyrido[2,3-d]pyrimidin-7(8H)-one by following the procedures in Example 13b. LC-MS m/z 412 (M+H)⁺, 2.30 min (ret time).

c) N-Cyano-N'-(2-{[8-(2,6-difluorophenyl)-4-(4-fluorophenyl)-7-oxo-7,8-dihydropyrido[2,3-d]pyrimidin-2-yl]amino}ethyl) guanidine

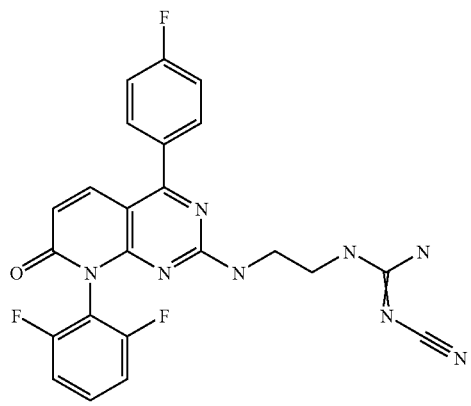

The title compound was prepared from 2-[(2-aminoethyl)amino]-8-(2,6-difluorophenyl)-4-(4-fluorophenyl)pyrido[2,3-d]pyrimidin-7(8H)-one by following the procedures in Example 14e. LC-MS m/z 479 (M+H)+, 2.94 min (ret time).

Example 16

N-cyano-N'-(2-{[4-(2,4-difluorophenyl)-8-(2,6-difluorophenyl)-7-oxo-7,8-dihydropyrido[2,3-d]pyrimidin-2-yl]amino}ethyl)guanidine a) 4-(2,4-Difluorophenyl)-8-(2,6-difluorophenyl)-2-(methylsulfonyl)pyrido[2,3 d]pyrimidin-7(8H)-one

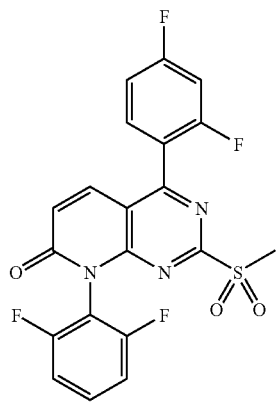

The title compound was prepared by following the procedures in Examples 14b and 14c except 2,4-difluorobenzeneboronic acid was used for the Suzuki cross coupling reaction. LC-MS m/z 450 (M+H)+, 3.11 min (ret time).

b) 2-[(2-Aminoethyl)amino]-4-(2,4-difluorophenyl)-8-(2,6-difluorophenyl)pyrido[2,3-d]pyrimidin-7(8H)-one

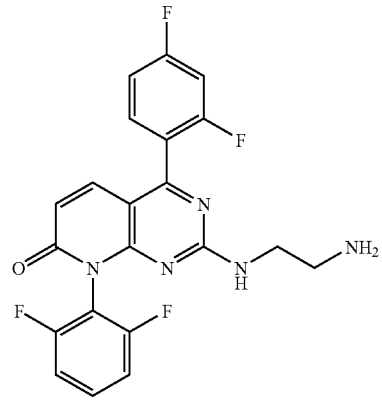

The title compound was prepared from 4-(2,4-Difluorophenyl)-8-(2,6-difluorophenyl)-2-(methylsulfonyl)pyrido[2,3-d]pyrimidin-7(8H)-one by following the procedures in Example 13b. LC-MS m/z 430 (M+H)+, 2.31 min (ret time).

c) N-Cyano-N'-(2-{[4-(2,4-difluorophenyl)-8-(2,6-difluorophenyl)-7-oxo-7,8-dihydropyrido[2,3-d]pyrimidin-2-yl]amino}ethyl)guanidine

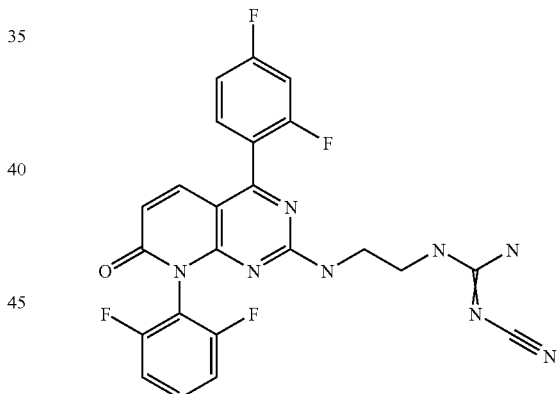

The title compound was prepared from 2-[(2-aminoethyl)amino]-4-(2,4-difluorophenyl)-8-(2,6-difluorophenyl)pyrido[2,3-d]pyrimidin-7(8H)-one by following the procedures in Example 14e. LC-MS m/z 497 (M+H)+, 2.93 min (ret time).

All publications, including but not limited to patents and patent applications, cited in this specification are herein incorporated by reference as if each individual publication were specifically and individually indicated to be incorporated by reference herein as though fully set forth.

The above description fully discloses the invention including preferred embodiments thereof. Modifications and improvements of the embodiments specifically disclosed herein are within the scope of the following claims. Without further elaboration, it is believed that one skilled in the art can, using the preceding description, utilize the present invention to its fullest extent. Therefore, the Examples herein are to be construed as merely illustrative and not a limitation of the scope of the present invention in any way. The embodiments of the invention in which an exclusive property or privilege is claimed are defined as follows.

What is claimed is:

1. A compound of the formula:

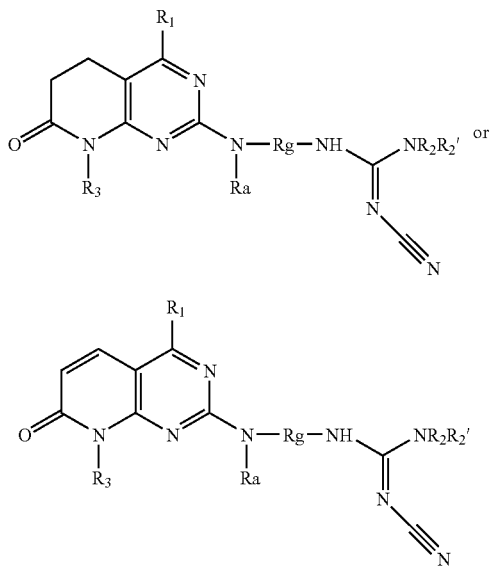

wherein $R_1$ is an optionally substituted aryl or an optionally substituted heteroaryl ring;

$R_2$ and $R_{2'}$ are independently selected from hydrogen, $C_{1-10}$ alkyl, $C_{3-7}$cycloalkyl, $C_{3-7}$cycloalkyl$C_{1-10}$alkyl, $C_{5-7}$ cycloalkenyl, $C_{5-7}$ cycloalkenyl-$C_{1-10}$alkyl, aryl, aryl$C_{1-10}$ alkyl, heteroaryl, heteroaryl$C_{1-10}$ alkyl, heterocyclic, or a heterocyclyl$C_{1-10}$ alkyl moiety, wherein all of the moieties are optionally substituted, or $R_2$ and $R_{2'}$ together with the nitrogen to which they are attached form a 5 to 7 membered optionally substituted ring, which ring may contain an additional heteroatom selected from O/N/S;

$R_a$ is hydrogen, or an optionally substituted $C_{1-4}$ alkyl;

$R_g$ is selected from an optionally substituted —$C_{1-10}$ alkyl-, —$CH_2$—$CH_2$—O—$CH_2$—$CH_2$—, —$CH_2$—C(O)—$CH_2$, $CH_2$—C(O)N($R_{12}$)$CH_2$—$CH_2$—, $CH_2$—N($R_{12}$)C(O)$CH_2$—, $CH_2$—CH(O$R_{12}$)—$CH_2$, $CH_2$—C(O)O—$CH_2$—$CH_2$, or $CH_2$—$CH_2$—O—C(O)$CH_2$—;

$R_{12}$ is hydrogen, or an optionally substituted $C_{1-4}$ alkyl;

$R_3$ is a $C_{1-10}$ alkyl, $C_{3-7}$ cycloalkyl, $C_{3-7}$ cycloalkyl$C_{1-4}$ alkyl, aryl, aryl$C_{1-10}$ alkyl, heteroaryl, heteroaryl$C_{1-10}$ alkyl, heterocyclic, or a heterocyclyl$C_{1-10}$ alkyl moiety, which moieties are all optionally substituted; or a pharmaceutically acceptable salt thereof.

2. The compound according to claim 1 which is Formula (I), or a pharmaceutically acceptable salt thereof.

3. The compound according to claim 1 which is Formula (Ia), or a pharmaceutically acceptable salt thereof.

4. The compound according to claim 1 wherein $R_1$ is optionally substituted one or more times independently at each occurrence by substituents selected from halogen, $C_{1-4}$ alkyl, halo-substituted-$C_{1-4}$ alkyl, hydroxy, cyano, nitro, $(CR_{10}R_{20})_v NR_4R_{14}$, $(CR_{10}R_{20})_v C(Z)NR_4R_{14}$, $(CR_{10}R_{20})_v C(Z)OR_8$, $(CR_{10}R_{20})_v COR_c$, $(CR_{10}R_{20})_v C(O)H$, $SR_5$, $S(O)R_5$, $S(O)_2R_5$, $(CR_{10}R_{20})_v OR_8$, $ZC(Z)R_{11}$, $N(R_{10'})C(Z)R_{11}$, or $N(R_{10'})S(O)_2R_7$; and wherein $R_4$ and $R_{14}$ are each independently selected at each occurrence, from hydrogen, optionally substituted $C_{1-4}$ alkyl, optionally substituted $C_{3-7}$ cycloalkyl, $C_{3-7}$ cycloalkyl$C_{1-4}$alkyl, optionally substituted aryl, or optionally substituted aryl-$C_{1-4}$ alkyl, heteroaryl, heteroaryl $C_{1-4}$ alkyl, heterocyclic, or heterocyclic $C_{1-4}$ alkyl; or $R_4$ and $R_{14}$ together with the nitrogen which they are attached form an optionally substituted heterocyclic ring of 4 to 7 members, which ring optionally contains an additional heteroatom selected from oxygen, sulfur or $NR_9$;

$R_5$ is independently selected, at each occurrence by hydrogen, $C_{1-4}$ alkyl, $C_{2-4}$ alkenyl, $C_{2-4}$ alkynyl or $NR_4R_{14}$, excluding the moieties $SR_5$ being $SNR_4R_{14}$, $S(O)_2R_5$ being $SO_2H$ and $S(O)R_5$ being SOH;

$R_7$ is independently selected from $C_{1-6}$alkyl, aryl, aryl$C_{1-6}$ alkyl, heterocyclic, heterocyclyl$C_{1-6}$ alkyl, heteroaryl, or heteroaryl$C_{1-6}$alkyl; and wherein each of these moieties may be optionally substituted;

$R_9$ is hydrogen, $C(Z)R_6$ or optionally substituted $C_{1-10}$ alkyl, optionally substituted aryl or optionally substituted aryl-$C_{1-4}$ alkyl;

$R_{10}$ and $R_{20}$ are independently selected at each occurrence, from hydrogen or $C_{1-4}$alkyl;

$R_{10'}$ is independently selected at each occurrence, from hydrogen or $C_{1-4}$alkyl;

$R_{11}$ is $C_{1-4}$ alkyl, halo-substituted $C_{1-4}$ alkyl, $C_{2-4}$ alkenyl, $C_{2-4}$ alkynyl, $C_{3-7}$ cycloalkyl, $C_{5-7}$ cycloalkenyl, aryl, aryl$C_{1-4}$ alkyl, heteroaryl, heteroaryl$C_{1-4}$ alkyl, heterocyclyl, heterocyclyl$C_{1-4}$ alkyl, $(CR_{10}R_{20})_tOR_7$, $(CR_{10}R_{20})_tS(O)_mR_7$, $(CR_{10}R_{20})_t N(R_{10'})S(O)_2R_7$, or $(CR_{10}R_{20})_vNR_4R_{14}$; and wherein the aryl, arylalkyl, heteroaryl, heteroaryl $C_{1-4}$ alkyl, heterocyclyl, and heterocyclyl $C_{1-4}$ alkyl moieties may be optionally substituted;

$R_c$ is $C_{1-4}$ alkyl, halo-substituted $C_{1-4}$ alkyl, $C_{2-4}$ alkenyl, $C_{2-4}$ alkynyl, $C_{3-7}$ cycloalkyl, $C_{5-7}$ cycloalkenyl, aryl, aryl$C_{1-4}$ alkyl, heteroaryl, heteroaryl$C_{1-4}$ alkyl, heterocyclyl, heterocyclyl$C_{1-4}$ alkyl, $(CR_{10}R_{20})_vOR_7$, $(CR_{10}R_{20})_vS(O)_mR_7$, $(CR_{10}R_{20})_vN(R_{10'})S(O)_2R_7$, or $(CR_{10}R_{20})_vNR_4R_{14}$; and wherein the alkyl, cycloalkyl, cycloalkenyl, aryl, aryl $C_{1-4}$ alkyl, heteroaryl, heteroaryl $C_{1-4}$ alkyl, heterocyclic and heterocyclic $C_{1-4}$ alkyl moieties may be optionally substituted;

m is independently selected at each occurrence from 0 or an integer having a value of 1 or 2;

t is an integer having a value of 1 to 3;

v is 0 or an integer having a value of 1 or 2; and

Z is independently selected from oxygen or sulfur.

5. The compound according to claim 4 wherein $R_1$ is an optionally substituted phenyl or naphthyl.

6. The compound according to claim 5 wherein the phenyl is substituted one or more times independently by halogen, $C_{1-4}$ alkyl, $(CR_{10}R_{20})_vOR_8$, $(CR_{10}R_{20})_vNR_4R_{14}$, or halo-substituted-$C_{1-4}$ alkyl.

7. The compound according to claim 6 wherein the substituent is halogen, hydroxy, alkoxy, amino, or halosubstituted alkyl.

8. The compound according to claim 7 wherein the substituents are independently selected from fluorine, chlorine, methyl, or $CF_3$.

9. The compound according to claim 5 wherein the aryl ring is a phenyl ring, and the ring is mono-substituted in the 2, 4, or 6-position, di-substituted in the 2,4-position, or tri-substituted in the 2,4,6-position.

10. The compound according to claim 9 wherein $R_1$ is phenyl, 2-methyl-4-fluorophenyl, 2-methylphenyl, 2-chlorophenyl, 2-fluorophenyl, or 2-methyl-3-fluorophenyl.

11. The compound according to claim 1 wherein the $R_3$ moiety is optionally substituted one or more times independently with $C_{1-10}$ alkyl, halo-substituted $C_{1-10}$ alkyl, $C_{2-10}$ alkenyl, $C_{2-10}$alkynyl, $C_{3-7}$cycloalkyl, $C_{3-7}$cycloalkyl$C_{1-10}$ alkyl, $C_{5-7}$cycloalkenyl, $C_{5-7}$cycloalkenyl$C_{1-10}$ alkyl, halogen, cyano, nitro, $(CR_{10}R_{20})_nOR_6$, $(CR_{10}R_{20})_nSH$, $(CR_{10}R_{20})_nS(O)_mR_7$, $(CR_{10}R_{20})_nN(R_{10'})S(O)_2R_7$, $(CR_{10}R_{20})_nNR_4R_{14}$, $(CR_{10}R_{20})_nCN$, $(CR_{10}R_{20})_nS(O)_2NR_4R_{14}$, $(CR_{10}R_{20})_nC(Z)R_6$, $(CR_{10}R_{20})_nOC(Z)R_6$, $(CR_{10}R_{20})_nC(Z)OR_6$, $(CR_{10}R_{20})_nC(Z)NR_4R_{14}$, $(CR_{10}R_{20})_n N(R_{10'})C(Z)R_6$, $(CR_{10}R_{20})_nN(R_{10'})C(=N(R_{10'}))NR_4R_{14}$, $(CR_{10}R_{20})_nOC(Z)NR_4R_{14}$, $(CR_{10}R_{20})_nN(R_{10'})C(Z)NR_4R_{14}$, or $(CR_{10}R_{20})_nN(R_{10'})C(Z)OR_7$; and wherein $R_4$ and $R_{14}$ are each independently selected from hydrogen, optionally substituted $C_{1-4}$ alkyl, optionally substituted $C_{3-7}$ cycloalkyl, $C_{3-7}$ cycloalkyl$C_{1-4}$alkyl, optionally substituted aryl, or optionally substituted aryl-$C_{1-4}$ alkyl, heteroaryl, heteroaryl $C_{1-4}$ alkyl, heterocyclic, or heterocyclic $C_{1-4}$ alkyl; or $R_4$ and $R_{14}$ together with the nitrogen which they are attached form an optionally substituted heterocyclic ring of 4 to 7 members, which ring optionally contains an additional heteroatom selected from oxygen, sulfur or $NR_9$;

$R_6$ is hydrogen, $C_{1-10}$ alkyl, $C_{3-7}$ cycloalkyl, heterocyclyl, heterocyclyl $C_{1-10}$alkyl, aryl, aryl$C_{1-10}$ alkyl, heteroaryl or heteroaryl$C_{1-10}$ alkyl, wherein each of these moieties may be optionally substituted independently one or more times;

$R_7$ is $C_{1-6}$alkyl, aryl, aryl$C_{1-6}$alkyl, heterocyclic, heterocyclyl$C_{1-6}$ alkyl, heteroaryl, orheteroaryl$C_{1-6}$alkyl; and wherein each of these moieties may be optionally substituted independently one or more times;

$R_9$ is hydrogen, $C(Z)R_6$ or optionally substituted $C_{1-10}$ alkyl, optionally substituted aryl or optionally substituted aryl-$C_{1-4}$ alkyl, wherein the optional substituents are independently substituted;

$R_{10}$ and $R_{20}$ are independently selected from hydrogen or $C_{1-4}$alkyl;

$R_{10'}$ is independently selected from hydrogen or $C_{1-4}$alkyl;

m is independently selected at each occurrence from 0 or an integer having a value of 1 or 2;

n is 0 or an integer having a value of 1 to 10; and

Z is independently selected at each occurrence from oxygen or sulfur.

12. The compound according to claim 11 wherein $R_3$ is an optionally substituted $C_{1-10}$ alkyl, $C_{3-7}$ cycloalkyl, $C_{3-7}$ cycloalkylalkyl, or aryl.

13. The compound according to claim 12 wherein the optional substituents are independently selected at each occurrence from halogen, $C_{1-10}$ alkyl, halo-substituted $C_{1-10}$ alkyl, $(CR_{10}R_{20})_nOR_6$, or $(CR_{10}R_{20})_nNR_4R_{14}$.

14. The compound according to claim 13 wherein the optional substituents are halogen, methyl, hydroxy, alkoxy, amino, or $CF_3$.

15. The compound according to claim 11 wherein $R_3$ is phenyl, 4-trifluoromethyl-phenyl, 2-fluorophenyl, 2,6-difluoro-phenyl, 2,4-difluoro-phenyl, 2-chlorophenyl, 2-methylphenyl, or 2,6-dimethylphenyl.

16. The compound according to claim 1 wherein $R_2$ and $R_{2'}$ are independently hydrogen or $C_{1-10}$ alkyl.

17. The compound according to claim 1 wherein Rg is an optionally substituted $C_{1-10}$ alkyl.

18. The compound according to claim 1 which is:

N-cyano-N'-(2-{[8-(2,6-difluorophenyl)-4-(4-fluoro-2-methylphenyl)-7-oxo-7,8-dihydropyrido[2,3-d]pyrimidin-2-yl]amino}ethyl)guanidine;

N-cyano-N'-(2-{[8-(2,6-difluorophenyl)-4-(4-fluoro-2-methylphenyl)-7-oxo-7,8-dihydropyrido[2,3-d]pyrimidin-2-yl]amino}ethyl)-N"-methylguanidine;

N-cyano-N'-(2-{[8-(2,6-difluorophenyl)-4-(4-fluoro-2-methylphenyl)-7-oxo-7,8-dihydropyrido[2,3-d]pyrimidin-2-yl]amino}ethyl)-N"-ethylguanidine;

N-Cyano-N'-(2-{[4-(2,4-difluorophenyl)-8-(2-fluorophenyl)-7-oxo-7,8-dihydropyrido[2,3-d]pyrimidin-2-yl]amino}ethyl)guanidine;

N-Cyano-N'-(2-{[8-(2,6-difluorophenyl)-4-(2-methylphenyl)-7-oxo-7,8-dihydropyrido[2,3-d]pyrimidin-2-yl]amino}ethyl)guanidine;

N-Cyano-N'-(2-{[8-(2,6-difluorophenyl)-4-(4-fluorophenyl)-7-oxo-7,8-dihydropyrido[2,3-d]pyrimidin-2-yl]amino}ethyl)guanidine;

N-cyano-N'-(2-{[4-(2,4-difluorophenyl)-8-(2,6-difluorophenyl)-7-oxo-7,8-dihydropyrido[2,3-d]pyrimidin-2-yl]amino}ethyl)guanidine; or a pharmaceutically acceptable salt thereof.

19. A pharmaceutical composition comprising an effective amount of a compound according to claim 1 and a pharmaceutically acceptable carrier or diluent.

20. A pharmaceutical composition comprising an effective amount of a compound, or pharmaceutically acceptable salt, according to claim 1, in admixture with one or more pharmaceutically acceptable carriers, diluents or excipients, for administration by intravenous, intramuscular, subcutaneous, intranasal, oral inhalation, intrarectal, intravaginal or intraperitoneal means.

* * * * *